(12) United States Patent
Bolin et al.

(10) Patent No.: US 7,714,126 B2
(45) Date of Patent: May 11, 2010

(54) DIACYLGLYCEROL ACYLTRANSFERASE INHIBITORS

(75) Inventors: David Robert Bolin, Montclair, NJ (US); Adrian Wai-Hing Cheung, Glen Rock, NJ (US); Fariborz Firooznia, Florham Park, NJ (US); Matthew Michael Hamilton, Hackettstown, NJ (US); Shiming Li, Edison, NJ (US); Lee Apostle McDermott, Parlin, NJ (US); Yimin Qian, Wayne, NJ (US); Weiya Yun, Warren, NJ (US)

(73) Assignee: Via Pharmaceuticals, Inc., San Francisco, CA (US)

( * ) Notice: Subject to any disclaimer, the term of this patent is extended or adjusted under 35 U.S.C. 154(b) by 579 days.

(21) Appl. No.: 11/601,429

(22) Filed: Nov. 17, 2006

(65) Prior Publication Data

US 2007/0123504 A1   May 31, 2007

Related U.S. Application Data

(60) Provisional application No. 60/740,578, filed on Nov. 28, 2005, provisional application No. 60/849,352, filed on Oct. 4, 2006.

(51) Int. Cl.
C07D 279/00 (2006.01)
(52) U.S. Cl. .................. 544/59; 546/309; 548/200; 548/236
(58) Field of Classification Search .................. 548/236
See application file for complete search history.

(56) References Cited

U.S. PATENT DOCUMENTS

| 2004/0185559 A1 | 9/2004 | Monia et al. |
| 2004/0204427 A1 | 10/2004 | Chen et al. |
| 2004/0224997 A1 | 11/2004 | Smith et al. |

FOREIGN PATENT DOCUMENTS

| EP | 1219716 | 7/2002 |
| JP | 2004067635 | 8/2002 |
| WO | WO 03/040107 A1 | 5/2003 |
| WO | WO2004022551 | 3/2004 |
| WO | WO2004047755 | 6/2004 |
| WO | WO 2004/099157 A1 | 11/2004 |
| WO | WO2004100881 | 11/2004 |
| WO | WO2005103907 | 3/2005 |
| WO | WO2005044250 | 5/2005 |

OTHER PUBLICATIONS

Subauste and Burant, Current Drug Targets—Immune, Endocrine & Metabolic Disorders (2003) 3, 263-270.
Mayorek et al, European Journal of Biochemistry (1989) 182, 395-400.
Farese et al, Current Opinions in Lipidology (2000) 11, 229-234.
Coleman et al, Journal of Molecular Biology (1978) 253, 7256-7261.
Yu et al, Journal of Molecular Biology (2002) 277, 50876-50884.
Colman, Methods in Enzymology (1992) 209, 98-104.
Owen et al, Biochemical Journal (1997) 323 (pt 1), 17-21.
Waterman et al, Journal of Lipid Research (2002) 43, 1555-156.
Shelness and Sellers, Current Opinions in Lipidology (2001) 12, 151-157.
Cases et al, Proceedings of the National Academy of Science, USA (1998) 95, 13018-13023.
Lardizabal et al, Journal of Biological Chemistry (2001) 276, 38862-38869.
Cases et al, Journal of Biological Chemistry (2001) 276, 38870-38876.
Smith et al, Nature Genetics (2000) 25, 87-90.
Lehner and Kuksis, Progress in Lipid Research (1996) 35, 169-210.
Chen and Farese, Trends in Cardiovascular Medicine (2000) 10, 188-192.
Chen and Farese, Current Opinions in Clinical Nutrition and Metabolic Care (2002) 5, 359-363.
Chen et al, Journal of Clinical Investigation (2002) 109, 1049-1055.
Buhman et al, Journal of Biological Chemistry (2002) 277, 25474-25479.
Kahn, Nature Genetics (2000) 25, 6-7.
Yanovski and Yanovski, New England Journal of Medicine (2002) 346, 591-602.
Lewis et al, Endocrine Reviews (2002) 23, 201.
Brazil, Nature Reviews Drug Discovery (2002) 1, 408.
Malloy and Kane, Advances in Internal Medicine (2001) 47, 111.
Yu and Ginsberg, Annals of Medicine (2004) 36, 252-261.
Burrows et al, 26th National Medicinal Chemistry Symposium (1998) poster C-22.
Tabata et al, Phytochemistry (1997) 46, 683-687 and.
Casaschi et al, Journal of Nutrition (2004) 134, 1340-1346.
Kurogi et al, Journal of Medicinal Chemistry (1996) 39, 1433-1437.
Goto, et al, Chemistry and Pharmaceutical Bulletin (1996) 44, 547-551.
Ikeda, et al, Thirteenth International Symposium on Athersclerosis (2003), abstract 2P-0401.
Colman et al, Biochimica et Biophysica Acta (1992) 1125, 203-9.
Mayorek and Bar-Tana, Journal of Biological Chemistry (1985) 260, 6528-6532.
Noriko et al, (Journal of Antibiotics (1999) 52, 815-826.
Tomoda et al, Journal of Antibiotics (1995) 48, 942-7.

(Continued)

*Primary Examiner*—James O Wilson
*Assistant Examiner*—Brian McDowell

(57) ABSTRACT

Provided herein are compounds of the formula (I):

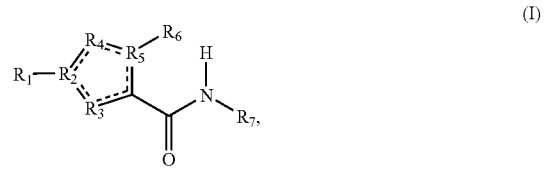

as well as pharmaceutically acceptable salts thereof, wherein the substituents are as those disclosed in the specification. These compounds, and the pharmaceutical compositions containing them, are useful for the treatment of diseases such as, for example, obesity, type II diabetes mellitus and metabolic syndrome.

11 Claims, No Drawings

OTHER PUBLICATIONS

Chung et al, Planta Medica (2004) 70, 258-260.
Lee et al, Planta Medica (2004) 70, 197-200.
Lee et al, Journal of Antibiotics (2003) 56, 967-969.
Ko et al, Archives of Pharmaceutical Research (2002) 25, 446-448.
Zhu et al, Atherosclerosis (2002) 164, 221-228.
Ko, et al, Planta Medica (2002) 68, 1131-1133.
H. Gilman and R.R. Burtner *J. Amer. Chem. Soc.* 71 1213 (1949.
D. Nguyen *J. Chem. Soc. Perkin Trans. I* 1025 (1985.
J. Coste et al *J. Org. Chem.* 59 2437 (1994).
M Boyeman et al *Int. J. Peptide Protein Res.* 37 252 (1991.
A. Suzuki, in *Metal-Catalyzed Cross-Coupling Reaction*, Diederich F, Stang P.J, eds, Wiley, 1998 pp. 49-97.
F. Bellina et al *Synthesis* 2419 (2004).
Varano, F. et al (*J. Med. Chem.* 2002, 45, 1035.
Zhang, J. et al (*Bioorg. Med. Chem. Lett.* 2000, 10, 2575).
B. Plouvier et al *Heterocycles* 32 693 (1991).
R.A. Kretchmer and R.A. Laitar *J. Org. Chem.* 43 4596 (1978).
Mann, et. al., Org. Lett, 2003, 5 (24), 4567.
Tullis, et. al. *Bioorg. Med. Chem. Lett.* 2001, 11 (15), 1975.
Crank, et. al., *J. Med. Chem.* 1971, 14 (11), 1075.
Doyle, et. al., *J. Org. Chem.* 1977, 42, 2429.
Hodgetts, et. al., *Org. Lett.* 2002, 4 (17), 2905.
Bolin, et. al., *Int. J. Peptide Protein Res.* 1989, 33, 353.
Cynkowski, et. al., *J. Chem. Soc. Chem. Commun.* 1995, 2335.
E. Von Arx, M. Faupel and M Brugger, *J. Chromatography*, 1976, 220, 224-228.
Barlos, et. al., *Journal of the Chemical Society, Chemical Communication* 6, 474-475, 1987.
Sznaidman, et al., *Bioorg. Med. Chem. Lett.* 2003, 13, 1517.

DIACYLGLYCEROL ACYLTRANSFERASE INHIBITORS

PRIORITY TO RELATED APPLICATIONS

This application claims the benefit of U.S. Provisional Application No. 60/740,578, filed Nov. 28, 2005, and U.S. Provisional Application No. 60/849,352, filed Oct. 4, 2006, which are hereby incorporated by reference in their entirety.

FIELD OF THE INVENTION

The invention relates to inhibitors of diacylglycerol acyltransferase. The inhibitors include, for example, oxazoles, and are useful for the treatment of diseases such as obesity, type II diabetes mellitus, dyslipidemia and metabolic syndrome.

All documents cited or relied upon below are expressly incorporated herein by reference.

BACKGROUND OF THE INVENTION

Triglycerides or triacylglycerols are the major form of energy storage in eukaryotic organisms. In mammals, these compounds are primarily synthesized in three tissues: the small intestine, liver, and adipocytes. Triglycerides or triacylglycerols support the major functions of dietary fat absorption, packaging of newly synthesized fatty acids and storage in fat tissue (see Subauste and Burant, Current Drug Targets—Immune, Endocrine & Metabolic Disorders (2003) 3, 263-270).

Diacylglycerol O-acyltransferase, also known as diglyceride acyltransferase or DGAT, is a key enzyme in triglyceride synthesis. DGAT catalyzes the final and rate-limiting step in triacylglycerol synthesis from 1,2-diacylglycerol (DAG) and long chain fatty acyl CoA as substrates. Thus, DGAT plays an essential role in the metabolism of cellular diacylglycerol and is critically important for triglyceride production and energy storage homeostasis (see Mayorek et al, European Journal of Biochemistry (1989) 182, 395-400).

DGAT has a specificity for sn-1,2 diacylglycerols and will accept a wide variety of fatty acyl chain lengths (see Farese et al, Current Opinions in Lipidology (2000) 11, 229-234). DGAT activity levels increase in fat cells as they differentiate in vitro and recent evidence suggests that DGAT may be regulated in adipose tissue post-transcriptionally (see Coleman et al, Journal of Molecular Biology (1978) 253, 7256-7261 and Yu et al, Journal of Molecular Biology (2002) 277, 50876-50884). DGAT activity is primarily expressed in the endoplasmic reticulum (see Colman, Methods in Enzymology (1992) 209, 98-104). In hepatocytes, DGAT activity has been shown to be expressed on both the cytosolic and luminal surfaces of the endoplasmic reticular membrane (see Owen et al, Biochemical Journal (1997) 323 (pt 1), 17-21 and Waterman et al, Journal of Lipid Research (2002) 43, 1555-156). In the liver, the regulation of triglyceride synthesis and partitioning, between retention as cytosolic droplets and secretion, is of primary importance in determining the rate of VLDL production (see Shelness and Sellers, Current Opinions in Lipidology (2001) 12, 151-157 and Owen et al, Biochemical Journal (1997) 323 (pt 1), 17-21).

Two forms of DGAT have been cloned and are designated DGAT1 and DGAT2 (see Cases et al, Proceedings of the National Academy of Science, USA (1998) 95, 13018-13023, Lardizabal et al, Journal of Biological Chemistry (2001) 276, 38862-38869 and Cases et al, Journal of Biological Chemistry (2001) 276, 38870-38876). Although both enzymes utilize the same substrates, there is no homology between DGAT1 and DGAT2. Both enzymes are widely expressed however some differences do exist in the relative abundance of expression in various tissues.

The gene encoding mouse DGAT1 has been used to create DGAT knock-out. These mice, although unable to express a functional DGAT enzyme (Dgat−/− mice), are viable and continue to synthesize triglycerides (see Smith et al, Nature Genetics (2000) 25, 87-90). This would suggest that multiple catalytic mechanisms contribute to triglyceride synthesis, such as DGAT2. An alternative pathway has also been shown to form triglycerides from two diacylglycerols by the action of diacylglycerol transacylase (see Lehner and Kuksis, Progress in Lipid Research (1996) 35, 169-210).

Dgat−/− mice are resistant to diet-induced obesity and remain lean. When fed a high fat diet, Dgat−/− mice maintain weights comparable to mice fed a diet with regular fat content. Dgat−/− mice have lower tissue triglyceride levels. The resistance to weight gain seen in the knockout mice, which have a slightly higher food intake, is due to an increased energy expenditure and increased sensitivity to insulin and leptin (see Smith et al, Nature Genetics (2000) 25, 87-90, Chen and Farese, Trends in Cardiovascular Medicine (2000) 10, 188-192, Chen and Farese, Current Opinions in Clinical Nutrition and Metabolic Care (2002) 5, 359-363 and Chen et al, Journal of Clinical Investigation (2002) 109, 1049-1055). Dgat−/− mice have reduced rates of triglyceride absorption, improved triglyceride metabolism, and improved glucose metabolism, with lower glucose and insulin levels following a glucose load, in comparison to wild-type mice (see Buhman et al, Journal of Biological Chemistry (2002) 277, 25474-25479 and Chen and Farese, Trends in Cardiovascular Medicine (2000) 10, 188-192).

Disorders or imbalances in triglyceride metabolism, both absorption as well as de novo synthesis, have been implicated in the pathogenesis of a variety of disease risks These include obesity, insulin resistance syndrome, type II diabetes, dyslipidemia, metabolic syndrome (syndrome X) and coronary heart disease (see Kahn, Nature Genetics (2000) 25, 6-7, Yanovski and Yanovski, New England Journal of Medicine (2002) 346, 591-602, Lewis et al, Endocrine Reviews (2002) 23, 201, Brazil, Nature Reviews Drug Discovery (2002) 1, 408, Malloy and Kane, Advances in Internal Medicine (2001) 47, 111, Subauste and Burant, Current Drug Targets—Immune, Endocrine & Metabolic Disorders (2003) 3, 263-270 and Yu and Ginsberg, Annals of Medicine (2004) 36, 252-261). Compounds that can decrease the synthesis of triglycerides from diacylglycerol by inhibiting or lowering the activity of the DGAT enzyme would be of value as therapeutic agents for the treatment diseases associated with abnormal metabolism of triglycerides.

Known inhibitors of DGAT include: dibenzoxazepinones (see Ramharack, et al, EP1219716 and Burrows et al, 26th National Medicinal Chemistry Symposium (1998) poster C-22), substituted amino-pyrimidino-oxazines (see Fox et al, WO2004047755), chalcones such as xanthohumol (see Tabata et al, Phytochemistry (1997) 46, 683-687 and Casaschi et al, Journal of Nutrition (2004) 134, 1340-1346), substituted benzyl-phosphonates (see Kurogi et al, Journal of Medicinal Chemistry (1996) 39, 1433-1437, Goto, et al, Chemistry and Pharmaceutical Bulletin (1996) 44, 547-551, Ikeda, et al, Thirteenth International Symposium on Atherosclerosis (2003), abstract 2P-0401, and Miyata, et al, JP 2004067635), aryl alkyl acid derivatives (see Smith et al, WO2004100881 and US20040224997), furan and thiophene derivatives (see WO2004022551), pyrrolo[1,2b]pyridazine derivatives (see Fox et al, WO2005103907), and substituted sulfonamides (see Budd Haeberlein and Buckett, WO20050442500).

Also known to be inhibitors of DGAT are: 2-bromo-palmitic acid (see Colman et al, Biochimica et Biophysica Acta (1992) 1125, 203-9), 2-bromo-octanoic acid (see Mayorek and Bar-Tana, Journal of Biological Chemistry (1985) 260, 6528-6532), roselipins (see Noriko et al, (Journal of Antibiotics (1999) 52, 815-826), amidepsin (see Tomoda et al, Journal of Antibiotics (1995) 48, 942-7), isochromophilone, prenylflavonoids (see Chung et al, Planta Medica (2004) 70, 258-260), polyacetylenes (see Lee et al, Planta Medica (2004) 70, 197-200), cochlioquinones (see Lee et al, Journal of Antibiotics (2003) 56, 967-969), tanshinones (see Ko et al, Archives of Pharmaceutical Research (2002) 25, 446-448), gemfibrozil (see Zhu et al, Atherosclerosis (2002) 164, 221-228), and substituted quinolones (see Ko, et al, Planta Medica (2002) 68, 1131-1133). Also known to be modulators of DGAT activity are antisense oligonucleotides (see Monia and Graham, US20040185559).

A need exists in the art, however, for additional DGAT inhibitors that have efficacy for the treatment of metabolic disorders such as, for example, obesity, type II diabetes mellitus and metabolic syndrome. Further, a need exists in the art for DGAT inhibitors having $IC_{50}$ values less than about 1 μM.

SUMMARY OF THE INVENTION

In one embodiment of the present invention, provided is a compound of the formula (I):

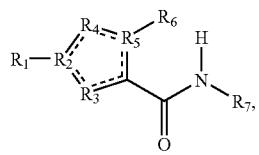

(I)

wherein:
$R_1$ is unsubstituted aryl, aryl substituted with a group selected from the group consisting of alkyl, —O-alkyl, haloalkoxy, methoxy-ethoxy and halogen, heteroaryl, alkyl or cycloalkyl;
$R_2$ is C or N;
$R_3$ is C, N, S or O;
$R_4$ is C, O, S or N;
$R_5$ is C, N or S;
$R_6$ is H, alkyl, halogen, haloalkyl, thioalkyl or absent;
$R_7$ is

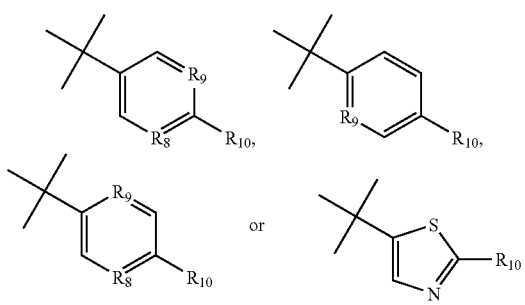

at least one of $R_8$ or $R_9$ is N; and
$R_{10}$ is —$NR_{11}R_{12}$, O-alkyl, hydroxy-dimethylethylamino, hydroxyl-methylethylamino, cyclohept-2-ylamino, morpholino, thiomorpholino, oxothiomorpholino, dioxothiomorpholino, alkyl-carbamoyl-alkyl-amino, difluoroazetidine, ethoxyazetidine, azetidin-3-yloxy acetic acid tert-butyl ether, azetidine-3-yloxy acetic acid hydrochloride, or a 4- to 6-membered cyclic ring having from 1 to 3 hetero ring atoms selected from the group consisting of S, N and O, unsubstituted or substituted with a group selected from the group consisting of amino, amide, —$N(CH_3)C(O)CH_3$, cyclopropanecarbonyl-methyl, —$OCH_3$, —$OCH_2C(O)OC(CH_3)_3$, $OCH_2C(O)OH$, —$CH_2OH$, —$CH_2OCH_3$ and —OH;
$R_{11}$ is H, lower alkyl, alkyl ether, alkyl-aryl, trifluoromethyl, methoxymethyl, cyclopropylmethoxy-ethyl, ethoxymethyl, —$CH_2CH_2CN$, alkyl alcohol, acyl, cycloalkyl, or a 4- to 6-membered cyclic ring having from 1 to 3 hetero ring atoms selected from the group consisting of S, N and O, unsubstituted or substituted with a group selected from the group consisting of —$OCH_3$, —$CH_2OH$, —$CH_2OCH_3$, —$OCH_2C(O)OC(CH_3)_3$, —$OCH_2C(O)OH$ and —OH;
$R_{12}$ is H or lower alkyl;

or a pharmaceutically acceptable salt thereof.

In another embodiment of the present invention, provided is a pharmaceutical composition, comprising a therapeutically effective amount of a compound according to formula I or a pharmaceutically acceptable salt thereof and a pharmaceutically acceptable carrier.

In a further embodiment of the present invention, provided is a method of treating obesity, type II diabetes or metabolic syndrome, comprising the step of administering a therapeutically effective amount of a compound according to formula I to a patient in need thereof.

DETAILED DESCRIPTION OF THE INVENTION

The present invention pertains to DGAT inhibitors that are derivatives of, for example, oxazoles. In a preferred embodiment, the invention provides compounds of the formula:

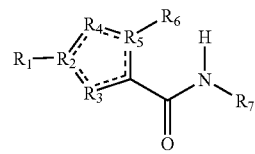

as well as pharmaceutically acceptable salts thereof.

It is to be understood that the terminology employed herein is for the purpose of describing particular embodiments, and is not intended to be limiting. Further, although any methods, devices and materials similar or equivalent to those described herein can be used in the practice or testing of the invention, the preferred methods, devices and materials are now described.

As used herein, the term "alkyl" means, for example, a branched or unbranched, cyclic or acyclic, saturated or unsaturated (e.g. alkenyl or alkynyl) hydrocarbyl radical which may be substituted or unsubstituted. Where cyclic, the alkyl group is preferably $C_3$ to $C_{12}$, more preferably $C_4$ to $C_{10}$, more preferably $C_4$ to $C_7$. Where acyclic, the alkyl group is preferably $C_1$ to $C_{10}$, more preferably $C_1$ to $C_6$, more preferably methyl, ethyl, propyl (n-propyl or isopropyl), butyl (n-butyl, isobutyl or tertiary-butyl) or pentyl (including n-pentyl and isopentyl), more preferably methyl. It will be appreciated therefore that the term "alkyl" as used herein includes alkyl (branched or unbranched), substituted alkyl (branched or unbranched), alkenyl (branched or unbranched), substituted alkenyl (branched or unbranched), alkynyl (branched or unbranched), substituted alkynyl (branched or unbranched), cycloalkyl, substituted cycloalkyl, cycloalkenyl, substituted cycloalkenyl, cycloalkynyl and substituted cycloalkynyl.

As used herein, the term "lower alkyl" means, for example, a branched or unbranched, cyclic or acyclic, saturated or unsaturated hydrocarbyl radical wherein said cyclic lower alkyl group is $C_5$, $C_6$ or $C_7$, and wherein said acyclic lower alkyl group is $C_1$, $C_2$, $C_3$ or $C_4$, and is preferably selected from methyl, ethyl, propyl (n-propyl or isopropyl) or butyl (n-butyl, isobutyl or tertiary-butyl). It will be appreciated therefore that the term "lower alkyl" as used herein includes, for example, lower alkyl (branched or unbranched) and cycloloweralkyl.

As used herein, the term "aryl" means, for example, a substituted or unsubstituted carbocyclic aromatic group, such as, for example, phenyl or naphthyl. The term "heteroaryl", alone or in combination with other groups, means a monocyclic or bicyclic radical of 5 to 12 ring atoms having at least one aromatic ring containing one, two, or three ring heteroatoms selected from N, O, and S, the remaining ring atoms being C, with the understanding that the attachment point of the heteroaryl radical will be on an aromatic ring. One or two ring carbon atoms of the heteroaryl group may be replaced with a carbonyl group. The heteroaryl group described above may be substituted independently with one, two, or three substituents, preferably one or two substituents such as, for example, halogen, hydroxy, $C_{1-6}$ alkyl, halo $C_{1-6}$ alkyl, $C_{1-6}$ alkoxy, $C_{1-6}$ alkyl sulfonyl, $C_{1-6}$ alkyl sulfinyl, $C_{1-6}$ alkylthio, amino, amino $C_{1-6}$ alkyl, mono- or di-substituted amino-$C_{1-6}$ alkyl, nitro, cyano, acyl, carbamoyl, mono- or di-substituted amino, aminocarbonyl, mono- or di-substituted amino-carbonyl, aminocarbonyl $C_{1-6}$ alkoxy, mono- or di-substituted amino-carbonyl-$C_{1-6}$ alkoxy, hydroxy-$C_{1-6}$ alkyl, carboxyl, $C_{1-6}$ alkoxy carbonyl, aryl $C_{1-6}$ alkoxy, heteroaryl $C_{1-6}$ alkoxy, heterocyclyl $C_{1-6}$ alkoxy, $C_{1-6}$ alkoxycarbonyl $C_{1-6}$ alkoxy, carbamoyl $C_{1-6}$ alkoxy and carboxyl $C_{1-6}$ alkoxy, preferably halogen, hydroxy, $C_{1-6}$ alkyl, halo $C_{1-6}$ alkyl, $C_{1-6}$ alkoxy, $C_{1-6}$ alkyl sulfonyl, $C_{1-6}$ alkyl sulfinyl, $C_{1-6}$ alkylthio, amino, mono-$C_{1-6}$ alkyl substituted amino, di-$C_{1-6}$ alkyl substituted amino, amino $C_{1-6}$ alkyl, mono-$C_{1-6}$ alkyl substituted amino-$C_{1-6}$ alkyl, di-$C_{1-6}$ alkyl substituted amino-$C_{1-6}$ alkyl, nitro, carbamoyl, mono- or di-substituted amino-carbonyl, hydroxy-$C_{1-6}$ alkyl, carboxyl, $C_{1-6}$ alkoxy carbonyl and cyano.

The alkyl and aryl groups may be substituted or unsubstituted. Where substituted, there will generally be, for example, 1 to 3 substituents present, preferably 1 substituent. Substituents may include, for example: carbon-containing groups such as alkyl, aryl, arylalkyl (e.g. substituted and unsubstituted phenyl, substituted and unsubstituted benzyl); halogen atoms and halogen-containing groups such as haloalkyl (e.g. trifluoromethyl); oxygen-containing groups such as alcohols (e.g. hydroxyl, hydroxyalkyl, aryl(hydroxyl)alkyl), ethers (e.g. alkoxy, aryloxy, alkoxyalkyl, aryloxyalkyl), aldehydes (e.g. carboxaldehyde), ketones (e.g. alkylcarbonyl, alkylcarbonylalkyl, arylcarbonyl, arylalkylcarbonyl, arylcarbonylalkyl), acids (e.g. carboxy, carboxyalkyl), acid derivatives such as esters (e.g. alkoxycarbonyl, alkoxycarbonylalkyl, alkylcarbonyloxy, alkylcarbonyloxyalkyl), amides (e.g. aminocarbonyl, mono- or di-alkylaminocarbonyl, aminocarbonylalkyl, mono- or di-alkylaminocarbonylalkyl, arylaminocarbonyl), carbamates (e.g. alkoxycarbonylamino, aryloxycarbonylamino, aminocarbonyloxy, mono- or di-alkylaminocarbonyloxy, arylaminocarbonyl) and ureas (e.g. mono- or di-alkylaminocarbonylamino or arylaminocarbonylamino); nitrogen-containing groups such as amines (e.g. amino, mono- or di-alkylamino, aminoalkyl, mono- or di-alkylaminoalkyl), azides, nitriles (e.g. cyano, cyanoalkyl), nitro; sulfur-containing groups such as thiols, thioethers, sulfoxides and sulfones (e.g. alkylthio, alkylsulfinyl, alkylsulfonyl, alkylthioalkyl, alkylsulfinylalkyl, alkylsulfonylalkyl, arylthio, arylsulfinyl, arylsulfonyl, arylthioalkyl, arylsulfinylalkyl, arylsulfonylalkyl); and heterocyclic groups containing one or more, preferably one, heteroatom, (e.g. thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl and carbolinyl).

The lower alkyl groups may be substituted or unsubstituted, preferably unsubstituted. Where substituted, there will generally be, for example, 1 to 3 substituents present, preferably 1 substituent.

As used herein, the term "alkoxy" means, for example, alkyl-O— and "alkoyl" means, for example, alkyl-CO—. Alkoxy substituent groups or alkoxy-containing substituent groups may be substituted by, for example, one or more alkyl groups.

As used herein, the term "halogen" means, for example, a fluorine, chlorine, bromine or iodine radical, preferably a fluorine, chlorine or bromine radical, and more preferably a fluorine or chlorine radical.

As used herein, the term "pharmaceutically acceptable salt" means any pharmaceutically acceptable salt of the compound of formula (I). Salts may be prepared from pharmaceutically acceptable non-toxic acids and bases including inorganic and organic acids and bases. Such acids include, for example, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like. Particularly preferred are fumaric, hydrochloric, hydrobromic, phosphoric, succinic, sulfuric and methanesulfonic acids. Acceptable base salts include alkali metal (e.g. sodium, potassium), alkaline earth metal (e.g. calcium, magnesium) and aluminium salts.

Compounds of the present invention can be prepared beginning with commercially available starting materials and utilizing general synthetic techniques and procedures known to those skilled in the art. Outlined below are reaction schemes suitable for preparing such compounds. Further exemplification is found in the specific Examples detailed below.

Scheme 1

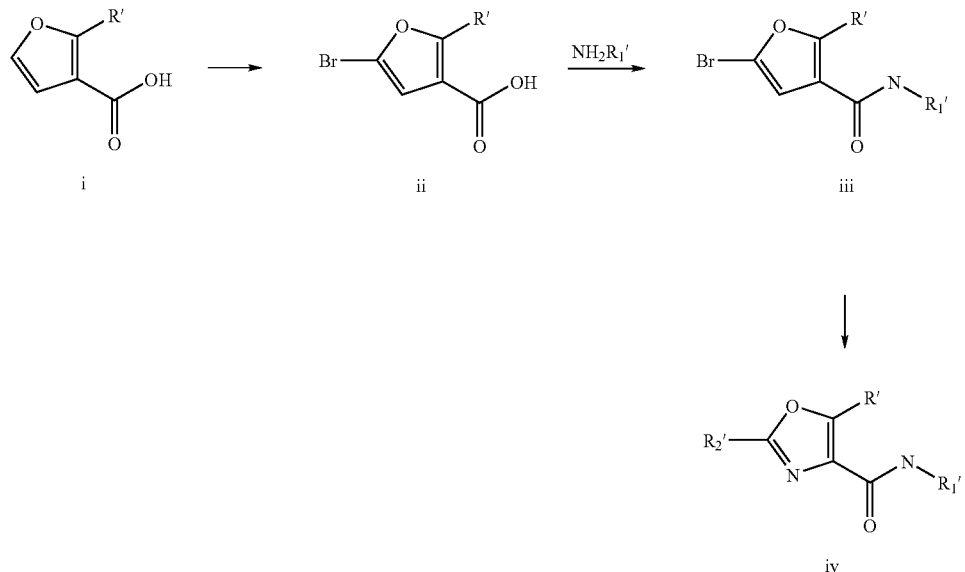

As shown in Scheme 1, using a method similar to Gilman and Burtner (see H. Gilman and R. R. Burtner *J. Amer. Chem. Soc.* 71 1213 (1949)), 2-substituted-3-furoic acid i, where R' is halogen, lower alkyl, haloalkyl, alkoxy, thioalkoxy, haloalkoxy, can be brominated at C-5 with bromine in acetic acid to give 5-bromo-furoic acid ii. Furoic acid ii can be reacted to form amide iii with various amines, where $R_1'$ is aryl, substituted aryl, heteroaryl, substituted heteroaryl, cycloalkyl or cycloheteroalkyl. Various standard amide bond forming conditions, as practiced by those skilled in the art, may be used. Typically ii and an amine $NH_2R_1'$, in an appropriate solvent, may be treated with a base, such as triethyl amine, and an amide bond forming reagent such as BOP, PyBroP or EDCI and HOBT (see D. Nguyen *J. Chem. Soc. Perkin Trans. I* 1025 (1985), J. Coste et al *J. Org. Chem.* 59 2437 (1994) and M Boyeman et al *Int. J. Peptide Protein Res.* 37 252 (1991)) to yield amide iii. Using standard palladium catalyzed "cross coupling" procedures (see A. Suzuki, in *Metal-Catalyzed Cross-Coupling Reaction*, Diederich F, Stang P. J, eds, Wiley, 1998 pp 49-97 and F. Bellina et al *Synthesis* 2419 (2004)), 5-bromo-furoic acid amide iii can be heated with a commercially available substituted phenylboronic acid or boronate ester in the presence of a base, typically an aqueous solution of sodium carbonate, in an appropriate solvent, typically, DME, DMF or toluene, with a catalytic amount of palladium, typically $Pd[PPh_3]_4$, to yield iv, where $R_2'$ is aryl, substituted aryl, heteroaryl, substituted heteroaryl.

Scheme 2

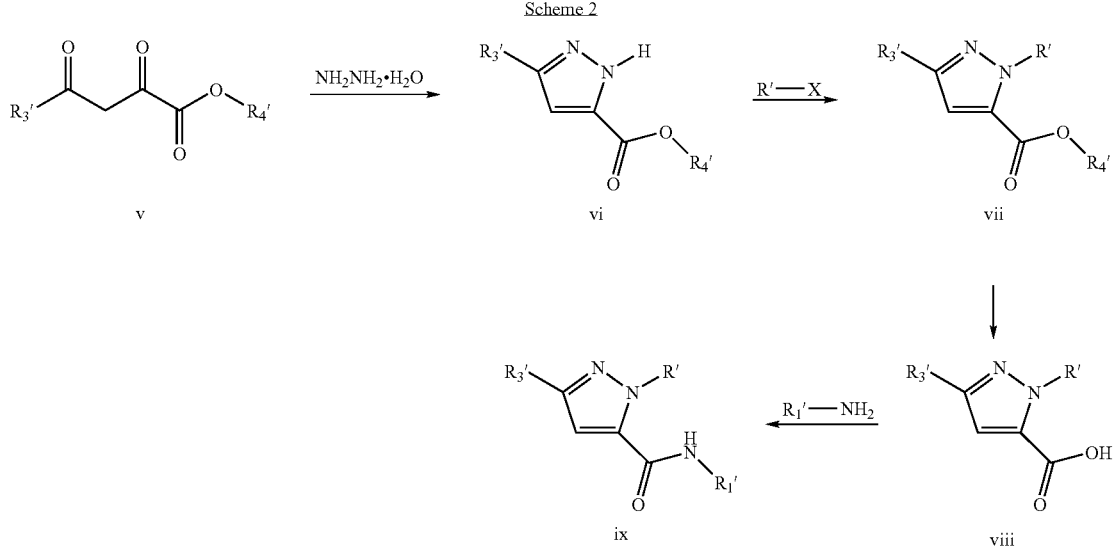

As shown in Scheme 2, pyrazole vi could be prepared using a method similar to that used by Varano, F. et al (*J. Med. Chem.* 2002, 45, 1035) in which the keto ester v can be treated with hydrazine hydrate with heating in a solvent such as ethanol to give pyrazole vi, where $R_3'$ is aryl, substituted aryl, heteroaryl, substituted heteroaryl, alkyl, cycloalkyl, and $R_4'$ is lower alkyl, preferably methyl or ethyl. Pyrazole vi can be alkylated under basic conditions, preferably sodium hydride as base, as described by Zhang, J. et al (*Bioorg. Med. Chem. Lett.* 2000, 10, 2575) to give predominantly isomer vii.

Substituted pyrazole ester vii can be hydrolyzed by heating with a strong base, typically sodium hydroxide in an aqueous/organic mixed solvent, preferred is methanol, to give the pyrazole acid viii.

Pyrazole acid viii can be reacted to form amides with various amines, where $R_1'$ is aryl, substituted aryl, heteroaryl, substituted heteroaryl, cycloalkyl or cycloheteroalkyl. Various standard amide bond forming conditions, as practiced by those skilled in the art, may be used. Typically viii and an amine $NH_2R_1'$, in an appropriate solvent, may be treated with a base, such as triethyl amine, and an amide bond forming reagent such as BOP, PyBroP or EDCI and HOBT to yield amide ix.

in $CCl_4$ under reflux to give xi. The keto bromide xi upon heating, preferably in a microwave reactor, with urea in an appropriate solvent, preferably ethanol, cyclizes to yield substituted 2-amino oxazole xii. Heating of xii with cupric (II) bromide and t-butylnitrite in dry acetonitrile under argon yields 2-bromo-oxazole xiii.

The substituted 2-bromo-oxazole ester xiii can be can be hydrolyzed by heating with a strong base, typically sodium hydroxide in an aqueous/organic mixed solvent, preferred is methanol, to give the bromo-oxazole acid xiv.

Oxazole acid xiv can be reacted to form amides with various amines, where $R_1'$ is aryl, substituted aryl, heteroaryl, substituted heteroaryl, cycloalkyl or cycloheteroalkyl. Various standard amide bond forming conditions, as practiced by those skilled in the art, may be used. Typically xiv and an amine $NH_2R_1'$, in an appropriate solvent, may be treated with a base, such as triethyl amine, and an amide bond forming reagent such as BOP, PyBroP or EDCI and HOBT to yield amide xv.

Using standard palladium catalyzed "cross coupling" procedures, 2-oxazole acid amide xv can be heated with a commercially available substituted phenylboronic acid or bor-

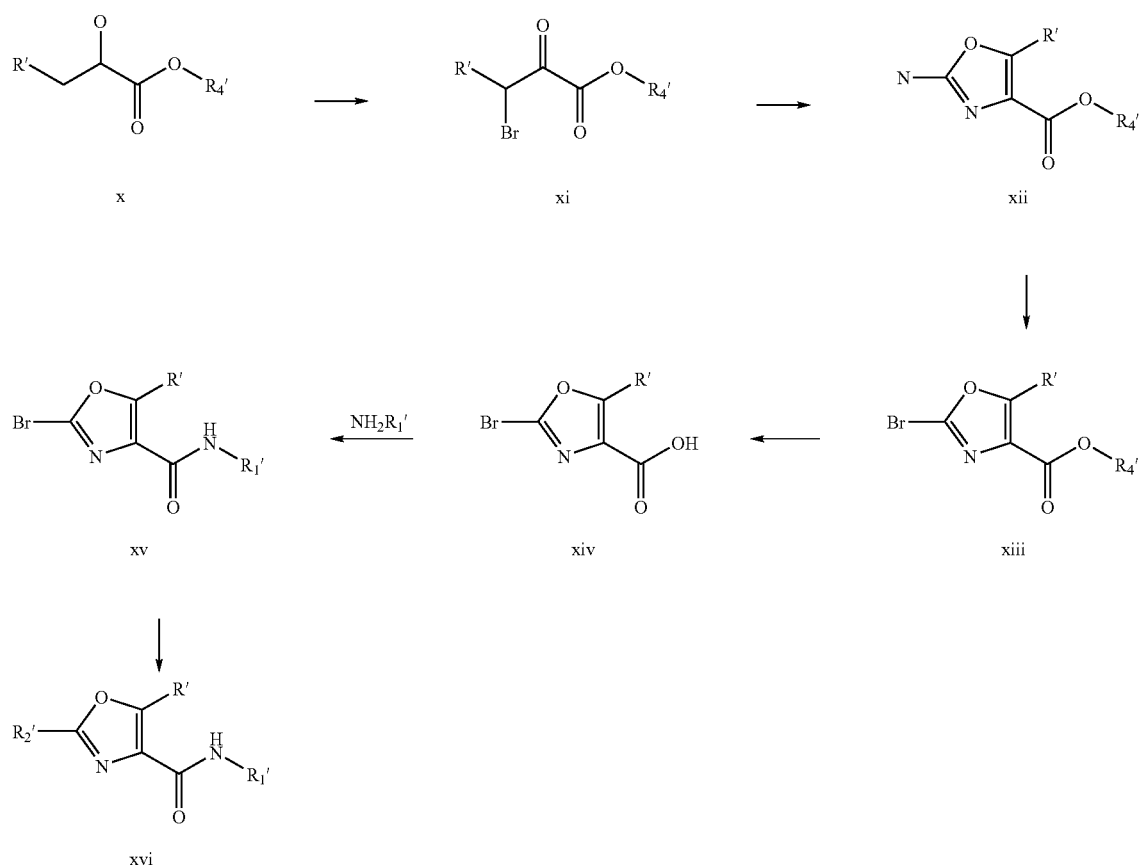

Scheme 3

As shown in Scheme 3, using a method similar to Plouvier et al (see B. Plouvier et al *Heterocycles* 32 693 (1991)), the 2-hydroxy-alkyl acid ester x, R' is lower alkyl, haloalkyl, alkoxy, thioalkoxy, haloalkoxy and $R_4'$ is lower alkyl, preferably methyl or ethyl, can be reacted with N-bromosuccimide onate ester in the presence of a base, typically an aqueous solution of sodium carbonate, in an appropriate solvent, typically, DME, DMF or toluene, with a catalytic amount of palladium, typically $Pd[PPh_3]_4$, to yield xiv, where $R_2'$ is aryl, substituted aryl, heteroaryl, substituted heteroaryl.

Scheme 4

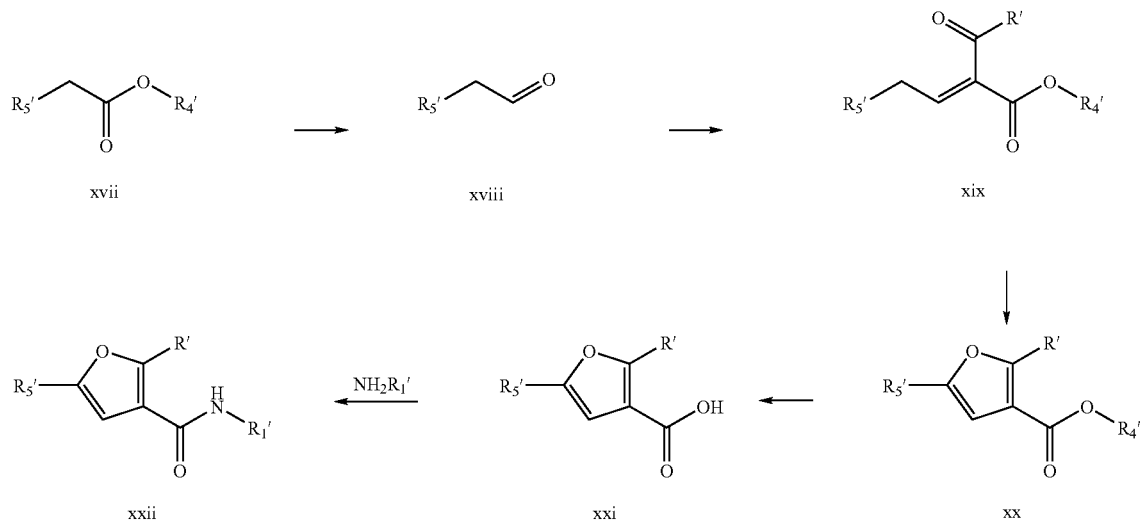

As shown in Scheme 4, ester xvii, where $R_4'$ is lower alkyl, preferably methyl or ethyl, and $R_5'$ is alkyl, branched alkyl, cycloalkyl or cycloheteroalkyl, can be reduced with various reducing agents, preferably DIBAL, to yield aldehyde xviii. Using a method similar to Kretchmer and Laiter (see R. A. Kretchmer and R. A. Laitar *J. Org. Chem.* 43 4596 (1978)), aldehyde xviii can be reacted with ethyl acetoacetate and a weak base, such as piperidine, to give xix. Upon heating with NBS in $CCl_4$ and distillation, xix yields substituted furan xx.

The substituted ester xx can be can be hydrolyzed by heating with a strong base, typically sodium hydroxide in an aqueous/organic mixed solvent, preferred is methanol, to give the 3-furoic acid xxi.

Furoic acid xxi can be reacted to form amides with various amines, where $R_1'$ is aryl, substituted aryl, heteroaryl, substituted heteroaryl, cycloalkyl or cycloheteroalkyl. Various standard amide bond forming conditions, as practiced by those skilled in the art, may be used. Typically xxi and an amine $NH_2R_1'$, in an appropriate solvent, may be treated with a base, such as triethyl amine, and an amide bond forming reagent such as BOP, PyBroP or EDCI and HOBT to yield amide xxii.

-continued

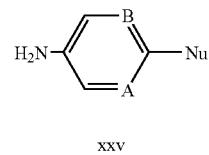

As shown in Scheme 5, commercially available nitro aryl halide xxiii, where A and B can be CH or N and X is F, Cl or Br, can be treated with a nucleophile, typically an amine or an alcohol, and a neutralizing base, typically $Et_3N$, in an appropriate solvent, typically dichloromethane or N,N-dimethylformamide with or without heating to yield the corresponding substituted nitro aryl xxiv, where Nu can be a substituted or unsubstituted cyclic amine, such as morpholin, thiomorpholin, pyrrolidine, piperidine, mono or disubstituted amine, amino acid or an alkoxy group. The nitro group in compound xxiv can be reduced in an appropriate solvent, typically ethyl acetate or methanol under pressure of hydrogen, typically 50 psi, in presence of a catalyst; typically 10% palladium on carbon, to give substituted aniline xxv.

Scheme 5

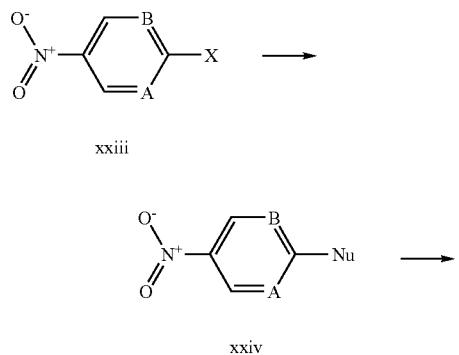

Scheme 6

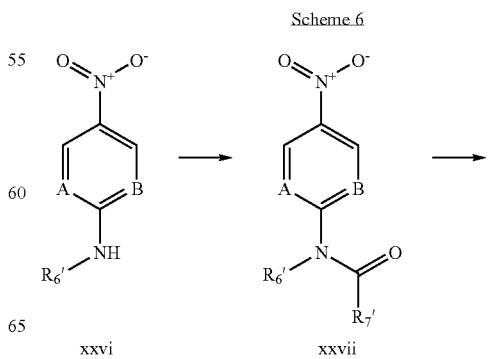

-continued

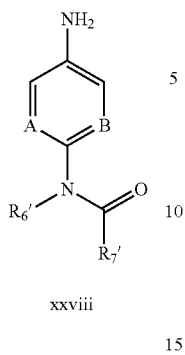

xxviii

As shown in Scheme 6, the mono substituted nitro aryl aniline xxvi, prepared according to the procedure described in Scheme 5, where $R_6'$ is lower alkyl, was acylated with an acylating agent, typically an acid chloride or an anhydride, in an appropriate solvent, typically pyridine, in presence of a catalytic amount of 4-dimethylaminopyridine with heating to give N-alkyl-4 nitro-aryl-amide xxvii, where $R_7'$ is lower alkyl. The nitro group in amide xxvii is reduced in an appropriate solvent, typically ethyl acetate or methanol under pressure of hydrogen, typically 50 psi, in presence of a catalyst; typically 10% palladium on carbon, to give aniline xxviii.

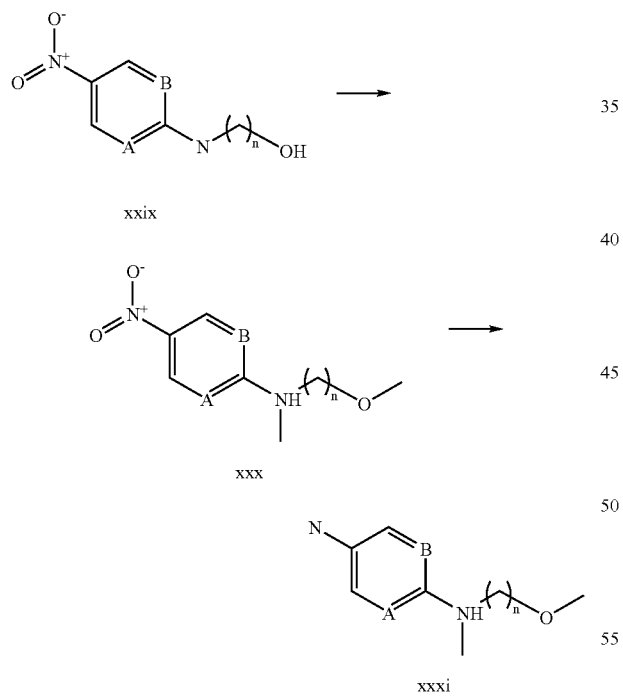

As shown in Scheme 7, compound xxix, prepared according to the procedure described in Scheme 5, can be treated with a base, typically sodium hydride and an alkylating agent, typically alkyl iodide in an appropriate solvent, typically N,N-dimethylformamide, to give N and/or O alkylated nitro compound xxx, which again can be reduced under pressure of hydrogen, typically 50 psi, in presence of a catalyst, typically 10% palladium on carbon, to give aniline xxxi.

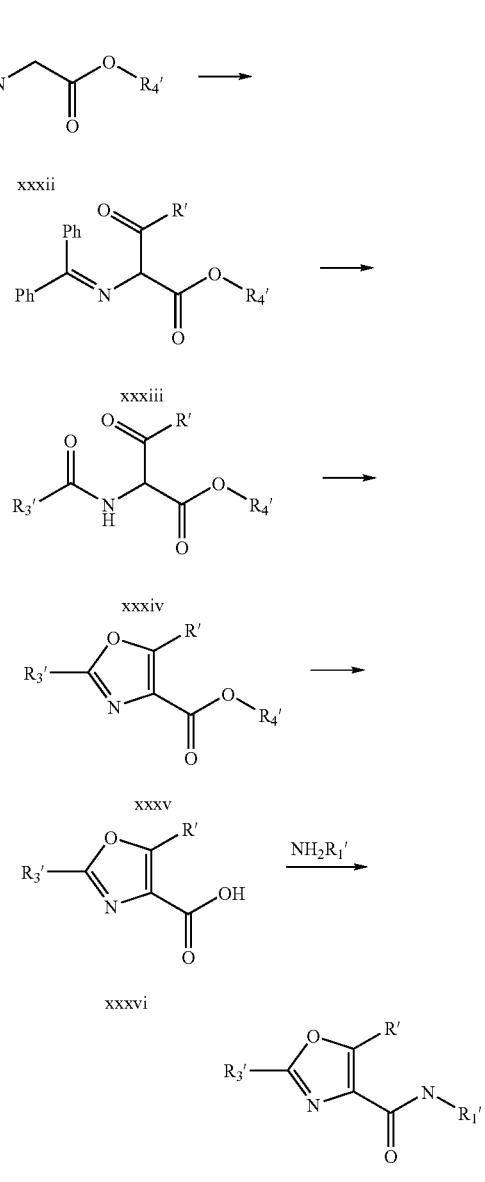

As shown in Scheme 8, oxazole compound xxxv can be prepared according to the procedure described in *Org. Lett*, 2003, 5 (24), 4567. Compound xxxii, commercially available or prepared according to the procedure described in *Bioorg. Med. Chem. Lett.* 2001, 11 (15), 1975, where $R_4'$ is lower alkyl, benzyl or other protecting groups, can be treated with a strong base, typically lithium bis(trimethylsilyl)amide, and an anhydride or an acid chloride, where R' can be a lower alkyl, cycloalkyl or cycloheteroalkyl, in an appropriate solvent, typically tetrahydrofuran, to give the keto ester xxxiii. The diphenyl imine xxxiii can be hydrolyzed with 2 N HCl aqueous solution in THF to give an amine HCl salt which can be acylated with an acid chloride or an anhydride in presence of pyridine in an appropriate solvent, typically dichloromethane to give compound xxxiv, where $R_3'$ is aryl, substituted aryl, heteroaryl, substituted heteroaryl, alkyl, or cycloalkyl. The oxazole ring can be generated by mixing compound xxxiv, triphenylphosphine and iodine in tetrahydrofuran with cooling. The oxazole ester xxxv can be hydrolyzed by treating with a base, typically lithium hydroxide in an aqueous/organic mixed solvent to give the oxazole-4-carboxylic acid xxxvi.

The acid xxxvi can be reacted to form amides with various amines, where $R_1'$ is aryl, substituted aryl, heteroaryl, substituted heteroaryl, cycloalkyl or cycloheteroalkyl. Various standard amide bond forming conditions, as practiced by those skilled in the art, may be used. Typically, the acid xxxvi and an amine $NH_2R_1'$, in an appropriate solvent, may be treated with a base, such as triethyl amine, and an amide bond forming reagent such as BOP, PyBrop, or EDCI and HOBT to yield amide xxxvii.

Scheme 9

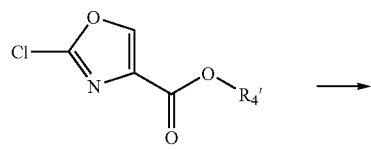

xxxviii

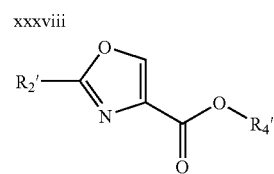

xxxix

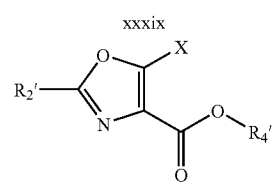

xxxx $\xrightarrow{NH_2R_1'}$

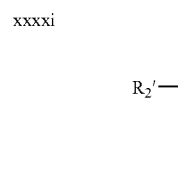

xxxxi stituted arylboronic acid or boronate ester in the presence of a base, typically an aqueous solution of sodium carbonate, in an appropriate solvent, typically, DME, DMF or Toluene, with a catalytic amount of palladium, typically $Pd(PPh_3)_4$, to yield xxxix, where $R_2'$ is aryl, substituted aryl, heteroaryl, or substituted heteroaryl. The oxazole ester xxxix can be chlorinated or brominated at C5 position with 1-chloro-pyrrolidine 2,5-dione or 1-bromo-pyrrolidine 2,5-dione by heating up to 90° C. in chloroform in presence of a catalytic amount of concentrated sulfuric acid to yield compound xxxx. The ester xxxx can be hydrolyzed by treating with a base, typically lithium hydroxide in an aqueous/organic mixed solvent to give the oxazole-4-carboxylic acid xxxxi.

Acid xxxxi can be reacted to form amides with various amines, where $R_1'$ is aryl, substituted aryl, heteroaryl, substituted heteroaryl, cycloalkyl or cycloheteroalkyl. Various standard amide bond forming conditions, as practiced by those skilled in the art, may be used. Typically, acid xxxxi and an amine $NH_2R_1'$, in an appropriate solvent, may be treated with a base, such as triethyl amine, and an amide bond forming reagent such as BOP, PyBrop, or EDCI and HOBT to yield amide xxxvii.

Scheme 10

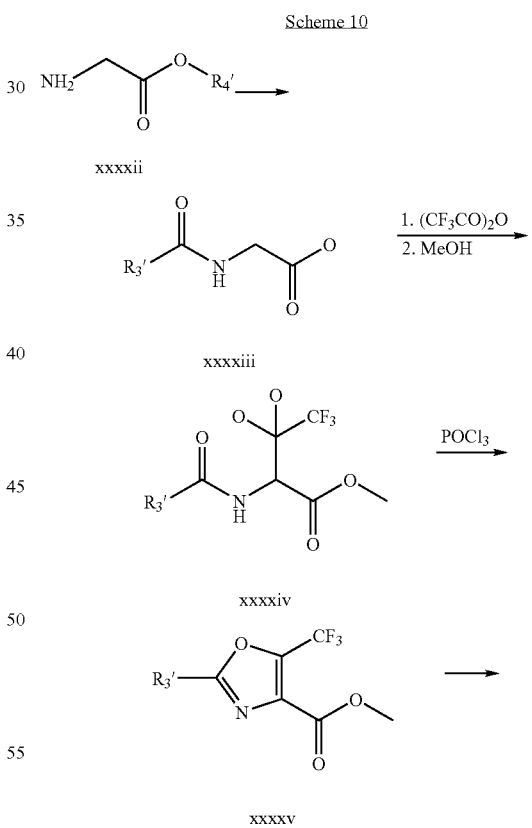

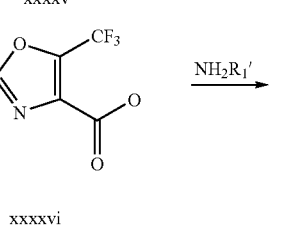

xxxxvi

Scheme 9 describes general synthesis of oxazole amide xxxvii bearing a halogen group at C-5. Using standard palladium catalyzed "cross coupling" procedures, 2-chloro-oxazole-4-carboxylic acid alkyl ester, where $R_4'$ is a lower alkyl, preferably methyl or ethyl, prepared according to the procedure described in *J. Med. Chem.* 1971, 14 (11), 1075; *Org. Lett.* 2002, 4 (17), 2905 and *J. Org. Chem.* 1977, 42, 2429, can be heated with a commercially available substituted or unsub- -continued

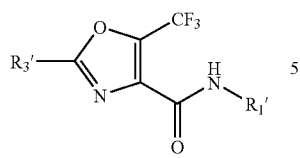

xxxxvii

Scheme 10 describes an alternative synthesis of oxazole amide xxxxvii bearing trifluoromethyl at C-5 position. The glycine ester, where $R_4'$ is lower alkyl, preferably methyl or ethyl, was acylated with an acylating agent, typically an acid chloride or an anhydride, where $R_3'$ is aryl, substituted aryl, heteroaryl, substituted heteroaryl, alkyl, or cycloalkyl. After acylation, the ester can be hydrolyzed by treating with a base, typically lithium hydroxide, in an aqueous/organic solvent, preferred is methanol, to give acid xxxxiii. To the solution of acid xxxxiii in acetone was added excess of trifluoroacetic anhydride with cooling to give a stable ketone hydrate, which was then refluxed in methanol for 30 min to give ketone hydrate methyl ester xxxxiv. Compound xxxxiv upon heating with phosphorus oxychloride cyclizes to yield substituted oxazole ester xxxxv, which was again hydrolyzed with a base, typically lithium hydroxide, in an aqueous/organic mixed solvent, preferred is methanol, to give oxazole acid xxxxvi.

Oxazole acid xxxxvi can be reacted to form amides with various amines, where $R_1'$ is aryl, substituted aryl, heteroaryl, substituted heteroaryl, cycloalkyl or cycloheteroalkyl. Various standard amide bond forming conditions, as practiced by those skilled in the art, may be used. Typically, acid xxxxvi and an amine $NH_2R_1'$, in an appropriate solvent, may be treated with a base, such as triethyl amine, and an amide bond forming reagent such as BOP, PyBrop, or EDCI and HOBT to yield amide xxxxvii.

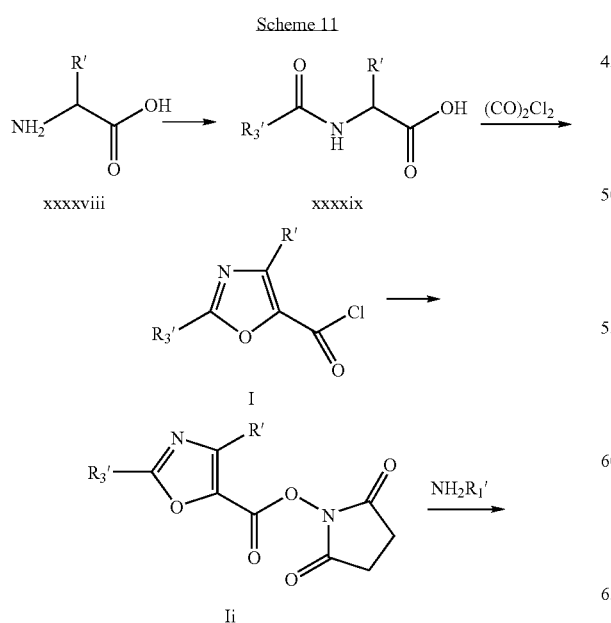

-continued

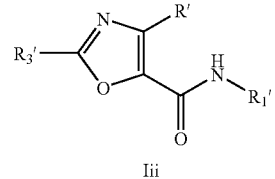

Iii

As shown in Scheme 11, commercially available amino acid xxxxviii, where R' can be lower alkyl, cycloalkyl, or cycloheteroalkyl, can be acylated with an acylating agent, typically an acid chloride or an anhydride, according to the procedure described in *Int. J. Peptide Protein Res.* 1989, 33, 353. Using a procedure described in *J. Chem. Soc. Chem. Commun.* 1995, 2335, acid xxxxix can be treated with excess oxalyl chloride with heating in a solvent such as tetrahydrofuran to give cyclized oxazole l, which was directly converted into active ester li by heating with 1-hydroxy-pyrrolidine-2,5-dione and a base, such as triethylamine, in acetonitrile.

Oxazole acid li can be reacted with various amines to form amides lii by heating in an appropriate solvent, typically acetonitrile, where $R_1'$ is aryl, substituted aryl, heteroaryl, substituted heteroaryl, cycloalkyl or cycloheteroalkyl.

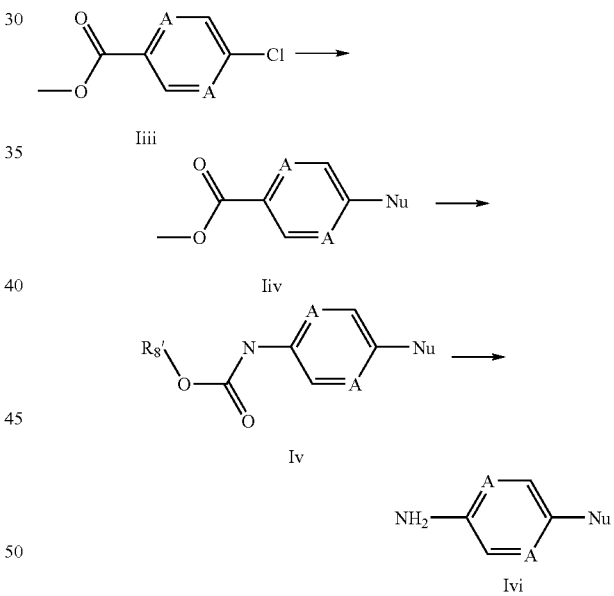

As shown in Scheme 12, aromatic heterocyclic amines lvi can be prepared through a Curtius rearrangement reaction. Commercially available aryl halide carboxylic acid methyl ester liii (where X can be nitrogen) is reacted with a nucleophile, Nu, typically an amine or an alcohol, in the presence of a base such as triethyl amine. The nucleophilic amine can be non-cyclic, cyclic with or without substitution, or heterocyclic. The resulting ester liv can be saponified to give the corresponding carboxylic acid, which is transformed to an isocyanate intermediate through Curtius rearrangement reaction in the presence of diphenylphosphoryl azide and appropriate base such as triethyl amine. The isocyanate intermediate can be reacted with alcohols (where $R_8'$ can be tert-butyl or benzyl) to generate the corresponding carbamate lv.

Finally the tert-butyl or benzyl carbamate can be deprotected under acidic conditions such as trifluroacetic acid or under palladium catalyzed hydrogenation to generate the desired aromatic heterocyclic amines lvi.

Scheme 13

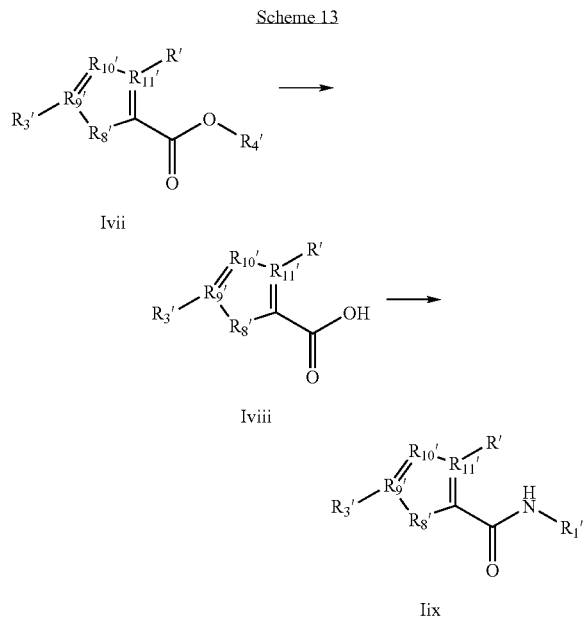

lvii lviii lix

As shown in Scheme 13, amides lix, where $R_3'$ is aryl, substituted aryl, heteroaryl, substituted heteroaryl, alkyl, or cycloalkyl, where $R_1'$ can be aryl, substituted aryl, heteroaryl, substituted heteroaryl, cycloalkyl or cycloheteroalkyl, R' can be lower alkyl, cycloalkyl, cycloheteroalkyl or null, and $R_3'$ can be aryl, substituted aryl, heteroaryl, substituted heteroaryl, alkyl, or cycloalkyl, can be prepared from commercially available substituted aromatic acids lviii, where $R_8'$, $R_9'$, $R_{10}'$, and $R_{11}'$ can independently be N, C, or S, also prepared from commercially available esters lvii, where $R_4'$ is lower alkyl, preferably methyl or ethyl, following hydrolysis, and various amines. Various standard amide bond forming conditions, as practiced by those skilled in the art, may be used. Typically, acid lviii and an amine $NH_2R_1'$, in an appropriate solvent, may be treated with a base, such as triethyl amine, and an amide bond forming reagent such as BOP, PyBrop, or EDCI and HOBT to yield amide lix.

In the practice of the method of the present invention, an effective amount of any one of the compounds of this invention or a combination of any of the compounds of this invention or a pharmaceutically acceptable salt thereof, is administered via any of the usual and acceptable methods known in the art, either singly or in combination. The compounds or compositions can thus be administered orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form or solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

Useful pharmaceutical carriers for the preparation of the compositions hereof, can be solids, liquids or gases; thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

The dose of a compound of the present invention depends on a number of factors, such as, for example, the manner of administration, the age and the body weight of the subject, and the condition of the subject to be treated, and ultimately will be decided by the attending physician or veterinarian. Such an amount of the active compound as determined by the attending physician or veterinarian is referred to herein, and in the claims, as a "therapeutically effective amount". For example, the dose of a compound of the present invention is typically in the range of about 1 to about 1000 mg per day. Preferably, the therapeutically effective amount is in an amount of from about 1 mg to about 500 mg per day The invention will now be further described in the Examples below, which are intended as an illustration only and do not limit the scope of the invention.

EXAMPLES

The Examples which follow are for purposes of illustration and are not intended to limit the invention in any way.

General Methods: Melting points were taken on a Thomas-Hoover apparatus and are uncorrected. Optical rotations were determined with a Perkin-Elmer model 241 polarimeter. 1H-NMR spectra were recorded with Varian XL-200, Mercury-300 or Unityplus 400 MHz spectrometers. Tetramethylsilane (TMS) may be used as internal standard. Electron impact (EI, 70 ev) and fast atom bombardment (FAB) mass spectra were taken on VG Autospec or VG 70E-HF mass spectrometers. Silica gel used for column chromatography was Mallinkrodt SiliCar 230-400 mesh silica gel for flash chromatography; columns were run under a 0-5 psi head of nitrogen to assist flow. Thin layer chromatograms were run on glass thin layer plates coated with silica gel as supplied by E. Merck (E. Merck # 1.05719) and were visualized by viewing under 254 nm UV light in a view box, by exposure to $I_2$ vapor, or by spraying with either phosphomolybdic acid (PMA) in aqueous ethanol, or after exposure to Cl$_2$, with a 4,4'-tetramethyldiaminodiphenylmethane reagent prepared according to E. Von Arx, M. Faupel and M Brugger, *J. Chromatography*, 1976, 220, 224-228.

Reversed phase high pressure liquid chromatography (RP-HPLC) was carried out using a Rainin HPLC employing a 41.4×300 mm, 8 μm, Dynamax™ C-18 column at a flow of 49 mL/min employing a gradient of acetonitrile:water (each containing 0.75% TFA) typically from 5 to 95% acetonitrile over 35-40 min. HPLC conditions are typically described in the format (5-95-35-214); this refers to a linear gradient of from 5% to 95% acetonitrile in water over 35 min while monitoring the effluent with a UV detector at a wavelength of 214 nm.

Preparative supercritical fluid chromatography (SFC) was performed on Berger MultiGram II Supercritical Fluid Chromatography system (Model SD-1) from Mettler-Toledo AutoChem Berger Instruments, Newark, Del., USA. The system consisted of an automatic liquid injection system with a DAICEL AD chiral column, 5 mL loop used to make injections and a thermal control module (TCM) used to control column temperature. Chromatographic conditions: SFC separations were performed at a temperature of 30° C., a flow rate of 70 mL/min, and CO$_2$ pressure of 100 bar. Knauer variable wavelength UV detector (supplied by Mettler-Toledo) with high pressure flow cell was used for SFC detection. Detection in SFC was performed by measurement of UV absorbance at 220 nm.

Methylene chloride (dichloromethane), 2-propanol, DMF, THF, toluene, hexane, ether, and methanol, were Fisher or Baker reagent grade and were used without additional purification except as noted, acetonitrile was Fisher or Baker HPLC grade and was used as is.

Definitions as Used Herein

DGAT is diacylglycerol:acyl CoA O-acyltransferase,

THF is tetrahydrofuran,

DMF is N,N-dimethylformamide,

DMA is N,N-dimethylacetamide,

DMSO is dimethylsulfoxide,

DCM is dichloromethane,

DME is dimethoxyethane,

MeOH is methanol,

EtOH is ethanol,

NaOH is sodium hydroxide,

NBS is N-bromosuccinimide,

TFA is 1,1,1-trifluoroacetic acid,

HOBT is 1-hydroxybenzotriazole,

PyBroP is bromotripyrrolidinophosphonium hexafluorophosphate,

EDCI is 1-[3-(dimethylamino)propyl]-3-ethylcarbodiimide hydrochloride,

DIPEA is diisopropylethylamine, brine is saturated aqueous sodium chloride solution, DAG is 1,2-dioleoyl-sn-glycerol, TLC is thin layer chromatography, RP HPLC is reversed phase high performance liquid chromatography, APCI-MS is atmospheric pressure chemical ionization mass spectrometry, ES-MS is electrospray mass spectrometry, LCMS is liquid chromatography mass spectrometry, RT is room or ambient temperature.

Silica gel chromatography on Biotage columns refers to use of a flash chromatography system supplied by the Biotage Division of the Dyax Corporation employing prepacked 40 g (40 s columns), 90 g (40 m columns) or 800 g (75 m columns). Elution is carried out with hexane-ethyl acetate mixtures under 10-15 psi nitrogen pressure.

Part I

Intermediates

Preparation of 6-morpholin-4-yl-pyridin-3-ylamine

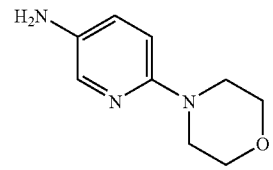

A mixture of 2-chloro-5-nitro-pyridine (5 g, 31 mmol), morpholine (13 mL, 155 mmol), and triethylamine (10 mL) in dichloromethane (30 mL) was stirred at room temperature for 3 hr. After the reaction, the reaction mixture was mixed with water, and two layers were separated. The aqueous layer was extracted with CH$_2$Cl$_2$ two times. Organic layers were collected, combined, washed with brine, dried over sodium sulfate, filtered, and concentrated to give 4-(5-nitro-pyridin-2-yl)-morpholine (6.48 gm, 100%) as a yellow solid. LCMS calcd for C9H11N3O3 (m/e) 209, obsd 210 (M+H).

The solution of 4-(5-nitro-pyridin-2-yl)-morpholine (1.5 g, 7.18 mmol) in ethyl acetate (20 mL) in the presence of 10% palladium on carbon (0.75 g) was shaken under the hydrogen with a pressure of 50 psi at room temperature for 3 hr. After the reaction, the reaction mixture was filtered through a plug of celite and the filtration pad was washed with ethyl acetate. The organic layer was collected, concentrated, and dried to give 6-morpholin-4-yl-pyridin-3-ylamine (1.11 g, crude) as a light red solid, which was directly used in the next step reaction without further purification. LCMS calcd for C9H14N3O (m/e) 179, obsd 180 (M+H).

Preparation of 2-morpholin-4-yl-pyrimidin-5-ylamine

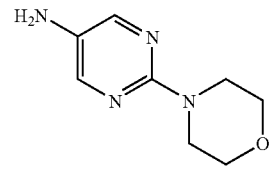

With a method similar to that used for the preparation of 6-morpholin-4-yl-pyridin-3-ylamine above, 2-morpholin-4-yl-pyrimidin-5-ylamine was prepared from 2-chloro-5-nitropyrimidine and morpholine. LCMS calcd for C8H12N4O (m/e) 180, obsd 181 (M+H).

Preparation of 6-thiomorpholin-4-yl-pyridin-3-ylamine

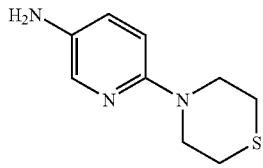

With a method similar to that used for the preparation of 6-morpholin-4-yl-pyridin-3-ylamine above, 6-thiomorpholin-4-yl-pyridin-3-ylamine was prepared from 2-chloro-5-nitro-pyridine and thiomorpholine. LCMS calcd for C9H13N3S (m/e) 195, obsd 196 (M+H).

Preparation of N-[1-(5-amino-pyridin-2-yl)-pyrrolidin-3-yl]-N-methyl-acetamide

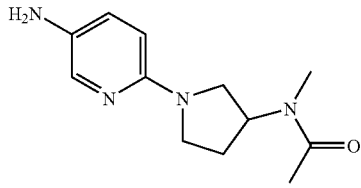

With a method similar to that used for the preparation of 6-morpholin-4-yl-pyridin-3-ylamine above, N-[1-(5-amino-pyridin-2-yl)-pyrrolidin-3-yl]-N-methyl-acetamide was prepared from 2-chloro-5-nitro-pyridine and N-methyl-N-pyrrolidin-3-yl-acetamide. LCMS calcd for C12H18N4O (m/e) 234, obsd 235 (M+H).

Preparation of 2-(5-amino-pyridin-2-ylamino)-ethanol

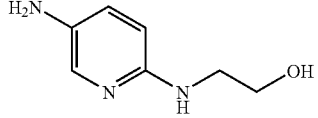

With a method similar to that used for the preparation of 6-morpholin-4-yl-pyridin-3-ylamine above, 2-(5-amino-pyridin-2-ylamino)-ethanol was prepared from 2-chloro-5-nitro-pyridine and 2-amino-ethanol. LCMS calcd for C7H11N3O (m/e) 153, obsd 154 (M+H).

Preparation of 2-(2-methoxy-ethyl)-pyridine-2,5-diamine

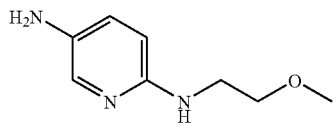

With a method similar to that used for the preparation of 6-morpholin-4-yl-pyridin-3-ylamine above, 2-(2-methoxy-ethyl)-pyridine-2,5-diamine was prepared from 2-chloro-5-nitro-pyridine and 2-methoxy-ethylamine. LCMS calcd for C8H13N3O (m/e) 167, obsd 168 (M+H).

Preparation of $N^2$-(2-methoxy-ethyl)-$N^2$-methyl-pyridine-2,5-diamine

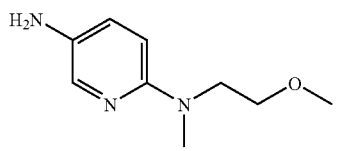

With a method similar to that used for the preparation of 6-morpholin-4-yl-pyridin-3-ylamine above, $N^2$-(2-methoxy-ethyl)-$N^2$-methyl-pyridine-2,5-diamine was prepared from 2-chloro-5-nitro-pyridine and (2-methoxy-ethyl)-methyl-amine. LCMS calcd for C9H15N3O (m/e) 181, obsd 182 (M+H).

Preparation of 6-(2-methoxy-ethoxy)-pyridin-3-ylamine

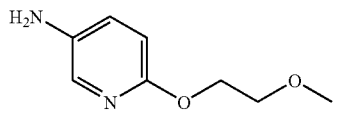

With a method similar to that used for the preparation of 6-morpholin-4-yl-pyridin-3-ylamine above, 6-(2-methoxy-ethoxy)-pyridin-3-ylamine was prepared from 2-chloro-5-nitro-pyridine and 2-methoxy-ethanol. LCMS calcd for C8H12N2O (m/e) 168, obsd 169 (M+H).

Preparation of 2-[(5-amino-pyridin-2-yl)-methyl-amino]-ethanol

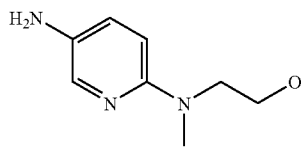

With a method similar to that used for the preparation of 6-morpholin-4-yl-pyridin-3-ylamine above, 2-[(5-amino-pyridin-2-yl)-methyl-amino]-ethanol was prepared from 2-chloro-5-nitro-pyridine and 2-methylamino-ethanol. LCMS calcd for C8H13N3O (m/e) 167, obsd 168 (M+H).

Preparation of N²-(3-methoxy-propyl)-N²-methyl-pyridine-2,5-diamine

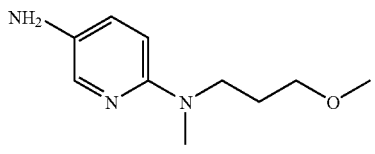

With a method similar to that used for the preparation of 6-morpholin-4-yl-pyridin-3-ylamine above, N²-(3-methoxy-propyl)-N²-methyl-pyridine-2,5-diamine was prepared from 2-chloro-5-nitro-pyridine and (3-methoxy-propyl)-methyl-amine. LCMS calcd for C10H17N3O (m/e) 195, obsd 196 (M+H).

Preparation of N²-(3-methoxy-propyl)-pyridine-2,5-diamine

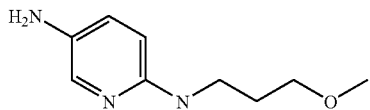

With a method similar to that used for the preparation of 6-morpholin-4-yl-pyridin-3-ylamine above, N²-(3-methoxy-propyl)-pyridine-2,5-diamine was prepared from 2-chloro-5-nitro-pyridine and 3-methoxy-propylamine. LCMS calcd for C9H15N3O (m/e) 181, obsd 182 (M+H).

Preparation of N²-ethyl-N²-(2-methoxy-ethyl)-pyridine-2,5-diamine

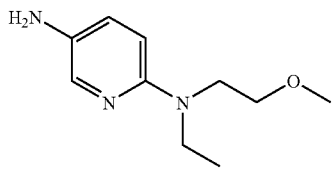

With a method similar to that used for the preparation of 6-morpholin-4-yl-pyridin-3-ylamine above, N²-ethyl-N²-(2-methoxy-ethyl)-pyridine-2,5-diamine was prepared from 2-chloro-5-nitro-pyridine and ethyl-(2-methoxy-ethyl)-amine. LCMS calcd for C10H17N3O (m/e) 195, obsd 196 (M+H).

Preparation of N²-butyl-N²-methyl-pyridine-2,5-diamine

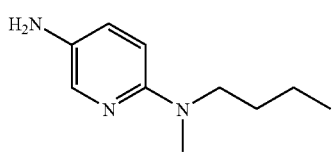

With a method similar to that used for the preparation of 6-morpholin-4-yl-pyridin-3-ylamine above, N²-butyl-N²-methyl-pyridine-2,5-diamine was prepared from 2-chloro-5-nitro-pyridine and butyl-methyl-amine. LCMS calcd for C10H17N3 (m/e) 179, obsd 180 (M+H).

Preparation of N²-methyl-N²-propyl-pyridine-2,5-diamine

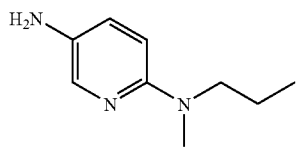

With a method similar to that used for the preparation of 6-morpholin-4-yl-pyridin-3-ylamine above, N²-methyl-N²-propyl-pyridine-2,5-diamine was prepared from 2-chloro-5-nitro-pyridine and methyl-propyl-amine. LCMS calcd for C9H15N3 (m/e) 165, obsd 166 (M+H).

Preparation of N²-ethyl-N²-methyl-pyridine-2,5-diamine

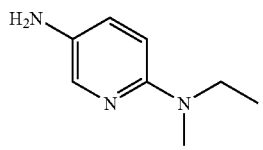

With a method similar to that used for the preparation of 6-morpholin-4-yl-pyridin-3-ylamine above, N²-ethyl-N²-methyl-pyridine-2,5-diamine was prepared from 2-chloro-5-nitro-pyridine and ethyl-methyl-amine. LCMS calcd for C8H13N3 (m/e) 151, obsd 152 (M+H).

Preparation of N²-ethyl-pyridine-2,5-diamine

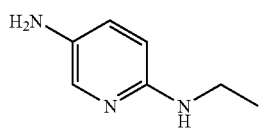

With a method similar to that used for the preparation of 6-morpholin-4-yl-pyridin-3-ylamine above, N²-ethyl-pyridine-2,5-diamine was prepared from 2-chloro-5-nitro-pyridine and ethyl-amine. LCMS calcd for C7H11N3 (m/e) 137, obsd 138 (M+H).

Preparation of N²,N²-diethyl-pyridine-2,5-diamine

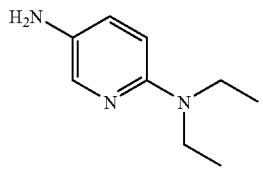

With a method similar to that used for the preparation of 6-morpholin-4-yl-pyridin-3-ylamine above, N²,N²-diethyl-pyridine-2,5-diamine was prepared from 2-chloro-5-nitro-pyridine and diethyl-amine. LCMS calcd for C9H15N3 (m/e) 165, obsd 166 (M+H).

Preparation of $N^2$-isopropyl-$N^2$-methyl-pyridine-2,5-diamine

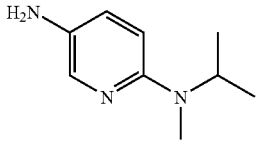

With a method similar to that used for the preparation of 6-morpholin-4-yl-pyridin-3-ylamine above, $N^2$-Isopropyl-$N^2$-methyl-pyridine-2,5-diamine was prepared from 2-chloro-5-nitro-pyridine and isopropyl-methyl-amine. LCMS calcd for C9H15N3 (m/e) 165, obsd 166 (M+H).

Preparation of $N^2,N^2$-dimethyl-pyridine-2,5-diamine

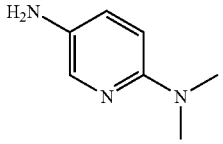

A mixture of 2-chloro-5-nitro-pyridine (500 mg, 3.15 mmol), in DMF (2 mL) was added dropwise to a suspension of NaH (151 mg, 6.31 mmol) in DMF (2 mL). The reaction mixture was stirred at room temperature for one hour then heated to 55° C. overnight. The reaction mixture was then poured into ice water, extracted with EtOAc, washed with brine, dried over sodium sulfate, filtered and concentrated to give dimethyl-(5-nitro-pyridin-2-yl)-amine as a yellow solid. LCMS calcd for C7H11N3 (m/e) 137, obsd 138 (M+H).

A solution of dimethyl-(5-nitro-pyridin-2-yl)-amine (100 mg, 0.47 mmol) and 10% palladium on carbon (0.05 g) in methanol (5 mL) was shaken under 50 psi hydrogen atmospheres at room temperature for 3 h. The reaction mixture was then filtered through a plug of celite and the filtration pad was washed with ethyl acetate. The organic layers were collected, concentrated, and dried to give $N^2,N^2$-dimethyl-pyridine-2,5-diamine (90 mg crude) as a light red oil, which was directly used in the next step without further purification.

Preparation of $N^2$-cyclopentyl-pyridine-2,5-diamine

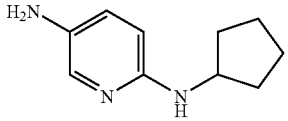

To a 20 mL vial containing cyclopentylamine (300 mg, 3.53 mmol) was added DMF (5 mL), 2-chloro-5-nitro-pyridine (559 mg, 3.53 mmol), and the TEA (0.98 mL). The vessel was purged with argon, sealed, and heat by microwave at 200° C. for 5 min (Personal Chemistry, Emrys Optimizer). The reaction mixture was concentrated, diluted with water (100 mL) and extracted with ethyl acetate. The organic layer was washed with saturated sodium bicarbonate (100 mL) and brine (100 mL), dried over sodium sulfate, and evaporated to give cyclopentyl-(5-nitro-pyridin-2-yl)-amine. LCMS calcd. $C_{10}H_{13}N_3O_2$ (m/e) 207, observed 208 (M+H). This intermediate nitropyridyl compound was transferred to a PARR vessel with MeOH (5 mL), Pd/C (10%) was added and the vessel was pressurized with $H_2$ at 55 psi and shaken for 2.5 hr. The mixture was then filtered through a bed of celite and concentrated to dryness twice from $CH_2Cl_2$. The purple black material was used immediately for amide coupling (LCMS calcd. for $C_{10}H_{15}N_3$ (m/e) 177, observed 178 (M+H).

Preparation of $N^2$-cyclohexyl-pyridine-2,5-diamine

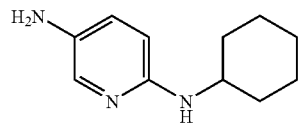

With a method similar to that used for the preparation of cyclopentyl-pyridine-2,5-diamine above, $N^2$-cyclohexyl-pyridine-2,5-diamine was prepared from 2-chloro-5-nitro-pyridine and cyclohexyl amine. LCMS for $C_{11}H_{17}N_3$ calculated (m/e) 191, observed 192 (M+H).

Preparation of $N^2$-cyclopropyl-pyridine-2,5-diamine

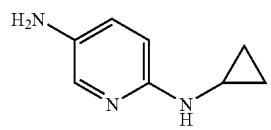

With a method similar to that used for the preparation of cyclopentyl-pyridine-2,5-diamine, $N^2$-cyclopropyl-pyridine-2,5-diamine was prepared from 2-chloro-5-nitro-pyridine and cyclopropyl amine. (LCMS calculated for $C_8H_{11}N_3$ (m/e) 149, observed 150 (M+H).

Preparation of $N^2$-cyclopropyl-$N^2$-methyl-pyridine-2,5-diamine

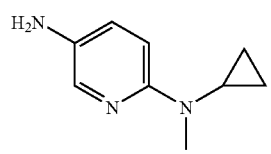

The intermediate, cyclopropyl-(5-nitro-pyridin-2-yl)-amine, from the above procedure, was methylated with methyl iodide. To a 2 mL microwave vial was added cyclopropyl-(5-nitro-pyridin-2-yl)-amine (146 mg, 0.812 mmol), DMF (2 mL), potassium carbonate (224 mg, 1.62 mmol), and the MeI (56 µl, 0.893 mmol). The mixture was heated by microwave for two 10 min increments at 200° C. using a Personal Chemistry, Emrys Optimizer. Then followed addition of another portion of MeI (56 µL, 0.893 mmol) microwave at 200° C. for 10 min and then conventional heating at 70° C. for 15 hr. At the end of this period a third addition of MeI (56 µL, 0.893 mmol) took place and the mixture was heated by microwave once more for 10 min at 200° C. The reaction mixture was then concentrated to dryness, suspended in ethyl acetate (100 mL) and washed with water (100 mL) two times and one time with brine. The aqueous layers were combined and extracted once with ethyl acetate (50 mL). The combined organic layer was washed once with brine (100 mL), concentrated, supported onto silica gel, and purified by flash chromatography using the Analogix system with a 12 g Silicycle silica gel column with increasing concentrations of ethyl acetate in hexanes (20 mL/min, equilibrate with 0%, 0 to 5 min: 0%; 5 to 25 min: 0 to 30%; 25-45 min: 30%). The appropriate fractions were collected and dried to afford 90 mg of cyclopropyl-methyl-(5-nitro-pyridin-2-yl)-amine, a yellow solid (yield 57%). LCMS calcd. for $C_9H_{11}N_3O_2$ (m/e) 193, observed 194 (M+H). This intermediate nitropyridyl compound was then reduced, as described in the preparation of cyclopentyl-pyridine-2,5-diamine above, to afford $N^2$-cyclopropyl-$N^2$-methyl pyridine-2,5-diamine. LCMS calcd. for $C_9H_{13}N_3$ (m/e) 163, observed 164 (M+H).

Preparation of $N^2$-cyclobutyl-$N^2$-methyl-pyridine-2,5-diamine

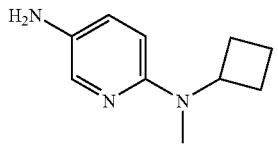

With a similar method used for the preparation of cyclopentyl-(5-nitro-pyridin-2-yl)-amine above cyclobutyl-(5-nitro-pyridin-2-yl)-amine was prepared from 2-chloro-5-nitro-pyridine and cyclobutyl amine. LCMS calcd. for C9H11N3O2 (m/e) 193, observed 194 (M+H). This intermediate nitropyridyl was then methylated and reduced to $N^2$-cyclobutyl-$N^2$-methyl pyridine-2,5-diamine with a method similar to the one described in the synthesis of $N^2$-cyclopropyl-$N^2$-methyl pyridine-2,5-diamine above. LCMS for $C_{10}H_{15}N_3$ calcd. (m/e) 177, observed 178 (M+H).

Preparation of $N^2$-cyclopropyl-$N^2$-methyl-pyrimidine-2,5-diamine

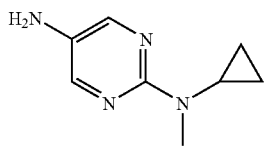

With a method similar to that used for the preparation of $N^2$-cyclopropyl-$N^2$-methyl pyridine-2,5-diamine above, $N^2$-cyclopropyl-$N^2$-methyl pyrimidine-2,5-diamine was prepared from 2-chloro-5-nitro-pyrimidine, cyclopropyl amine and methyl iodide. LCMS for $C_8H_{12}N_4$ calculated (m/e) 164, observed 165 (M+H).

Preparation of N-(2-methoxy-ethyl)-N-methyl-pyrimidine-2,5-diamine

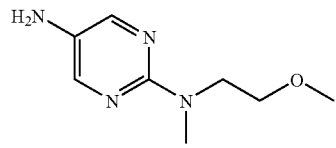

With a method similar to that used for the preparation of 6-morpholin-4-yl-pyridin-3-ylamine above, N-(2-methoxy-ethyl)-N-methyl-pyrimidine-2,5-diamine was prepared from 2-chloro-5-nitro-pyrimidine and (2-methoxy-ethyl)-methyl-amine. LCMS calcd for C8H14N4O (m/e) 182, obsd 183 (M+H).

Preparation of 6-((R)-2-methoxymethyl-pyrrolidin-1-yl)-pyridin-3-ylamine

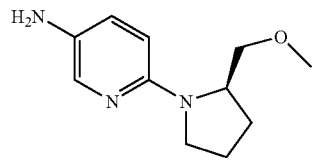

With a method similar to that used for the preparation of 6-morpholin-4-yl-pyridin-3-ylamine above, 6-((R)-2-methoxymethyl-pyrrolidin-1-yl)-pyridin-3-ylamine was prepared from 2-chloro-5-nitro-pyridine and (R)-2-methoxymethyl-pyrrolidine. LCMS calcd for C11H17N3O (m/e) 207, obsd 208 (M+H).

Preparation of [(S)-1-(5-amino-pyridin-2-yl)-pyrrolidin-2-yl]-methanol

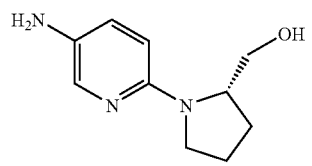

With a method similar to that used for the preparation of 6-morpholin-4-yl-pyridin-3-ylamine above, [(S)-1-(5-amino-pyridin-2-yl)-pyrrolidin-2-yl]-methanol was prepared from 2-chloro-5-nitro-pyridine and (S)-1-pyrrolidin-2-yl-methanol. LCMS calcd for C10H15N3O (m/e) 193, obsd 194 (M+H).

Preparation of 1-(5-amino-pyridin-2-yl)-pyrrolidin-3-ol

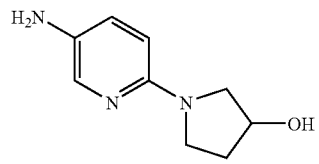

With a method similar to that used for the preparation of 6-morpholin-4-yl-pyridin-3-ylamine above, 1-(5-amino-pyridin-2-yl)-pyrrolidin-3-ol was prepared from 2-chloro-5-nitro-pyridine and pyrrolidin-3-ol. LCMS calcd for C9H13N3O (m/e) 179, obsd 180 (M+H).

Preparation of 5'-amino-3,4,5,6-tetrahydro-2H-[1,2'] bipyridinyl-3-ol

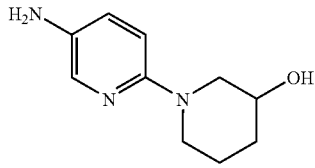

With a method similar to that used for the preparation of 6-morpholin-4-yl-pyridin-3-ylamine above, 5'-amino-3,4,5,6-tetrahydro-2H-[1,2']bipyridinyl-3-ol was prepared from 2-chloro-5-nitro-pyridine and piperidin-3-ol. LCMS calcd for C10H15N3O (m/e) 193, obsd 194 (M+H).

Preparation of 5'-amino-3,4,5,6-tetrahydro-2H-[1,2'] bipyridinyl-4-ol

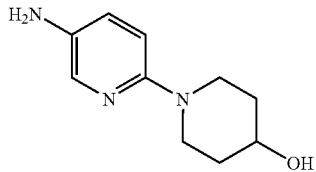

With a method similar to that used for the preparation of 6-morpholin-4-yl-pyridin-3-ylamine above, 5'-amino-3,4,5,6-tetrahydro-2H-[1,2']bipyridinyl-4-ol was prepared from 2-chloro-5-nitro-pyridine and piperidin-4-ol. LCMS calcd for C10H15N3O (m/e) 193, obsd 194 (M+H).

Preparation of (S)-2-(5-Amino-pyrimidin-2-ylamino)-propan-1-ol

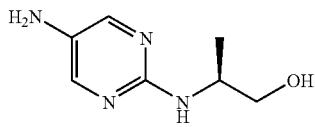

With a method similar to that used for the preparation of 6-morpholin-4-yl-pyridin-3-ylamine above, (S)-2-(5-amino-pyrimidin-2-ylamino)-propan-1-ol was prepared from 2-chloro-5-nitro-pyrimidine and 2-amino-propan-1-ol. LCMS calcd for C7H12N4O (m/e) 168, obsd 169 (M+H).

Preparation of (S)-1-(5-amino-pyridin-2-yl)-pyrrolidin-3-ol

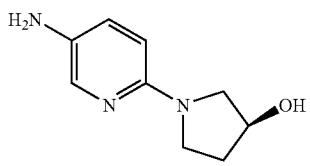

With a method similar to that used for the preparation of 6-morpholin-4-yl-pyridin-3-ylamine above, 1-(5-amino-pyridin-2-yl)-pyrrolidin-3-ol was prepared from 2-chloro-5-nitro-pyridine and (S)-pyrrolidin-3-ol. LCMS calcd for C9H13N3O (m/e) 179, obsd 180 (M+H).

Preparation of 2-(5-amino-pyridin-2-ylamino)-2-methyl-propan-1-ol

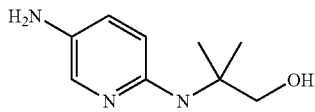

With a method similar to that used for the preparation of 6-morpholin-4-yl-pyridin-3-ylamine above, 2-(5-amino-pyridin-2-ylamino)-2-methyl-propan-1-ol was prepared from 2-chloro-5-nitro-pyridine and 2-amino-2-methyl-propan-1-ol. LCMS calcd for C9H15N3O (m/e) 181, obsd 182 (M+H).

Preparation of [(5-amino-pyridin-2-yl)-methyl-amino]-acetic acid methyl ester

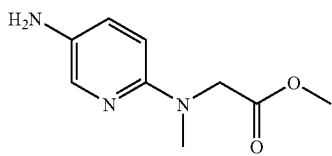

With a method similar to that used for the preparation of 6-morpholin-4-yl-pyridin-3-ylamine above, [(5-amino-pyridin-2-yl)-methyl-amino]-acetic acid methyl ester was prepared from 2-chloro-5-nitro-pyridine and methylamino-acetic acid methyl ester (reaction was heated up to 100° C. in DMF). LCMS calcd for C9H13N3O2 (m/e) 195, obsd 196 (M+H).

Preparation of 2-[(5-amino-pyridin-2-yl)-methyl-amino]-N,N-dimethyl-acetamide

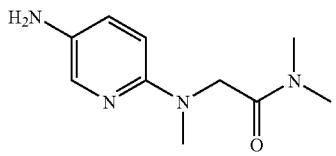

With a procedure similar to that used for the preparation of 6-morpholin-4-yl-pyridin-3-ylamine above, 2-[(5-amino-pyridin-2-yl)-methyl-amino]-N,N-dimethyl-acetamide was prepared from 2-chloro-5-nitro-pyridine and N,N-dimethyl- 2-methylamino-acetamide. Red oil. LCMS calcd for C10H16N4O (m/e) 208, obsd 209 (M+H).

Preparation of 5-morpholin-4-yl-thiazol-2-ylamine

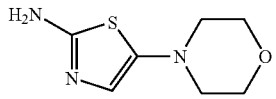

With a method similar to that used for the preparation of 6-morpholin-4-yl-pyridin-3-ylamine above, 5-morpholin-4-yl-thiazol-2-ylamine was prepared from 5-bromo-2-nitro-thiazole and morpholine. LCMS calcd for C7H11N3OS (m/e) 185, obsd 186 (M+H).

Preparation of $N^5$-(2-methoxy-ethyl)-$N^5$-methyl-thiazole-2,5-diamine

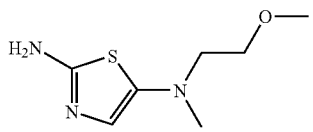

With a method similar to that used for the preparation of 6-morpholin-4-yl-pyridin-3-ylamine above, $N^5$-(2-methoxy-ethyl)-$N^5$-methyl-thiazole-2,5-diamine was prepared from 5-bromo-2-nitro-thiazole and (2-methoxy-ethyl)-methyl-amine. LCMS calcd for C7H13N3OS (m/e) 187, obsd 188 (M+H).

Preparation of N-(5-amino-pyridin-2-yl)-N-methyl-acetamide

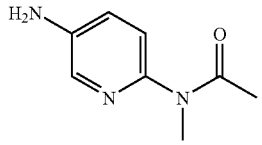

A solution of 2-bromo-5-nitro-pyridine (4 g, 19.7 mmol) and methylamine (2 M in THF, 15 mL, 30 mmol) in methylene chloride (40 mL) was heated at 50 degrees overnight. After cooling to room temperature, the reaction mixture was concentrated to give methyl-(5-nitro-pyridin-2-yl)-amine that was used in the following step without purification. Acetic anhydride (9.3 mL, 98.5 mmol) was added to the solution of methyl-(5-nitro-pyridin-2-yl)-amine (3.01 g, 19.7 mmol), pyridine (24 mL, 197 mmol), and a catalytic amount of 4-dimethylamino-pyridine (DMAP) in methylene chloride (40 mL). The resulted mixture was heated at 90 degrees for overnight. After the reaction was complete, solvent was removed, and then ethyl acetate was added. The ethyl acetate solution was extracted three times with water. Organic layers were combined, washed with brine, dried over sodium sulfate, filtered, and concentrated in vacuo. Flash chromatography (Merck silica gel 60, 230-400 mesh, 50% ethyl acetate in hexane for 20 min) gave N-methyl-N-(5-nitro-pyridin-2-yl)-acetamide.

Hydrogenation reaction of N-methyl-N-(5-nitro-pyridin-2-yl)-acetamide in methanol in presence of a catalytic amount of palladium on carbon was carried out at room temperature with a pressure of 50 psi overnight. After the reaction, the reaction mixture was filtered through a plug of celite. The filtrate was collect and concentrated. Flash chromatography (50 g diol column) gave N-(5-amino-pyridin-2-yl)-N-methyl-acetamide. LCMS calcd for C8H11N3O (m/e) 165, obsd 166 (M+H).

Preparation of N-(5-amino-pyridin-2-yl)-N-methyl-propionamide

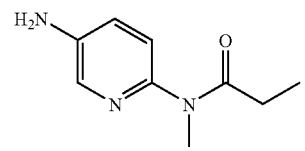

With a method similar to that used for the preparation of N-(5-amino-pyridin-2-yl)-N-methyl-acetamide above, N-(5-amino-pyridin-2-yl)-N-methyl-propionamide was prepared from methyl-(5-nitro-pyridin-2-yl)-amine and propionic anhydride. LCMS calcd for C9H13N3O (m/e) 179, obsd 180 (M+H).

Preparation of cyclopropanecarboxylic acid (5-amino-pyridin-2-yl)-methyl-amide

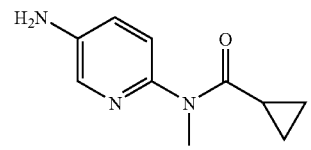

With a method similar to that used for the preparation of N-(5-amino-pyridin-2-yl)-N-methyl-acetamide above, cyclopropanecarboxylic acid (5-amino-pyridin-2-yl)-methyl-amide was prepared from methyl-(5-nitro-pyridin-2-yl)-amine and cyclopropanecarbonyl chloride. The crude product after reducing the nitro group was directly used in the next step without further purification.

Preparation of N-(5-amino-pyridin-2-yl)-2-methoxy-N-methyl-acetamide

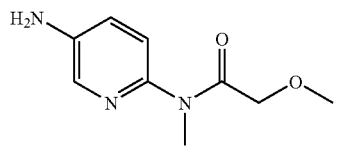

With a method similar to that used for the preparation of N-(5-amino-pyridin-2-yl)-N-methyl-acetamide above, N-(5-amino-pyridin-2-yl)-2-methoxy-N-methyl-acetamide was prepared from methyl-(5-nitro-pyridin-2-yl)-amine and methoxy-acetyl chloride. LCMS calcd for C9H13N3O2 (m/e) 195, obsd 196 (M+H).

Preparation of (S)-2-(5-amino-pyridin-2-ylamino)-propan-1-ol

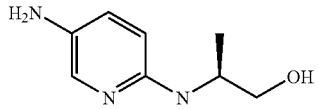

With a method similar to that used for the preparation of 6-morpholin-4-yl-pyridin-3-ylamine above, (S)-2-(5-amino-pyridin-2-ylamino)-propan-1-ol was prepared from (S)-2-(5-nitro-pyridin-2-ylamino)-propan-1-ol (commercially available from TCI-EP). LCMS calcd for C8H13N3O (m/e) 167, obsd 168 (M+H).

Preparation of 6-(3-methoxy-pyrrolidin-1-yl)-pyridin-3-ylamine

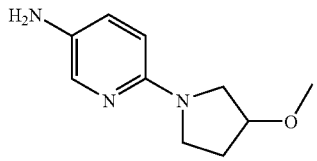

To a solution of 1-(5-nitro-pyridin-2-yl)-pyrrolidin-3-ol (120 mg, 0.57 mmol) in 5 mL of DMF was added 10 equivalent of sodium hydride (228 mg, 5.7 mmol, 60% in mineral oil). The mixture was stirred at 23° C. for 15 min followed by the addition of 10 equivalent of iodomethane (355 uL, 5.7 mmol). The reaction was continually stirred for 2 h and then extracted with ethyl acetate and water. The organic phase was dried and solvent was evaporated. The residue was purified on a flash chromatography column with EtOAc/hexanes to afford 2-(3-methoxy-pyrrolidin-1-yl)-5-nitro-pyridine. LRMS calcd for C10H13N3O3 (m/e) 223, obsd 224 (M+H).

This nitro compound was dissolved in 10 mL of EtOAc, and treated with 100 mg of 10% palladium on carbon. The reaction was shaken under 50 psi of $H_2$ overnight. The reaction was filtered through a celite pad, and the filtrate was concentrated to afford 6-(3-methoxy-pyrrolidin-1-yl)-pyridin-3-ylamine, which was used directly in the next step without further purification. LRMS calcd for C10H15N3O (m/e) 193, obsd 194 (M+H).

Preparation of 3-methoxy-3,4,5,6-tetrahydro-2H-[1,2']bipyridinyl-5'-ylamine

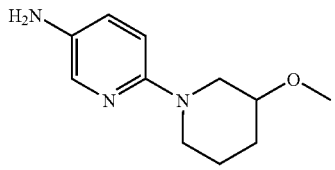

With a method similar to that used for the preparation of 6-(3-methoxy-pyrrolidin-1-yl)-pyridin-3-ylamine above, 3-methoxy-3,4,5,6-tetrahydro-2H-[1,2']bipyridinyl-5'-ylamine was prepared from 5'-nitro-3,4,5,6-tetrahydro-2H-[1,2']bipyridinyl-3-ol and iodomethane. LCMS calcd for C11H17N3O (m/e) 207, obsd 208 (M+H).

Preparation of $N^2$—((S)-2-methoxy-1-methyl-ethyl)-$N^2$-methyl-pyridine-2,5-diamine

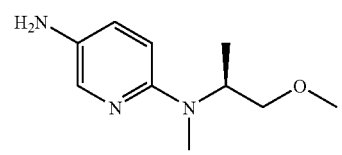

With a method similar to that used for the preparation of 6-(3-methoxy-pyrrolidin-1-yl)-pyridin-3-ylamine above, $N^2$—((S)-2-methoxy-1-methyl-ethyl)-$N^2$-methyl-pyridine-2,5-diamine was prepared from (S)-2-(5-amino-pyridin-2-ylamino)-propan-1-ol and iodomethane. LCMS calcd for C10H17N3O (m/e) 195, obsd 196 (M+H).

Preparation of $N^2$-(2-cyclopropylmethoxy-ethyl)-$N^2$-methyl-pyridine-2,5-diamine

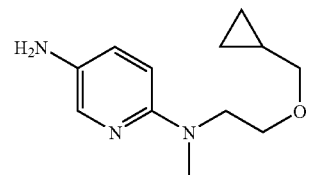

With a method similar to that used for the preparation of 6-(3-methoxy-pyrrolidin-1-yl)-pyridin-3-ylamine above, $N^2$-(2-cyclopropylmethoxy-ethyl)-$N^2$-methyl-pyridine-2,5-diamine was prepared from 2-[methyl-(5-nitro-pyridin-2-yl)-amino]-ethanol and bromomethyl-cyclopropane. LCMS calcd for C12H19N3O (m/e) 221, obsd 222 (M+H).

Preparation of (S)-2-N-(tetrahydrofuran-3-yl)-2,5-diaminopyridine

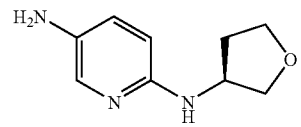

The (S)-3-aminotetrahydrofuran was prepared as a tosylate salt according to the procedure described in literature (*Journal of the Chemical Society, Chemical Communication* 6, 474-475, 1987). (L)-methionine was protected as N-trityl-(L)-methionine and the carboxylic acid was reduced to alcohol. The resulting N-tritylmethioninol was methylated to form a sulfonium salt which was cyclized to form (S)—N-trityl-3-aminotetrahydrofuran. Final deprotection with p-toluene sulfonic acid in methanol provided (S)-3-aminotetrahydrofuran tosylate as a white solid.

To a mixture of 2-chloro-5-nitropyridine (190 mg, 1.2 mmol) and (S)-3-aminotetrahydrofuran tosylate (305 mg, 1.18 mmol) in DMF (5 mL) was added potassium carbonate (340 mg, 2.46 mmol) and triethyl amine (0.17 mL, 1.22 mmol). The mixture was heated at 65° C. overnight and solvents were evaporated. The residue was dissolved in ether and extracted with brine. Solvents were evaporated and the oily residue was purified by flash column chromatography using ethyl acetate and hexanes (10% to 40% ethyl acetate) to give (S)-2-(N-tetrahydrofuran)amino-5-nitro-pyridine as a yellowish oil (180 mg, 73%). $[\alpha]_D$=+9.76 (0.675, CHCl$_3$). LCMS calcd for C9H11N3O3 m/e 209.2, obsd 210.1 (M+H). The nitro compound (170 mg, 0.81 mmol) was hydrogenated in methanol with catalytic amount of 5% palladium on carbon (35 mg) at 40 psi for 2 hrs. The mixture was filtered and solvents were evaporated to give the desired compound as an oil (139 mg). MS calcd for C9H13N3O m/e 179.2, obsd 180.0 (M+H).

Preparation of 2-N-(tetrahydrofuran-3-yl)-2,5-diaminopyridine

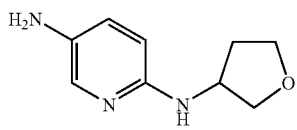

This compound was prepared with the same method described for the preparation of (S)-2-N-(tetrahydrofuran-3-yl)-2,5-diaminopyridine by using 2-chloro-5-nitro-pyridine and racemic 3-aminotetrahydrofuran which was synthesized through a Curtius rearrangement of tetrahydrofuran-3-carboxylic acid. LCMS calcd for C9H13N3O m/e 179.2, obsd 180.0 (M+H).

Preparation of 2-N-(tetrahydropyran-4-yl)-2,5-diaminopyridine

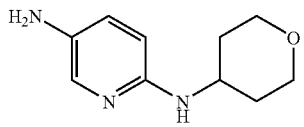

This compound was prepared with the same method described before by using 4-aminotetrahydropyran and 2-chloro-5-nitro-pyridine. LCMS calcd for C10H15N3O m/e 193.2, obsd 194.1 (ES, M+H).

Preparation of (R)-2-N-(1-phenylethyl)-2,5-diaminopyridine

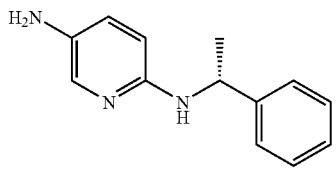

This compound was prepared with the same method described before by using (R)-(α)-methylbenzylamine and 2-chloro-5-nitropyridine to give (R)-2-N-(1-phenylethyl)-2-amino-5-nitro-pyridine. LCMS calcd for C13H13N3O2 m/e 243.2, obsd 244.1 (ES, M+H). The nitro compound was reduced under hydrogenation condition as described before to give (R)-2-N-(1-phenylethyl)-2,5-diaminopyridine.

Preparation of (R)—N-(5-aminopyrimidin-2-yl)-pyrrolidin-3-ol

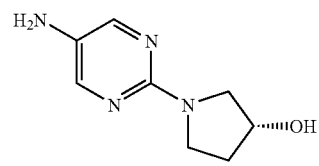

This compound was prepared with the same method described before by using 2-methoxy-1-methylethylamine and 2-chloro-5-nitro-pyridine to give N-(2-methoxy-1-methylethyl)-2-amino-5-nitro-pyridine. LCMS calcd for C9H13N3O3 m/e 211.22, obsd 210.2 (AP, M–H). The nitro compound was hydrogenated under the same condition described before to give $N^2$-(2-methoxy-1-methylethyl)-2,5-diaminopyridine.

Preparation of N-(5-aminopyrimidin-2-yl)-pyrrolidin-3-ol

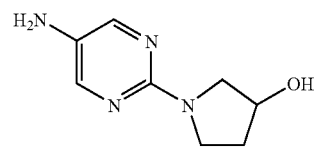

To a solution of 2-chloro-5-nitro-pyrimidine (638 mg, 4 mmol) in THF (15 mL) cooled to 0° C. was added 3-hydroxypyrrolidine (392 mg, 4.5 mmol) and triethylamine (1.2 mL). The mixture was stirred at room temperature overnight. Solids were filtered out and the solution was concentrated. The residue was dissolved in ethyl acetate and extracted with water. Organic layer was washed with dilute aqueous citric acid solution. After the evaporation of solvents, the residue was treated with ether and the yellow solid was filtered to give N-(5-nitro-pyrimidin-2-yl)-pyrrolidin-3-ol (570 mg). LCMS calcd for C8H10N4O3 m/e 210.19, obsd 211.0 (ES, M+H). Hydrogenation of the nitro compound, as above, provided N-(5-aminopyrimidin-2-yl)-pyrrolidin-3-ol.

Preparation of (R)—N-(5-aminopyrimidin-2-yl)-pyrrolidin-3-ol

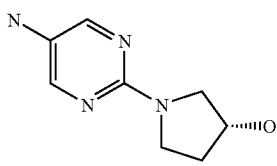

This compound was prepared with the same method described before using (R)-3-hydroxypyrrolidine and 2-chloro-5-nitropyrimidine to give (R)—N-(5-nitro-pyrimidin-2-yl)-pyrrolidin-3-ol. LCMS calcd for C8H10N4O3 m/e 210.19, obsd 211.0 (ES, M+H). Hydrogenation of the nitro compound, as above, provided (R)—N-(5-aminopyrimidin-2-yl)-pyrrolidin-3-ol.

Preparation of (S)—N-(5-aminopyrimidin-2-yl)-pyrrolidin-3-ol

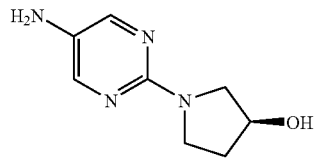

This compound was prepared with the same method described before using (S)-3-hydroxypyrrolidine and 2-chloro-5-nitro-pyrimidine to give (S)—N-(5-nitropyrimidin-2-yl)-pyrrolidin-3-ol. LCMS calcd for C8H10N4O3 m/e 210.19, obsd 211 (ES, M+H). Hydrogenation of the nitro compound, as above, provided (S)—N-(5-aminopyrimidin-2-yl)-pyrrolidin-3-ol.

Preparation of 3-amino-6-(3,3-difluoroazetidin-1-yl)pyridine

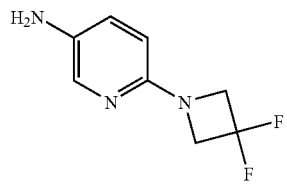

The 2-chloro-5-nitro-pyridine (317 mg, 2 mmol) and 3,3-difluoroazetidine hydrochloride (259 mg, 2 mmol) was mixed in 8 mL of THF. Diisopropylethylamine (1.4 mL) was added and the mixture was heated in a microwave at 120° C. for 20 minutes. After cooling to room temperature, the solid was filtered and the filtrate was distributed between ethyl acetate and water. The organic layers were evaporated and the solid material was triturated with methanol. The resulting solid was filtered to give 5-nitro-2-(3,3-difluoroazetidin-1-yl)pyridine. LCMS calcd for C8H7F2N3O2 m/e 215.16, obsd 216.1 (ES, M+H). Hydrogenation of the nitro compound, as above, provided 3-amino-6-(3,3-difluoroazetidin-1-yl)pyridine.

Preparation of $N^2$-methyl-$N^2$-(2,2,2-trifluoro-ethyl)-pyridine-2,5-diamine

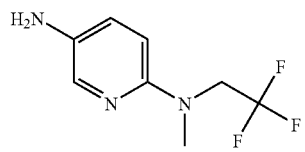

A mixture of 2-chloro-5-nitro-pyridine (500 mg, 3.15 mmol), 2,2,2-trifluoro-ethylamine (940 mg, 9.45 mmol) and N,N-diisopropylethylamine (1.64 mL, 9.45 mmol) in 1-methyl-pyrrolidin-2-one (10 mL) in a sealed tube was heated by microwave at 200° C. for 10 minutes. The reaction mixture was evaporated to dryness and purified by silica gel chromatography (Isco 120 g column, 40% ethyl acetate/hexanes) to give (5-nitro-pyridin-2-yl)-(2,2,2-trifluoro-ethyl)-amine (300 mg, 43%) as a yellow solid. LCMS calcd for C7H6F3N3O2 (m/e) 221, obsd 222 (M+H). The NMR spectrum obtained on the sample is compatible with its structure.

A mixture of (5-nitro-pyridin-2-yl)-(2,2,2-trifluoro-ethyl)-amine (230 mg, 1.04 mmol), cesium carbonate (730 mg, 2.07 mmol) and iodomethane (0.59 mL, 4.18 mmol) in DMF (4 mL) was heated in a sealed tube at 50° C. for 3 hr. The reaction mixture was evaporated to dryness and the crude was partitioned between methylene chloride and water. The organic layer was dried over magnesium sulfate, filtered and concentrated to give methyl-(5-nitro-pyridin-2-yl)-(2,2,2-trifluoro-ethyl)-amine (270 mg, crude) as a brown solid, which was directly used in the next step reaction without further purification. LCMS calcd for C8H8F3N3O2 (m/e) 235, obsd 236 (M+H).

A solution of methyl-(5-nitro-pyridin-2-yl)-(2,2,2-trifluoro-ethyl)-amine (80 mg, 0.34 mmol) in ethanol (10 mL) in the presence of 10% palladium on carbon (10 mg) was shaken under hydrogen with a pressure of 50 psi at room temperature for 2 hours. After the reaction was complete, the reaction mixture was filtered through a plug of celite and the filtration pad was washed with ethanol. The organic layers were combined and concentrated to give $N^2$-methyl-$N^2$-(2,2,2-trifluoro-ethyl)-pyridine-2,5-diamine (70 mg, crude) as a brown oil, which was directly used in the next step without further purification. LCMS calcd for C8H10F3N3 (m/e) 205, obsd 206 (M+H).

Preparation of N-methyl-N-(2,2,2-trifluoro-ethyl)-pyrimidine-2,5-diamine

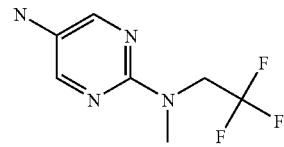

With procedures similar to that used for the preparation of $N^2$-methyl-$N^2$-(2,2,2-trifluoro-ethyl)-pyridine-2,5-diamine above, N-methyl-N-(2,2,2-trifluoro-ethyl)-pyrimidine-2,5-diamine was prepared from 2-chloro-5-nitro-pyrimidine and 2,2,2-trifluoro-ethylamine. LCMS calcd for C7H9F3N4 (m/e) 206, obsd 207 (M+H). The NMR spectrum obtained on the sample is compatible with its structure.

Preparation of 5-isopropyl-2-phenyl-oxazole-4-carboxylic acid

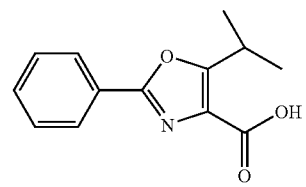

Lithium bis(trimethylsilyl)amide (1M in THF, 6 mL, 6 mmol) was added to (benzhydrylidene-amino)-acetic acid benzyl ester (1.97 g, 6 mmol) in tetrahydrofuran (10 mL) at −78 degrees. The reaction mixture was stirred at this temperature for about 1 hr. Then isobutyryl chloride (0.641 mL, 6 mmol) in tetrahydrofuran (5 mL) was slowly added into the above mixture. The reaction mixture was warmed up to room temperature and continued for another 2 hr. After the completion of the above reaction, the reaction mixture was quenched with dilute hydrochloride acid (2 M) and stirred at room temperature for 1 hr. After removal of tetrahydrofuran, the aqueous solution was extracted with ethyl acetate twice. The collected organic layers were extracted with dilute hydrochloride acid (2M). The combined aqueous solution was concentrated in vacuo to give 2-amino-4-methyl-3-oxo-pentanoic acid benzyl ester acid chloride, which was used in the next step without further purification. Benzoyl chloride (3 mL) was slowly added to mixture of 2-amino-4-methyl-3-oxo-pentanoic acid benzyl ester acid chloride (1.63 g, 6 mmol) and anhydrous pyridine (20 mL) in dichloromethane (60 mL) at room temperature. The reaction mixture was stirred at room temperature for 1 hr, after which the solvent was removed and water was added. The resulted mixture was extracted with ethyl acetate three times. The organic layers were collected, washed with brine, dried over sodium sulfate, and concentrate in vacuo. Flash chromatography (Merck silica gel 60, 230-400 mesh, 0-40% ethylacetate in hexane for 20 min) gave 2-benzoylamino-4-methyl-3-oxo-pentanoic acid benzyl ester (1.08 g, 53%) as a light yellow solid. LCMS calcd for C20H21NO4 (m/e) 339, obsd 340 (M+H).

Mixture of 2-benzoylamino-4-methyl-3-oxo-pentanoic acid benzyl ester (1.08 g, 3 mmol), triphenylphosphine (2.01 g, 8 mmol), and iodine (1.62 g, 6.37 mmol) in tetrahydrofuran (60 mL) was cooled to −78 degrees, followed by addition of triethylamine (1.7 mL). The resulted solution was stirred at −78 degrees for about 10 min, and then was warmed up to room temperature. The reaction continued at room temperature for about 1 hr. After the reaction, the solvent was removed, and dichloromethane was added. The resulted solution was washed in sequence with saturated sodium bicarbonate, citric acid (0.5 M), and brine, dried over sodium sulfate, filtered and then concentrated in vacuo. Flash chromatography (Merck silica gel 60, 230-400 mesh, 0-40% ethyl acetate in hexane for 20 min) gave 5-isopropyl-2-phenyl-oxazole-4-carboxylic acid benzyl ester (0.84 g, 82%) as a light yellow solid. LCMS calcd for C20H19NO3 (m/e) 321, obsd 322 (M+H).

Solution of 5-isopropyl-2-phenyl-oxazole-4-carboxylic acid benzyl ester (830 mg, 2.59 mmol) in a mix of tetrahydrofuran, methanol and water (3:1:1, 10 mL) was treated with lithium hydroxide monohydride (258 mg, 6.5 mmol) at room temperature for an hour. After the reaction was complete, solvent was removed. To the residue, water and dichloromethane were added, and white precipitate formed. After filtering off the solid, filtrate was collected and the phases were separated. The pH of the aqueous layer was adjusted to 1~2 with dilute hydrochloride acid (1N). Then the aqueous layer was extracted with ethyl acetate three times. The ethyl acetate layers were collected, dried over sodium sulfate, and concentrated in vacuo. Flash chromatography (Merck silica gel 60, 230-400 mesh, 0-80% ethyl acetate in hexane for 20 min) gave 5-isopropyl-2-phenyl-oxazole-4-carboxylic acid (247 mg, 41%) as a white solid. LCMS calcd for C13H13NO3 (m/e) 231, obsd 232 (M+H).

Preparation of
5-ethyl-2-phenyl-oxazole-4-carboxylic acid

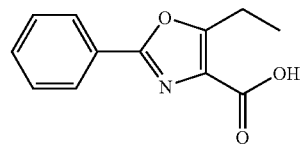

With a method similar to that used for the preparation of 5-isopropyl-2-phenyl-oxazole-4-carboxylic acid above, 5-ethyl-2-phenyl-oxazole-4-carboxylic acid was prepared from (benzhydrylidene-amino)-acetic acid benzyl ester, propionyl chloride and benzoyl chloride. LCMS calcd for C12H11NO3 (m/e) 217, obsd 218 (M+H).

Preparation of
2-phenyl-5-propyl-oxazole-4-carboxylic acid

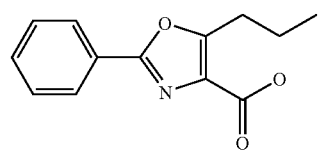

With a method similar to that used for the preparation of 5-isopropyl-2-phenyl-oxazole-4-carboxylic acid above, 2-phenyl-5-propyl-oxazole-4-carboxylic acid was prepared from (benzhydrylidene-amino)-acetic acid benzyl ester, butyryl chloride and benzoyl chloride. LCMS calcd for C13H13NO3 (m/e) 231, obsd 232 (M+H).

Preparation of
2-(2-chloro-phenyl)-5-propyl-oxazole-4-carboxylic
acid

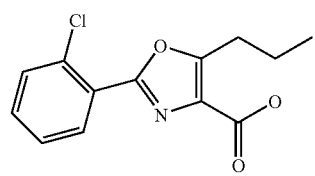

With a method similar to that used for the preparation of 5-isopropyl-2-phenyl-oxazole-4-carboxylic acid above, 2-(2-chloro-phenyl)-5-propyl-oxazole-4-carboxylic acid was prepared from (benzhydrylidene-amino)-acetic acid benzyl ester, butyryl chloride and 2-chloro-benzoyl chloride. LCMS calcd for C13H12ClNO3 (m/e) 265, obsd 266 (M+H).

Preparation of 2-(2-bromo-phenyl)-5-propyl-oxazole-4-carboxylic acid

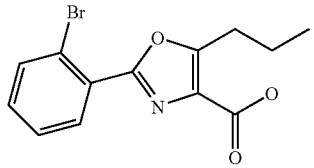

With a method similar to that used for the preparation of 5-isopropyl-2-phenyl-oxazole-4-carboxylic acid above, 2-(2-bromo-phenyl)-5-propyl-oxazole-4-carboxylic acid was prepared from (benzhydrylidene-amino)-acetic acid benzyl ester, butyryl chloride and 2-bromo-benzoyl chloride. LCMS calcd for C13H12BrNO3 (m/e) 310, obsd 311 (M+H).

Preparation of 5-propyl-2-o-tolyl-oxazole-4-carboxylic acid

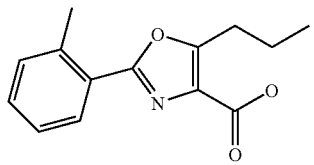

With a method similar to that used for the preparation of 5-isopropyl-2-phenyl-oxazole-4-carboxylic acid above, 5-propyl-2-o-tolyl-oxazole-4-carboxylic acid was prepared from (benzhydrylidene-amino)-acetic acid benzyl ester, butyryl chloride and 2-methyl-benzoyl chloride. LCMS calcd for C14H15NO3 (m/e) 245, obsd 246 (M+H).

Preparation of 2-cyclohexyl-5-propyl-oxazole-4-carboxylic acid

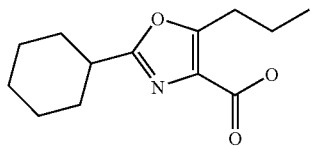

With a method similar to that used for the preparation of 5-isopropyl-2-phenyl-oxazole-4-carboxylic acid above, 2-cyclohexyl-5-propyl-oxazole-4-carboxylic acid was prepared from (benzhydrylidene-amino)-acetic acid benzyl ester, butyryl chloride and cyclohexanecarbonyl chloride. LCMS calcd for C13H19NO3 (m/e) 237, obsd 238 (M+H).

Preparation of 5-chloro-2-phenyl-oxazole-4-carboxylic acid

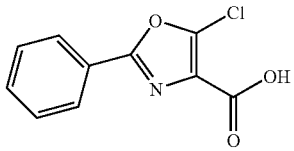

A mixture of phenylboronic acid (729 mg, 5.98 mmol), 2-chloro-oxazole-4-carboxylic acid ethyl ester (prepared according to the procedures described in Org. Lett. 2002, 4 (17), 2905 and J. Med. Chem. 1971, 14, 1075) (1.0 g, 5.70 mmol), Pd[PPh3]4 (329 mg, 0.285 mmol), and sodium carbonate (2M, 2 mL) in ethylene glycol dimethyl ether (10 mL) were heated at 90 degrees overnight. After cooling the reaction, solvent was removed to give the crude residue. Flash chromatography (Merck silica gel 60, 230-400 mesh, 5-45% ethyl acetate in hexane for 35 min) gave 2-phenyl-oxazole-4-carboxylic acid ethyl ester (1.03 g, 83%) as colorless oil. LCMS calcd for C12H11NO3 (m/e) 217, obsd 218 (M+H).

Mixture of 2-phenyl-oxazole-4-carboxylic acid ethyl ester (217 mg, 1 mmol), 1-chloro-pyrrolidine-2,5-dione (400 mg, 3 mmol) and two drops of sulfuric acid in chloroform (10 mL) was heated at 90 degrees for overnight. After the reaction was complete, solvent was evaporated. To the residue, water was added, and then the mixture was extracted with ethyl acetate twice. The organic layers were collected, combined, washed with saturated sodium bicarbonate, dried over sodium sulfate, filtered, and concentrated in vacuo. Flash chromatography (Merck silica gel 60, 230-400 mesh, 5-40% ethyl acetate in hexane for 30 min) gave 5-chloro-2-phenyl-oxazole-4-carboxylic acid ethyl ester (95 mg, 37%) as a white solid. LCMS calcd for C12H10ClNO3 (m/e) 251, obsd 252 (M+H).

Solution of 5-chloro-2-phenyl-oxazole-4-carboxylic acid ethyl ester (92 mg, 0.37 mmol) in a mixture solution of tetrahydrofuran, methanol and water (3:1:1, 5 mL) was treated with lithium hydroxide monohydride (44 mg, 1.1 mmol) at room temperature for two hours. After the reaction was complete, solvent was evaporated. To the residue, water was added, and pH value of the aqueous layer was adjusted to ~1-2 by addition of dilute hydrochloride acid (1N). The white precipitation was collected by centrifugation to give 5-chloro-2-phenyl-oxazole-4-carboxylic acid (73 mg, 88%). LCMS calcd for C10H6ClNO3 (m/e) 223, obsd 224 (M+H).

Preparation of 5-bromo-2-phenyl-oxazole-4-carboxylic acid

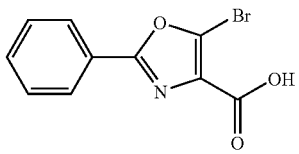

With a method similar to that used for the preparation of 5-chloro-2-phenyl-oxazole-4-carboxylic acid above, 5-bromo-2-phenyl-oxazole-4-carboxylic acid was prepared from 2-phenyl-oxazole-4-carboxylic acid ethyl ester, 1-bromo-pyrrolidine-2,5-dione. LCMS calcd for C10H6BrNO3 (m/e) 268, obsd 269 (M+H).

Preparation of 4-phenyl-thiazole-2-carboxylic acid

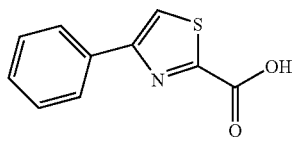

4-Phenyl-thiazole-2-carboxylic acid ethyl ester, commercially available from Pharma Core, (1.0 g, 4.28 mmol) in a mixture solution of tetrahydrofuran, methanol and water (3:1:1, 10 mL) was treated with lithium hydroxide monohydride (514 mg, 12.8 mmol) at room temperature for three hours. After the reaction was complete, solvent was evaporated. To the residue, water was added, and pH of the resulting solution was adjusted to ~1-2 by addition of dilute hydrochloride acid (1N). The white precipitation was collected by centrifugation and further washed with water to give 4-phenyl-thiazole-2-carboxylic acid (473 mg, 54%). LCMS calcd for C10H7NO2S (m/e) 205, obsd 206 (M+H).

Preparation of (methyl-{5-[(2-phenyl-5-trifluoromethyl-oxazole-4-carbonyl)-amino]-pyridin-2-yl}-amino)-acetic acid

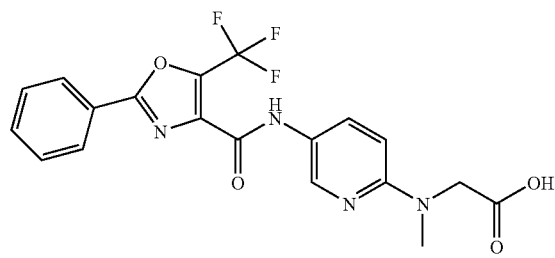

From (methyl-{5-[(2-phenyl-5-trifluoromethyl-oxazole-4-carbonyl)-amino]-pyridin-2-yl}-amino)-acetic acid methyl ester: (methyl-{5-[(2-phenyl-5-trifluoromethyl-oxazole-4-carbonyl)-amino]-pyridin-2-yl}-amino)-acetic acid. LCMS calcd for C19H15F3N4O4 (m/e) 420, obsd 421 (M+H).

Preparation of 2-(2-chloro-phenyl)-4-ethyl-oxazole-5-carboxylic acid 2,5-dioxo-pyrrolidin-1-yl ester

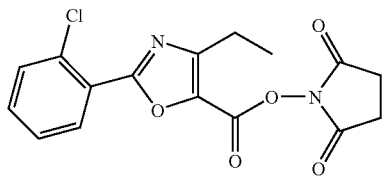

This compound was prepared according to the procedures described in *Int. J. Peptide Protein Res.* 1989, 33, 353, and *J. Chem. Soc., Chem. Commun.* 1995, 2335. 2-Amino-butyric acid (3.87 g, 37.5 mmol) was suspended in 90 mL of dichloromethane, and treated with chloro-trimethyl-silane (9.6 mL, 75 mmol). The mixture was refluxed for 1 h and cooled in an ice bath. Diisopropylethylamine (11.3 mL, 65 mmol) and 2-chloro-benzoyl chloride (4.3 mL, 35.6 mmol) were added. The solution was stirred with cooling for 20 min and then warmed up to room temperature for 1.5 h. The mixture was concentrated and then distributed between ether and diluted NaHCO3 solution. The phases were separated. The aqueous layer was extracted with ether and the ether layer was back washed with water. The combined aqueous layers were acidified to pH 2 with 1N HCl and extracted with ethyl acetate three times. The combined ethyl acetate layers were dried over sodium sulfate, filtered and concentrated to give 2-(2-chloro-benzoylamino)-butyric acid as an off-white solid (7.0 g, 77% yield), which was used directly in the next step without further purification. LCMS calcd for C11H12ClNO3 (m/e) 241, obsd 242 (M+H).

To a stirred slurry of 2-(2-chloro-benzoylamino)-butyric acid (2.84 g, 11.8 mmol) in 60 mL of anhydrous tetrahydro furan, was added oxalyl chloride (10.1 mL, 118 mmol). The mixture was stirred at 50° C. overnight and then the solvent was evaporated in vacuo. The oily residue was treated with toluene and evaporated to remove trace of oxalyl chloride. The residue was then cooled in an ice bath and triethylamine (3.4 mL, 23.6 mmol) was added followed by the addition of 1-hydroxy-pyrrolidine-2,5-dione. The reaction mixture was stirred at 50° C. overnight before the solvent was removed in vacuo. The residue was then purified by flash chromatography (Merck silica gel 60, 230-400 mesh, 5-60% ethyl acetate in hexane for 25 min) to give 2-(2-chloro-phenyl)-4-ethyl-oxazole-5-carboxylic acid 2,5-dioxo-pyrrolidin-1-yl ester (997 mg, 25% yield) as a light yellow solid. LCMS calcd for C16H13ClN2O5 (m/e) 348, obsd 349 (M+H).

Preparation of 2-(2-chloro-phenyl)-4-propyl-oxazole-5-carboxylic acid 2,5-dioxo-pyrrolidin-1-yl ester

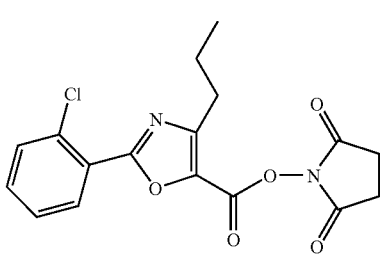

With a method similar to that used for the preparation of 2-(2-chloro-phenyl)-4-ethyl-oxazole-5-carboxylic acid 2,5-dioxo-pyrrolidin-1-yl ester above, 2-(2-chloro-phenyl)-4-propyl-oxazole-5-carboxylic acid 2,5-dioxo-pyrrolidin-1-yl ester was prepared from DL-norvaline and 2-chloro-benzoyl chloride. LCMS calcd for C17H15ClN2O5 (m/e) 362, obsd 363 (M+H).

Preparation of 4-methyl-2-phenyl-oxazole-5-carboxylic acid 2,5-dioxo-pyrrolidin-1-yl ester

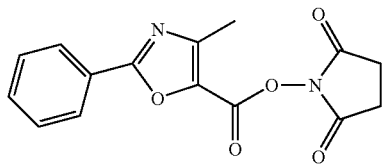

With a method similar to that used for the preparation of 2-(2-chloro-phenyl)-4-ethyl-oxazole-5-carboxylic acid 2,5-dioxo-pyrrolidin-1-yl ester above, 4-methyl-2-phenyl-oxazole-5-carboxylic acid 2,5-dioxo-pyrrolidin-1-yl ester was prepared from DL-alanine and benzoyl chloride. LCMS calcd for C15H12N2O5 (m/e) 300, obsd 301 (M+H).

Preparation of 4-methyl-2-o-tolyl-oxazole-5-carboxylic acid 2,5-dioxo-pyrrolidin-1-yl ester

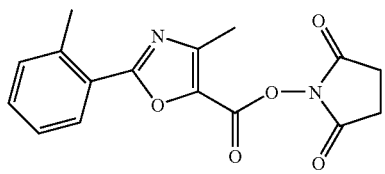

With a method similar to that used for the preparation of 2-(2-chloro-phenyl)-4-ethyl-oxazole-5-carboxylic acid 2,5-dioxo-pyrrolidin-1-yl ester above, 4-methyl-2-o-tolyl-oxazole-5-carboxylic acid 2,5-dioxo-pyrrolidin-1-yl ester was prepared from DL-alanine and 2-methyl-benzoyl chloride. LCMS calcd for C16H14N2O5 (m/e) 314, obsd 315 (M+H).

Preparation of 4-propyl-2-o-tolyl-oxazole-5-carboxylic acid 2,5-dioxo-pyrrolidin-1-yl ester

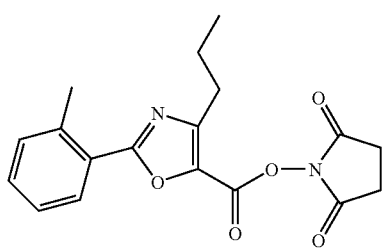

With a method similar to that used for the preparation of 2-(2-chloro-phenyl)-4-ethyl-oxazole-5-carboxylic acid 2,5-dioxo-pyrrolidin-1-yl ester above, 4-propyl-2-o-tolyl-oxazole-5-carboxylic acid 2,5-dioxo-pyrrolidin-1-yl ester was prepared from DL-norvaline and 2-methyl-benzoyl chloride. LCMS calcd for C18H18N2O5 (m/e) 342, obsd 343 (M+H).

Preparation of 4-(2-methylsulfanyl-ethyl)-2-phenyl-oxazole-5-carboxylic acid 2,5-dioxo-pyrrolidin-1-yl ester

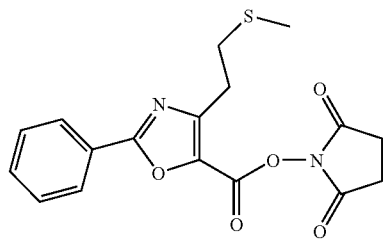

With a method similar to that used for the preparation of 2-(2-chloro-phenyl)-4-ethyl-oxazole-5-carboxylic acid 2,5-dioxo-pyrrolidin-1-yl ester above, 4-(2-methylsulfanyl-ethyl)-2-phenyl-oxazole-5-carboxylic acid 2,5-dioxo-pyrrolidin-1-yl ester was prepared from DL-methionine and benzoyl chloride. LCMS calcd for C17H16N2O5S (m/e) 360, obsd 361 (M+H).

Preparation of 2-(2-bromo-phenyl)-4-propyl-oxazole-5-carboxylic acid 2,5-dioxo-pyrrolidin-1-yl ester

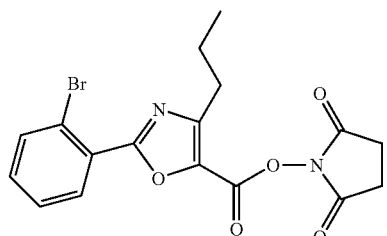

With a method similar to that used for the preparation of 2-(2-chloro-phenyl)-4-ethyl-oxazole-5-carboxylic acid 2,5-dioxo-pyrrolidin-1-yl ester above, 2-(2-bromo-phenyl)-4-propyl-oxazole-5-carboxylic acid 2,5-dioxo-pyrrolidin-1-yl ester was prepared from DL-norvaline and 2-bromo-benzoyl chloride. LCMS calcd for C17H15BrN2O5 (m/e) 407, obsd 408 (M+H).

Preparation of 2-cyclohexyl-4-propyl-oxazole-5-carboxylic acid 2,5-dioxo-pyrrolidin-1-yl ester

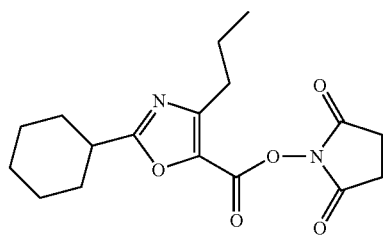

With a method similar to that used for the preparation of 2-(2-chloro-phenyl)-4-ethyl-oxazole-5-carboxylic acid 2,5- dioxo-pyrrolidin-1-yl ester above, 2-cyclohexyl-4-propyl-oxazole-5-carboxylic acid 2,5-dioxo-pyrrolidin-1-yl ester was prepared from DL-norvaline and cyclohexanecarbonyl chloride. LCMS calcd for C17H22N2O5 (m/e) 334, obsd 335 (M+H).

Preparation of
2-phenyl-4-propyl-oxazole-5-carboxylic acid
2,5-dioxo-pyrrolidin-1-yl ester

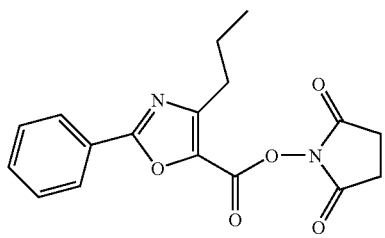

With a method similar to that used for the preparation of 2-(2-chloro-phenyl)-4-ethyl-oxazole-5-carboxylic acid 2,5-dioxo-pyrrolidin-1-yl ester above, 2-phenyl-4-propyl-oxazole-5-carboxylic acid 2,5-dioxo-pyrrolidin-1-yl ester was prepared from DL-norvaline and benzoyl chloride. LCMS calcd for C17H16N2O5 (m/e) 328, obsd 329 (M+H).

Preparation of 2-(2-chloro-phenyl)-5-trifluoromethyl-oxazole-4-carboxylic acid

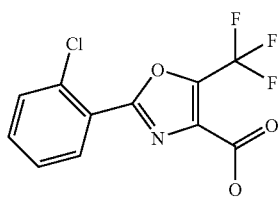

Amino-acetic acid methyl ester (5 g, 40 mmol) was suspended in DMF and treated with triethylamine (13.9 mL, 100 mmol) and 2-chloro-benzoyl chloride (5 mL, 40 mmol). The reaction mixture was stirred at room temperature overnight. Water was added to the reaction, and the mixture was extracted with ethyl acetate three times. The organic layers were combined and dried over sodium sulfate, filtered and concentrated. The residue was purified by flash chromatography using ethyl acetate/hexane to yield (2-chloro-benzoylamino)-acetic acid methyl ester as a light yellow solid. LCMS calcd for C10H10ClNO3 (m/e) 227, obsd 228 (M+H).

To a solution of above (2-chloro-benzoylamino)-acetic acid methyl ester (6 g, 26 mmol) in 30 mL of methanol, was added three equivalents of lithium hydroxide hydrate in 10 mL of water. The solution was stirred at room temperature for 1 hour, concentrated and mixed with water. Citric acid was added until pH of the solution was adjusted to pH 2 to 3. The mixture was extracted with ethyl acetate and the organic layer was washed with water and brine, dried over MgSO4, filtered and concentrated to dryness to give (2-chloro-benzoylamino)-acetic acid as a solid. To a solution of (2-chloro-benzoylamino)-acetic acid in 40 mL of acetone at −20° C. was added excess of trifluoroacetic anhydride. The mixture was warmed up to room temperature and stirred overnight. The solvent was removed under vacuum. The residue was poured into 400 mL of water and stirred for 20 min. The solid was filtered out and washed with 2×100 mL of water, and dried under vacuum to give 2-(2-chloro-benzoylamino)-4,4,4-trifluoro-3,3-dihydroxy-butyric acid as a red solid. This red solid was suspended in 80 mL of methanol, and heated to reflux for 30 min. The solvent was removed and the mixture was purified by flash chromatography using ethyl acetate/hexane to give 2-(2-chloro-benzoylamino)-4,4,4-trifluoro-3,3-dihydroxy-butyric acid methyl ester as a light yellow solid. The methyl ester was suspended in 100 g of phosphorus oxychloride, and stirred at 80° C. overnight. The reaction mixture was concentrated to remove excess POCl3. The remaining oil was diluted with toluene, and poured into a mixture of ice-water. The layers were separated and the organic layer was washed with water and diluted sodium bicarbonate and then concentrated to dryness. The solid was dissolved in 30 mL of methanol and treated with 2.5 equivalent of lithium hydroxide in 30 mL of water, and stirred for 30 min. Methanol was removed under vacuum, and the mixture was diluted with water. pH of the solution was adjusted to about 3 with 12 M hydrochloric acid, and the mixture was extracted with ethyl acetate. The organic layer was concentrated and purified by flash chromatography to give 1.67 g of 2-(2-chloro-phenyl)-5-trifluoromethyl-oxazole-4-carboxylic acid as a light yellow solid. LCMS calcd for C11H5ClF3NO3 (m/e) 291, obsd 292 (M+H).

Preparation of 2-(2-bromo-phenyl)-5-trifluoromethyl-oxazole-4-carboxylic acid

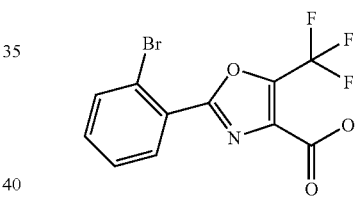

With a method similar to that used for the preparation of 2-(2-chloro-phenyl)-5-trifluoromethyl-oxazole-4-carboxylic acid above, 2-(2-bromo-phenyl)-5-trifluoromethyl-oxazole-4-carboxylic acid was prepared from 2-bromo-benzoyl chloride, amino-acetic acid methyl ester and trifluoroacetic anhydride. LCMS calcd for C11H5BrF3NO3 (m/e) 336, obsd 337 (M+H).

Preparation of 2-(2-ethyl-phenyl)-5-trifluoromethyl-oxazole-4-carboxylic acid

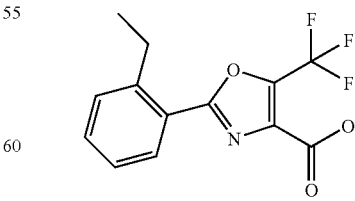

With a method similar to that used for the preparation of 2-(2-chloro-phenyl)-5-trifluoromethyl-oxazole-4-carboxylic acid above, 2-(2-ethyl-phenyl)-5-trifluoromethyl-oxazole-4-carboxylic acid was prepared from 2-ethyl-benzoyl chloride, amino-acetic acid methyl ester and trifluoroacetic anhydride. LCMS calcd for C13H10F3NO3 (m/e) 285, obsd 286 (M+H).

Preparation of 2-(2-trifluoromethoxy-phenyl)-5-trifluoromethyl-oxazole-4-carboxylic acid

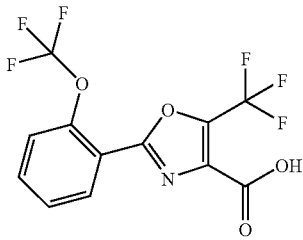

With a method similar to that used for the preparation of 2-(2-chloro-phenyl)-5-trifluoromethyl-oxazole-4-carboxylic acid above, 2-(2-trifluoromethoxy-phenyl)-5-trifluoromethyl-oxazole-4-carboxylic acid was prepared from 2-trifluoromethoxy-benzoyl chloride, amino-acetic acid methyl ester and trifluoroacetic anhydride. LCMS calcd for C12H5F6NO4 (m/e) 341, obsd 342 (M+H).

Preparation of 2-(2-methoxy-phenyl)-5-trifluoromethyl-oxazole-4-carboxylic acid

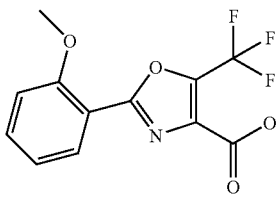

With a method similar to that used for the preparation of 2-(2-chloro-phenyl)-5-trifluoromethyloxazole-4-carboxylic acid above, 2-(2-methoxy-phenyl)-5-trifluoromethyl-oxazole-4-carboxylic acid was prepared from 2-methoxy-benzoyl chloride, amino-acetic acid methyl ester and trifluoroacetic anhydride. LCMS calcd for C12H8F3NO4 (m/e) 287, obsd 288 (M+H).

Preparation of 2-cyclohexyl-5-trifluoromethyl-oxazole-4-carboxylic acid

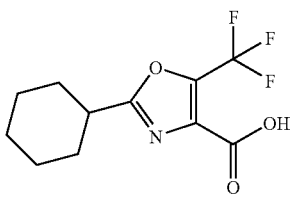

With a method similar to that used for the preparation of 2-(2-chloro-phenyl)-5-trifluoromethyloxazole-4-carboxylic acid above, 2-cyclohexyl-5-trifluoromethyl-oxazole-4-carboxylic acid was prepared from cyclohexanecarbonyl chloride, amino-acetic acid methyl ester and trifluoroacetic anhydride. LCMS calcd for C11H2F3NO3 (m/e) 263, obsd 264 (M+H).

Preparation of 2-phenyl-4-trifluoromethyl-oxazole-5-carboxylic acid

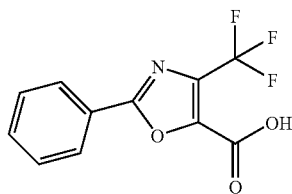

2-Phenyl-4-trifluoromethyl-oxazole-5-carboxylic acid was prepared according to the procedure described in *Bioorg. Med. Chem. Lett.* 2003, 13, 1517. A solution of 2-chloro-4,4,4-trifluoro-3-oxo-butyric acid ethyl ester (436 mg, 2 mmol) and benzamide (484 mg, 4 mmol) in ethanol (6 mL) in a sealed tube was heated at 120 degrees for 30 h. After cooling to room temperature, the reaction mixture was concentrated and purified by flash chromatography (silica gel 60, 230-400 mesh, 0-80% ethyl acetate in hexane for 25 min) to give 4-hydroxy-2-phenyl-4-trifluoromethyl-4,5-dihydro-oxazole-5-carboxylic acid ethyl ester as an off-white solid (229 mg, 38% yield). LCMS calcd for C13H12F3NO4 (m/e) 303, obsd 304 (M+H). The ester was dehydrated by heating with 2 mL of phosphorus oxychloride at 80 degree overnight. The reaction mixture was cooled and concentrated. The resulting residue was mixed with THF and concentrated again to remove remaining POCl3. The oily residue was quenched with water and extracted with DCM (2×). The organic layer was concentrated. The crude product was purified by flash chromatography (silica gel 60, 230-400 mesh, 0-50% ethyl acetate in hexane for 25 min) to yield 2-phenyl-4-trifluoromethyl-oxazole-5-carboxylic acid ethyl ester as an off-white solid (160 mg, 75% yield). The ester was hydrolyzed by stirring with lithium hydroxide monohydrate in a mixed solvent of 3:1:1 of THF:MeOH:water (3 mL) at RT for 4 h. The reaction was concentrated and water was added. The pH of the solution was adjusted to ~1-2 with 1 N HCl. The white precipitate was collected by centrifugation and washed with water. After drying under vacuum, 2-phenyl-4-trifluoromethyl-oxazole-5-carboxylic acid was obtained as a white solid (141 mg, 98% yield. LCMS calcd for C11H6F3NO3 (m/e) 257, obsd 258 (M+H).

Preparation of 2-(2-methoxy-phenyl)-4-trifluoromethyl-oxazole-5-carboxylic acid

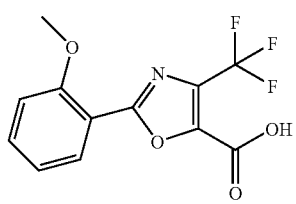

With a method similar to that used for the preparation of 2-phenyl-4-trifluoromethyl-oxazole-5-carboxylic acid above, 2-(2-methoxy-phenyl)-4-trifluoromethyl-oxazole-5-carboxylic acid was prepared from 2-chloro-4,4,4-trifluoro-3-oxo-butyric acid ethyl ester and 2-methoxy-benzamide. LCMS calcd for C12H8F3NO4 (m/e) 287, obsd 288 (M+H).

Preparation of 2-[2-(2-methoxy-ethoxy)-phenyl]-4-trifluoromethyl-oxazole-5-carboxylic acid

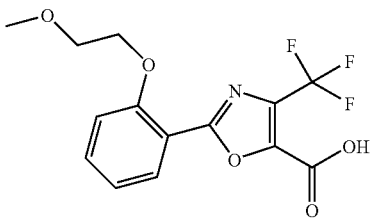

With a method similar to that used for the preparation of 2-phenyl-4-trifluoromethyl-oxazole-5-carboxylic acid above, 2-[2-(2-methoxy-ethoxy)-phenyl]-4-trifluoromethyl-oxazole-5-carboxylic acid was prepared from 2-chloro-4,4,4-trifluoro-3-oxo-butyric acid ethyl ester, 2-hydroxy-benzamide and 1-bromo-2-methoxy-ethane. LCMS calcd for C14H12F3NO5 (m/e) 331, obsd 332 (M+H).

Preparation of
5-cyclohexyl-2-methyl-furan-3-carboxylic acid

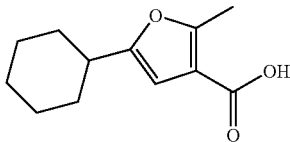

A solution of methyl cyclohexylacetate (1.56 g, 10 mmol) in 25 mL anhydrous ether was stirred at −78° C. under argon. DIBAL (1M in hexane, 11 mL, 11 mmol) was added dropwise over 45 minutes and the reaction mixture was stirred for an additional 1 hour. A solution of potassium sodium tartrate tetrahydrate (6 g, 12.2 mmol) in 25 mL water was added and the mixture stirred at room temperature overnight. After dilution with ether, the organic layer was washed with 0.5 N HCl, saturated sodium bicarbonate and saturated sodium chloride, dried over sodium sulfate, filtered and concentrated to give cyclohexyl-acetaldehyde (1.17 g, 93%).

A solution of the above cyclohexyl-acetaldehyde (1.04 g, 8.25 mmol) and ethyl acetoacetate (0.873 mL, 6.85 mmol) in 300 mL ethanol was stirred in an ice bath as piperidine (7.3 uL, 73 umol) in 380 uL ethanol was added. The mixture was stirred in the ice bath for 5 hours and placed in a refrigerator for 16 hours. The reaction mixture was diluted with 50 mL ether and extracted with saturated sodium chloride (3×30 mL containing 2 drops AcOH). The brine layers were back-extracted with ether (2×40 mL). The combined ether layers were washed with brine (30 mL), dried over sodium sulfate, filtered and evaporated to give 2-acetyl-4-cyclohexyl-but-2-enoic acid ethyl ester (1.79 g).

A solution of 2-acetyl-4-cyclohexyl-but-2-enoic acid ethyl ester (1.79 g, 7.52 mmol) in 40 mL CCl4 was added to a slurry of NBS (1.338 g, 7.52 mmol) in 40 mL CCl4. The mixture was refluxed under argon for 12 hours, stirred at room temperature for 68 hours and then cooled in an ice bath. The precipitated solid was filtered off and the filtrate was evaporated to an oil that was purified by short-path distillation (165-185° C., 1 mm Hg) yielding 5-cyclohexyl-2-methyl-furan-3-carboxylic acid ethyl ester (1.36 g, 77%).

A solution of 5-cyclohexyl-2-methyl-furan-3-carboxylic acid ethyl ester (143 mg, 0.605 mmol) and 2N sodium hydroxide (1.5 mL, 3.0 mmol) in 3 mL ethanol and 1.5 mL water was heated to reflux for 1 hour. The reaction mixture was cooled, pH adjusted to 1 with 1N HCl and extracted with CH2Cl2 (5×40 mL). The combined organic layers were dried over sodium sulfate, filtered and evaporated to give 5-cyclohexyl-2-methyl-furan-3-carboxylic acid (96 mg, 76%).

Preparation of
5-cyclohexyl-2-ethyl-furan-3-carboxylic acid

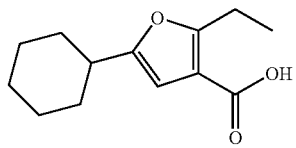

Similar to the procedure above, except that ethyl 3-oxovalerate was used instead of ethyl acetoacetate, 5-cyclohexyl-2-ethyl-furan-3-carboxylic acid was prepared as a powder (49 mg).

Preparation of 1-phenyl-3-trifluoromethyl-1H-pyrazole-4-carboxylic acid

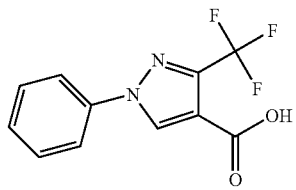

A mixture of 3-trifluoromethyl-1H-pyrazole-4-carboxylic acid ethyl ester (1.25 g, 6.0 mmol), copper (I) iodide (0.342 g, 1.8 mmol) and potassium carbonate (0.58 g, 4.2 mmol) in toluene (6 mL) in a round bottom flask was purged with argon. To the reaction mixture was then added iodobenzene (0.81 mL, 7.2 mmol) and racemic trans-N,N'-dimethyl-cyclohexane-1,2-diamine (0.58 mL, 3.6 mmol). The slurry was heated under Ar in an oil bath at 110° C. for 24 hours. After cooling to room temperature, the reaction mixture was diluted with ethyl acetate and filtered through a bed of celite. After washing the celite with ethyl acetate, the filtrates were combined and concentrated to give a crude which was purified by silica gel chromatography (Isco 120 g column, 0 to 30% ethyl acetate/hexanes) to give 1-phenyl-3-trifluoromethyl-1H-pyrazole-4-carboxylic acid ethyl ester (1.40 g, 82%) as an off-white solid. The NMR spectrum obtained on the sample is compatible with its structure.

A mixture of 1-phenyl-3-trifluoromethyl-1H-pyrazole-4-carboxylic acid ethyl ester (160 mg, 0.56 mmol) and 1N aqueous sodium hydroxide solution (2.3 mL, 2.3 mmol) in methanol (10 mL) was stirred at room temperature overnight. The reaction mixture was acidified to pH~2 with 1N aqueous hydrochloric acid and concentrated to give 1-phenyl-3-trifluoromethyl-1H-pyrazole-4-carboxylic acid as an off-white solid, which was directly used without further purification. LCMS calcd for C11H7F3N2O (m/e) 256, obsd 257 (M+H).

Preparation of 5-phenyl-2-(2,2,2-trifluoro-ethyl)-2H-pyrazole-3-carboxylic acid

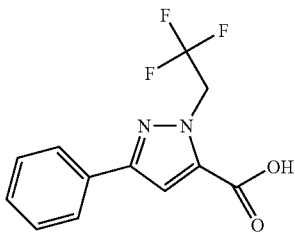

To a mixture of 5-phenyl-2H-pyrazole-3-carboxylic acid ethyl ester (500 mg, 2.31 mmol) in N,N-dimethylformamide (30 mL) at 0° C. was added sodium hydride (60% in mineral oil, 110 mg, 2.75 mmol). The mixture was stirred at 0° C. for 10 minutes and then at room temperature for 40 minutes. After the reaction mixture was re-cooled to 0° C., 2,2,2-trifluoro-methanesulfonic acid 2,2,2-trifluoro-ethyl ester (500 mg, 2.39 mmol) was added dropwise. The mixture was warmed up to room temperature and stirred overnight. The reaction was quenched carefully with ice water and neutralized with 1N aqueous hydrochloric acid. The mixture was extracted with methylene chloride and the organic layer was dried over sodium sulfate. Filtration and concentration gave a crude which was purified by silica gel chromatography (Isco 120 g column, 11% ethyl acetate/hexanes) to give 5-phenyl-2-(2,2,2-trifluoro-ethyl)-2H-pyrazole-3-carboxylic acid ethyl ester (360 mg, 52%) as a white solid. The NMR spectrum obtained on the sample is compatible with its structure.

A mixture of 5-phenyl-2-(2,2,2-trifluoro-ethyl)-2H-pyrazole-3-carboxylic acid ethyl ester (360 mg, 1.21 mmol) and 1N aqueous sodium hydroxide solution (3.6 mL, 3.6 mmol) in methanol (10 mL) was stirred at room temperature overnight. The reaction mixture was acidified to pH~2 with 1N aqueous hydrochloric acid and concentrated to give 5-phenyl-2-(2,2,2-trifluoro-ethyl)-2H-pyrazole-3-carboxylic acid as an off-white solid, which was directly used in the next step reaction without further purification. LCMS calcd for C12H9F3N2O (m/e) 270, obsd 271 (M+H).

Preparation of N-(2-methoxyethyl)-N-methylpyrazine-2,5-diamine

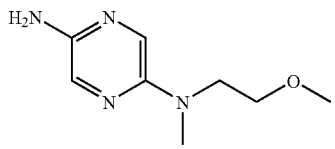

A mixture of methyl 5-chloropyrazine-2-carboxylate (1.0 g, 5.797 mmol) and N-methyl-N-(2-methoxy)ethyl amine (2.0 mL, 18.6 mmol) was heated in an oil bath at 75° C. for 10 minutes. The reaction mixture was evaporated to dryness and the residue was triturated with dry ether (50 mL) to give a solid as methyl 5-[N-methyl-N-(2-methoxyethyl)]aminopyrazine-2-carboxylate hydrochloride (1.55 g, 100%). LCMS calcd for C10H15N3O3 (m/e) 225, obsd 226.1 (M+H).

The above solid (1.55 g) was dissolved in methanol (20 mL) and aqueous (1N) sodium hydroxide solution was added (12 mL). The mixture was stirred at 45° C. for 60 minutes. The reaction mixture was evaporated to dryness to give a yellow waxy solid (about 3.0 g) as a sodium 5-[N-methyl-N-(2-methoxyethyl)]aminopyrazine-2-carboxylate. LCMS calcd for C9H13N3O3 (m/e) 211, obsd 212.1 (M+H).

The above crude sodium salt was suspended in DMF (25 mL) and diphenylphosphorylazide (2.0 mL, 9.3 mmol) was added. The mixture was stirred at room temperature for 18 hrs to give a clear solution. Solvents were evaporated under vacuum and the residue was extracted with ethyl acetate (75 mL) and water (50 mL). The aqueous layer was further extracted with ethyl acetate (50 mL). The combined organic layer was dried over sodium sulfate and solvents were evaporated to give amber crystals (1.83 g). The crystalline material was dissolved in toluene (20 mL) and benzyl alcohol was added. The mixture was stirred at 95° C. for 60 minutes. The resulting solution was cooled down to room temperature and the solution was concentrated to two thirds of the volume until crystal material appeared. The solid was filtered and washed with toluene, then with ether, to give white crystals as 5-[N-(2-methoxyethyl)-N-methylamino]pyrazine-2-carbamic acid benzyl ester (705 mg, 39%). LCMS calcd for C16H20N4O3 (m/e) 316, obsd 317.2 (M+H).

The above carbamic acid benzyl ester (316 mg, 1.0 mmol) was suspended in a mixture of methanol (25 mL) and THF (5 mL) containing 5% palladium on carbon (60 mg). The solution was placed under an atmosphere of hydrogen (hydrogen balloon) for one hour. The mixture was filtered through a thin layer of Celite and the solution was evaporated to give a green oil as N-(2-methoxyethyl)-N-methylpyrazine-2,5-diamine (180 mg, 100%). LCMS calcd for C8H14N4O (m/e) 182, obsd 183.1 (M+H).

Preparation of N-(tetrahydropyran-4-yl)pyrazine-2,5-diamine

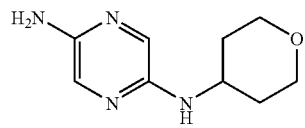

A mixture of 4-aminotetrahydropyran (500 mg, 4.94 mmol) and methyl 2-chloropyrazine-5-carboxylate (770 mg, 4.46 mmol) in DMF (5 mL) containing N,N-diisopropylethylamine (1.0 mL, 5.7 mmol) was stirred at 55° C. for 17 hrs. The reaction mixture was concentrated and the residue was partitioned between ether (25 mL) and hydrochloric acid (1N, 25 mL). The aqueous layer was further extracted with ether (25 mL). The resulting aqueous layer was first treated with sodium chloride (10 g) and then extracted with methylene chloride (3×50 mL). The organic layer was washed with brine and dried over sodium sulfate. Solvents were evaporated to give an oil which slowly crystallized as methyl 2-(N-tetrahydropyran-4-yl)-aminopyrazine-5-carboxylate (900 mg, 85%). MS calcd for C11H15N3O3 (m/e) 237, obsd 238.1 (M+H).

The above methyl ester (877 mg, 3.7 mmol) was dissolved in methanol (10 mL) and treated with solid sodium hydroxide (300 mg, 7.5 mmol) and water (0.6 mL). The solution was stirred at 50° C. for 60 minutes. The reaction mixture was evaporated to dryness and the residue was twice dissolved in toluene (2×25 mL) and evaporated to give a solid as a sodium salt. This salt was suspended in DMF (15 mL) and diphenylphosphorylazide (1.1 mL, 5.11 mol) was added. The mixture was stirred at room temperature overnight to give a clear solution. Solvents were evaporated and the residue was partitioned between ethyl acetate (50 mL) and water (25 mL). The organic layer was dried over sodium sulfate and solvents were evaporated to give an oil (900 mg). This oil was treated with benzyl alcohol (0.8 mL, 7.7 mmol) and heated at 95° C. with stirring for 45 minutes. The resulting solid was dissolved in a minimum volume of methylene chloride and loaded to a Biotage flash column eluted with gradient ethyl acetate in hexanes (25% to 100%). The desired fractions were concentrated to give yellowish crystals as 5-(N-tetrahydropyran-4-yl)aminopyrazine-2-carbamic acid benzyl ester (605 mg, 49.7%). MS calcd for C17H20N4O3 (m/e) 328, obsd 329.3 (M+H).

The above carbamic acid methyl ester (200 mg, 0.609 mol) was suspended in methanol (10 mL) and THF (4 mL) containing 10% palladium on carbon (40 mg). The mixture was placed under an atmosphere of hydrogen (hydrogen balloon) at room temperature for 90 minutes. The mixture was filtered through a thin layer of Celite. The filtrate was evaporated to dryness go give a yellow solid as 5-(N-tetrahydropyran-4-yl)pyrazine-2,5-diamine (120 mg, 100%). MS calcd for C9H14N4O (m/e) 194, obsd 195.1 (M+H).

Preparation of N²-[cis-3-(tert-butyl-dimethyl-silanyloxy)-cyclopentyl]-pyridine-2,5-diamine

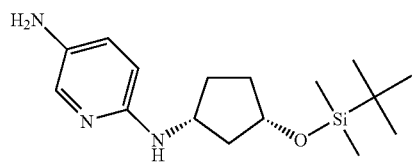

To a 20 mL vial containing cis-3-(tert-butyl-dimethyl-silanyloxy)-cyclopentylamine, prepared according to literature reference (see Chen, et al US 2004/0204427 A1), (580 mg, 2.69 mmol) was added DMF (10 mL), 2-chloro-5-nitro-pyridine (428 mg, 2.69 mmol), and TEA (1.5 mL). The vessel was purged with Ar, sealed, heated to 75° C. for 4.5 hr, cooled to room temperature and allowed to stir over the weekend (60 hr). The reaction mixture was heated again at 75° C. for an additional 6 hr and then allowed to cool to RT overnight (18 hr). The reaction mixture was concentrated and redissolved in DMF (10 mL). 2 eq of K$_2$CO$_3$ was added (744 mg) and heated to 70° C. for 1 hr. The reaction mixture was concentrated, supported on silica gel, and purified by flash chromatography using an Analogix with a 80 g Redisep silica gel column at 60 mL/min with increasing concentrations of Et$_2$O in hexane (0-5 min: 0%, 5-25 min: 0-20%, 25-40 min: 30%, 40-65 min: 30-100%). The appropriate fractions were collected and dried producing a clear oil, 490.8, 54.0% (LCMS 4.23 min, 338 (M+H), calcd. C16H27N3O3Si (m/e) 337, 50-100% ACN in H$_2$O/HCOOH, C18, APCI). The nitropyridyl compound was transferred to a PARR vessel with MeOH (10 mL), Pd/C (10%) was added and the vessel was pressurized with H$_2$ at 54 psi. After 3 hr the reaction mixture was filtered through a bed of celite and concentrated to dryness twice from DCM. The purple black material was used immediately for amide coupling (LCMS 2.94 min, 308 (M+H), calcd. C16H27N3O3Si (m/e) 307, 10-100% ACN in H$_2$O/HCOOH 0.3%, C18, APCI).

Preparation of N²-[trans-3-(tert-butyl-dimethyl-silanyloxy)-cyclopentyl]-pyridine-2,5-diamine

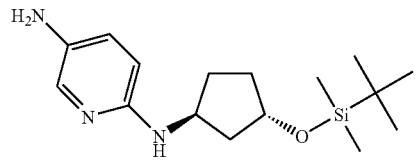

With a method similar to that used for the preparation of N²-[cis-3-(tert-butyl-dimethyl-silanyloxy)-cyclopentyl]-pyridine-2,5-diamine above, N²-[trans-3-(tert-butyl-dimethyl-silanyloxy)-cyclopentyl]-pyridine-2,5-diamine was prepared from 2-chloro-5-nitro-pyridine and trans-3-(tert-butyl-dimethyl-silanyloxy)-cyclopentyl, prepared according to literature reference (see Chen, et al US 2004/0204427 A1). (LCMS 3.15 min, 308 (M+H), calcd. C16H27N3O3Si (m/e) 307, 0-100% ACN in H$_2$O/HCOOH 0.3%, Echelon C18, ESI).

Preparation of N²-[(1S,3S)-3-(tert-butyl-dimethyl-silanyloxy)-cyclopentyl]-pyridine-2,5 diamine

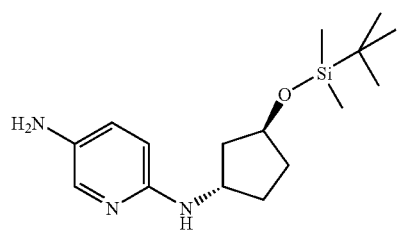

With a method similar to that used for the preparation of N²-[cis-3-(tert-butyl-dimethyl-silanyloxy)-cyclopentyl]-pyridine-2,5-diamine, N²-[(1S,3S)-3-(tert-butyl-dimethyl-silanyloxy)-cyclopentyl]-pyridine-2,5-diamine was prepared from trans-(1S,3S)-3-(tert-butyl-dimethyl-silanyloxy)-cyclopentylamine and 2-chloro-5-nitro-pyridine. LCMS calcd. for C16H29N3OSi (m/e) 307, observed 308 (M+H).

Preparation of N²-[trans-(1R,3R)-3-(tert-butyl-dimethyl-silanyloxy)-cyclopentyl]-(5-nitro-pyridin-2-yl)-amine

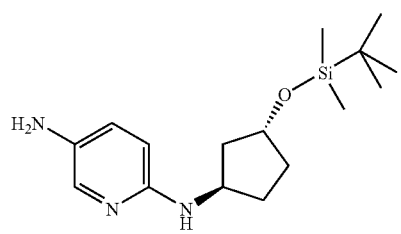

With a method similar to that used for the preparation of N²[cis-3-(tert-butyl-dimethyl-silanyloxy)-cyclopentyl]-pyridine-2,5-diamine, N²-[(1R,3R)-3-(tert-butyl-dimethyl-silanyloxy)-cyclopentyl]-pyridine-2,5-diamine was prepared from trans-(1R,3R)-3-(tert-butyl-dimethyl-silanyloxy)-cyclopentylamine and 2-chloro-5-nitro-pyridine. LCMS calcd. for C16H29N3OSi (m/e) 307, observed 308 (M+H).

Preparation of 2-phenyl-5-trifluoromethyl-oxazole-4-carboxylic acid {6-((1S,3S)-[3-(tert-butyl-dimethyl-silanyloxy)-cyclopentylamino]-pyridin-3-yl}-amide

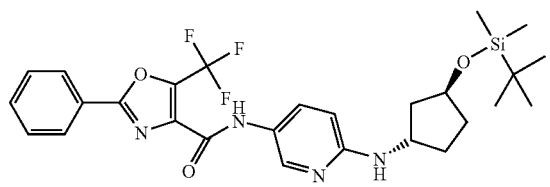

With a method similar to that used for the preparation of 2-phenyl-5-trifluoromethyl-oxazole-4-carboxylic acid (6-cyclopentylamino-pyridin-3-yl)-amide above, 2-phenyl-5-trifluoromethyl-oxazole-4-carboxylic acid {6-((1S,3S)-[3-(tert-butyl-dimethyl-silanyloxy)-cyclopentylamino]-pyridin-3-yl}-amide was prepared from 2-phenyl-5-trifluoromethyl-oxazole-4-carboxylic acid and $N^2$-[(1S,3S)-3-(tert-butyl-dimethyl-silanyloxy)-cyclopentyl]-pyridine-2,5-diamine (prepared in situ by the reduction of $N^2$-[trans-(1S,3S)-3-(tert-butyl-dimethyl-silanyloxy)-cyclopentyl]-(5-nitro-pyridin-2-yl)-amine following a method similar to that used for the preparation of $N^2$-cyclopentyl-pyridine-2,5-diamine above). Red solid. LCMS for $C_{27}H_{33}F_3N_4O_3Si$ (m/e) calculated 546, observed 547 (M+H).

Preparation of 2-phenyl-5-trifluoromethyl-oxazole-4-carboxylic acid {6-((1R,3R)-[3-(tert-butyl-dimethyl-silanyloxy)-cyclopentylamino]-pyridin-3-yl}-amide

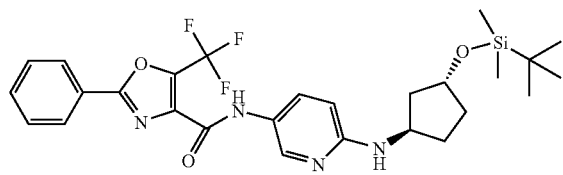

With a method similar to that used for the preparation of 2-phenyl-5-trifluoromethyl-oxazole-4-carboxylic acid {6-((1S,3S)-[3-(tert-butyl-dimethyl-silanyloxy)-cyclopentylamino]-pyridin-3-yl}-amide above, 2-phenyl-5-trifluoromethyl-oxazole-4-carboxylic acid {6-((1R,3R)-[3-(tert-butyl-dimethyl-silanyloxy)-cyclopentylamino]-pyridin-3-yl}-amide was prepared from 2-phenyl-5-trifluoromethyl-oxazole-4-carboxylic acid and $N^2$-[(1R,3R)-3-(tert-butyl-dimethyl-silanyloxy)-cyclopentyl]-pyridine-2,5-diamine (prepared in situ by the reduction of $N^2$-[trans-(1R,3R)-3-(tert-butyl-dimethyl-silanyloxy)-cyclopentyl]-(5-nitro-pyridin-2-yl)-amine following a method similar to that used for the preparation of $N^2$-cyclopentyl-pyridine-2,5-diamine above). LCMS for $C_{27}H_{33}F_3N_4O_3Si$ (m/e) calculated 546, observed 547 (M+H).

Preparation of 1-(6-nitropyridine-3-yl)-pyrrolidin-3-ol

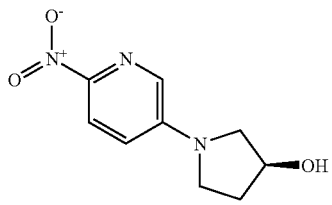

A solution of 2-nitro-5-bromopyridine (320 mg, 2.02 mmol) in EtOH (6 mL) was treated with diisopropylethylamine (710 µL, 520 mg, 4.04 mmol) and (S)-3-hydroxypyrrolidinol (350 mg, 4.04 mmol). The mixture was heated in a sealed tube at 85° C. for 21.5 h then cooled and partitioned between $CH_2Cl_2$ and water. The organic layer was dried over $Na_2SO_4$, filtered and concentrated and the residue was chromatographed on a silica gel column with a 40-100% EtOAc in hexanes to 0-30% THF in EtOAc gradient to afford the product, as a yellow solid (200 mg, 47% yield). HRMS m/z calcd for $C_9H_{11}N_3O_3$ [M+H]$^+$: 210.0873; Found: 210.0873.

Preparation of 5-(3-(S)-methoxy-pyrrolidin-1-yl)-2-nitro-pyridine

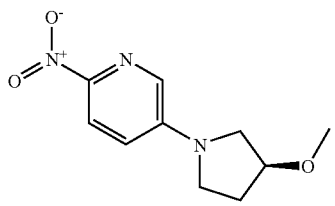

A solution of 5-(3-(S)-hydroxypyrrolidinol)-2-nitropyridine (200 mg, 0.96 mmol) in anhydrous THF was treated with MeI (178 µL, 2.88 mmol) and then NaH, 60% in mineral oil, (57 mg, 1.44 mmol) at room temperature. After stirring overnight at room temperature the reaction mixture was partitioned between EtOAc and water. The organic layer was dried over $Na_2SO_4$, filtered and concentrated. Precipitation from $CH_2Cl_2$ with excess of hexanes afforded the product, as a yellow solid (170 mg, 80% yield). HRMS m/z calcd for $C_{10}H_{11}N_3O_3$ [M+Na]$^+$: 246.0849; Found: 246.0849.

Preparation of (2-methoxyethyl)-methy-(6-nitropyridin-3-yl)-amine

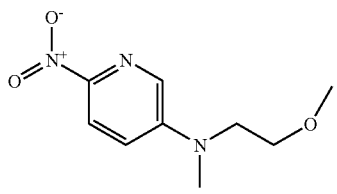

A solution of 2-nitro-5-bromopyridine (500 mg, 3.15 mmol) in EtOH (15 mL) was treated with methoxyethyl-N- methylamine (1.12 g, 12.6 mmol) and diisopropylethylamine (2.2 mL, 12.6 mmol). The resulting mixture was then heated in a sealed tube at 90° C. for 4 days then cooled and partitioned between EtOAc and water. The organic layer was dried over Na$_2$SO$_4$, filtered and concentrated. The residue was chromatographed on a silica gel column with a 40-100% EtOAc in hexanes gradient to afford the product as a thick yellow oil that crystallized slowly upon standing (270 mg, 41% yield). HRMS m/z calcd for C$_9$H$_{13}$N$_3$O$_3$ [M+Na]$^+$: 234.0849; Found: 234.0850.

Preparation of 1-(5-nitro-pyridin-2-yl)-azetidin-3-ol

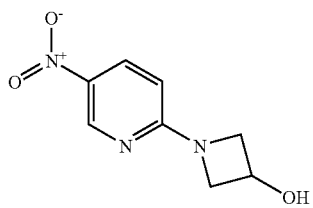

2-Bromo-5-nitropyridine (406 mg, 2 mmol), 3-hydroxyazetidine hydrochloride (199 mg, 2 mmol), and finely ground potassium carbonate (828 mg, 6 mmol) were heated to 80° C. in 20 mL anhydrous DMF for 5 hrs. The mixture was diluted with EtOAc, extracted with H$_2$O and dried over MgSO$_4$. The EtOAc layer was filtered, evaporated to dryness and used without further purification. ES-MS calcd for C8H9N3O3 (m/e) 195.18, obsd 196.2 (M+H).

Preparation of (2-ethoxy-ethyl)-methyl-(5-nitro-pyridin-2-yl)-amine

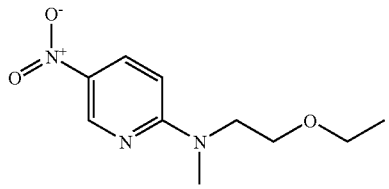

(2-Hydroxy-ethyl)-methyl-(5-nitro-pyridin-2-yl)-amine (197 mg, 1 mmol) in THF (5 mL) and DMF (2 mL) was stirred with 60% NaH in oil (48 mg, 1.2 mmol) for 1 hr. The mixture was cooled and to this was added ethyl iodide (120 uL, 1.5 mmol). The reaction was allowed to stir overnight. The mixture was diluted with EtOAc, extracted with H$_2$O and dried over MgSO$_4$. The EtOAc layer was filtered, evaporated to dryness and used without further purification. Yield: 155 mg. ES-MS calcd for C10H15N3O3 (m/e) 225.25, obsd 225.1 (M+H).

Preparation of 2-(3-methoxy-azetidin-1-yl)-5-nitro-pyridine

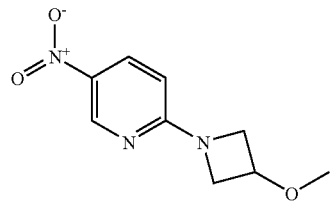

1-(5-Nitro-pyridin-2-yl)-azetidin-3-ol (97.5 mg, 0.5 mmol) was treated with 60% NaH in oil (40 mg, 1 mmol) and methyl iodide (125 uL, 2 mmol) as above to yield 125 mg of crude product that was used without further purification. ES-MS calcd for C9H11N3O3 (m/e) 209.21, obsd 210 (M+H).

Preparation of sec-butyl-(5-nitro-pyridin-2-yl)-amine

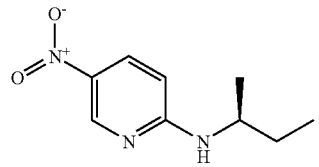

2-Bromo-5-nitropyridine (341 mg, 1.68 mmol), (S)-(+)-sec butylamine (123 mg, 1.68 mmol), and finely ground potassium carbonate (707 mg, 5.1 mmol) were heated to 80° C. in 15 mL anhydrous DMF for 3.5 hrs. The mixture was diluted with EtOAc, extracted with H$_2$O and dried over MgSO$_4$. The EtOAc layer was filtered, evaporated to dryness and purified by flash chromatography to yield 233 mg. ES-MS calcd for C9H13N3O2 (m/e) 195.22, obsd 196.1 (M+H).

Preparation of 2-(3-ethoxy-azetidin-1-yl)-5-nitro-pyridine

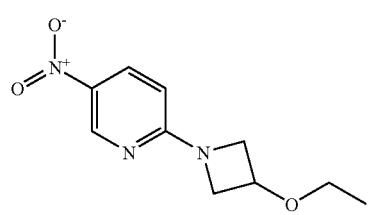

1-(5-Nitro-pyridin-2-yl)-azetidin-3-ol (97.5 mg, 0.5 mmol) was treated with 60% NaH in oil (60 mg, 1.5 mmol) and ethyl iodide (400 uL, 5 mmol) as above to yield 62 mg of product following purification by flash chromatography. ES-MS calcd for C10H13N3O3 (m/e) 223.23, obsd 224.1 (M+H).

Preparation of (2-cyclopropylmethoxy-ethyl)-methyl-(5-nitro-pyridin-2-yl)-amine

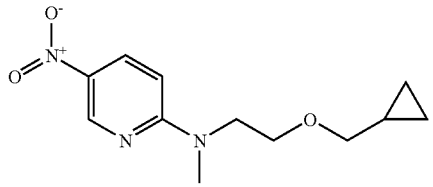

(2-Hydroxy-ethyl)-methyl-(5-nitro-pyridin-2-yl)-amine (98.5 mg, 0.5 mmol) in THF (10 mL) and DMF (2 mL) was stirred with 60% NaH in oil (32 mg, 0.8 mmol) for 1 hr. The mixture was cooled and to this was added bromomethylcyclopropane (0.685 mg, 5 mmol). The reaction mixture was allowed to stir overnight. The mixture was diluted with EtOAc, extracted with H$_2$O and dried over MgSO$_4$. The EtOAc was filtered, evaporated to dryness and used without further purification. Yield: 82 mg. ES-MS calcd for C12H17N3O3 (m/e) 251.29, obsd 252.1 (M+H).

Preparation of (2-ethoxy-ethyl)-methyl-(5-nitro-pyrimidin-2-yl)-amine

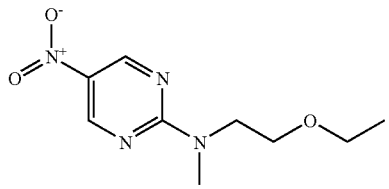

(2-Hydroxy-ethyl)-methyl-(5-nitro-pyrimidin-2-yl)-amine (198 mg, 1 mmol) in THF (15 mL) and DMF (3 mL) was stirred with 60% NaH in oil (60 mg, 1.75 mmol) for 1 hr. The mixture was cooled and to this was added ethyl iodide. The reaction mixture was allowed to stir overnight. The mixture was diluted with EtOAc, extracted with H$_2$O and dried over MgSO$_4$. The EtOAc was filtered, evaporated to dryness and used without further purification. Yield: 75 mg. ES-MS calcd for C9H14N4O3 (m/e) 226.24, obsd 227 (M+H).

Preparation of [1-(5-nitro-pyridin-2-yl)-azetidin-3-yloxy]-acetic acid tert-butyl ester

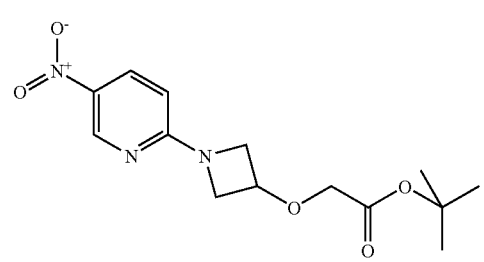

1-(5-Nitro-pyridin-2-yl)-azetidin-3-ol (176 mg, 0.9 mmol) was treated with 60% NaH in oil (108 mg, 2.7 mmol) and tert-butyl bromoacetate (199.7 uL, 1.35 mmol) as above to yield 210 mg of a yellow solid. ES-MS calcd for C14H19N3O5 (m/e) 309.32, obsd 310.2 (M+H).

Preparation of [1-(5-nitro-pyridin-2-yl)-pyrrolidin-3-yloxy]-acetic acid tert-butyl ester

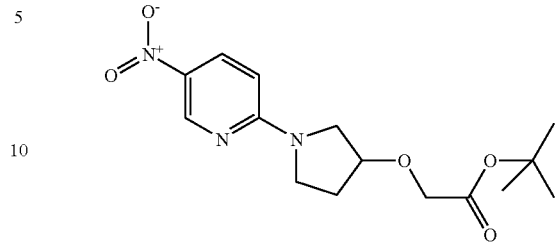

1-(5-Nitro-pyridin-2-yl)-pyrrolidin-3-ol (340 mg, 1.62 mmol) was treated with 60% NaH in oil (130 mg, 3.25 mmol) and tert-butyl bromoacetate (1.2 mL, 8.13 mmol) as above to yield 280 mg of a yellow solid following flash chromatography. ES-MS calcd for C15H21N3O5 (m/e) 323.35, obsd 324.1 (M+H).

Preparation of {2-[methyl-(5-nitro-pyridin-2-yl)-amino]-ethoxy}-acetic acid tert-butyl ester

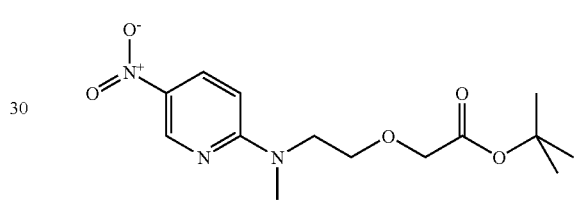

(2-Hydroxy-ethyl)-methyl-(5-nitro-pyridin-2-yl)-amine (350 mg, 1.77 mmol) in THF (15 mL) and DMF (2 mL) was stirred with 60% NaH in oil (142 mg, 4.44 mmol) for 1 hr. The mixture was cooled and to this was added tert-butyl bromoacetate (1.31 mL, 8.88 mmol). The reaction mixture was allowed to stir overnight. The mixture was diluted with EtOAc, extracted with H$_2$O and dried over MgSO$_4$. The EtOAc layer was filtered, evaporated to dryness and yielded 262 mg following flash chromatography. ES-MS calcd for C14H21N3O5 (m/e) 311.34, obsd 312 (M+H).

Preparation of methyl-(3-methyl-butyl)-(5-nitro-pyridin-2-yl)-amine

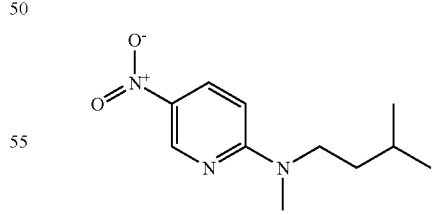

2-Chloro-5-nitropyridine (158 mg, 1 mmol), N-methylisoamylamine (101 mg, 1 mmol), and finely ground potassium carbonate (419 mg, 3 mmol) were heated to 80° C. in 10 mL anhydrous DMF for 3.5 hrs. The mixture was diluted with EtOAc, extracted with H$_2$O and dried over MgSO$_4$. The EtOAc layer was filtered, evaporated to dryness to yield 220 mg. ES-MS calcd for C11H17N3O2 (m/e) 223.28, obsd 224.1 (M+H).

Preparation of 3-[methyl-(5-nitro-pyridin-2-yl)-amino]-propionitrile

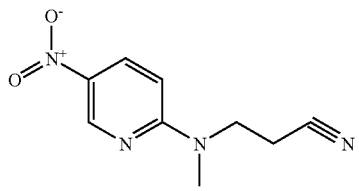

2-Chloro-5-nitropyridine (158 mg, 1 mmol), 3-methylamino-propionitrile (84 mg, 1 mmol), and finely ground potassium carbonate (414 mg, 3 mmol) were heated to 80° C. in 10 mL anhydrous DMF for 3.5 hrs. The mixture was diluted with EtOAc, extracted with H₂O and dried over MgSO₄. The EtOAc layer was filtered, evaporated to dryness. ES-MS calcd for C9H10N4O2 (m/e) 206.21, obsd 207.1 (M+H).

Preparation of bicyclo[2.2.1]hept-2-yl-(5-nitro-pyridin-2-yl)-amine

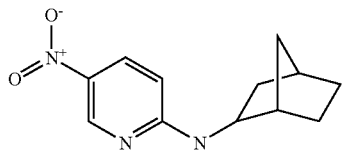

2-Chloro-5-nitropyridine (158 mg, 1 mmol), 2-aminonorbornane hydrochloride (147 mg, 1 mmol), and finely ground potassium carbonate (419 mg, 3 mmol) were heated to 80° C. in 10 mL anhydrous DMF for 3.5 hrs. The mixture was diluted with EtOAc, extracted with H₂O and dried over MgSO₄. The EtOAc was filtered, evaporated to dryness to yield 220 mg. ES-MS calcd for C12H15N3O2 (m/e) 233.21, obsd 234.1 (M+H).

Part II

Examples of Preferred Embodiments

Example 1

Preparation of 2-phenyl-5-trifluoromethyl-oxazole-4-carboxylic acid (6-morpholin-4-yl-pyridin-3-yl)-amide

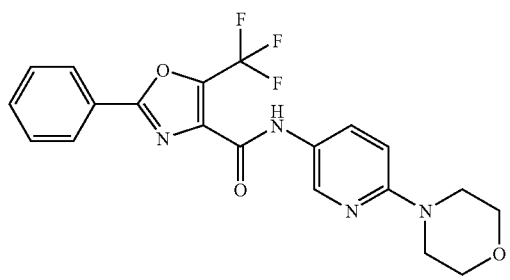

A mixture of 2-phenyl-5-trifluoromethyl-oxazole-4-carboxylic acid (1.58 g, 6.14 mmol), 6-morpholin-4-yl-pyridin-3-ylamine (1.0 g, 5.58 mmol), N-hydroxybenzotriazole (1.27 g, 8.37 mmol), and 1-ethyl-3-(3-dimethylaminopropyl)carbodiimide hydrochloride (1.6 g, 8.37 mmol) in anhydrous dichloromethane (20 mL) was stirred at room temperature overnight. After the reaction was complete, solvent was evaporated. The resulted mixture was mixed with water and extracted twice with ethyl acetate. The organic layers were collected, combined, washed with brine, dried over sodium sulfate, and then concentrated to give a solid. The crude product was purified by flash chromatography (Merck silica gel 60, 230-400 mesh, 0%-100% ethyl acetate in hexane) to gave 2-phenyl-5-trifluoromethyl-oxazole-4-carboxylic acid (6-morpholin-4-yl-pyridin-3-yl)-amide (1.15 g, 50%) as an off-white solid. LCMS calcd for C20H17F3N4O3 (m/e) 418, obsd 419 (M+H).

Example 2

Preparation of 2-phenyl-thiazole-4-carboxylic acid (6-morpholin-4-yl-pyridin-3-yl)-amide

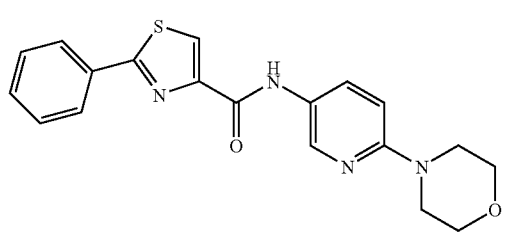

With a procedure similar to example 1 above, 2-phenyl-thiazole-4-carboxylic acid (6-morpholin-4-yl-pyridin-3-yl)-amide was prepared from 2-phenyl-thiazole-4-carboxylic acid and 6-morpholin-4-yl-pyridin-3-ylamine. LCMS calcd for C19H18N4O2S (m/e) 366, obsd 367 (M+H).

Example 3

Preparation of 4-phenyl-thiazole-2-carboxylic acid (6-morpholin-4-yl-pyridin-3-yl)-amide

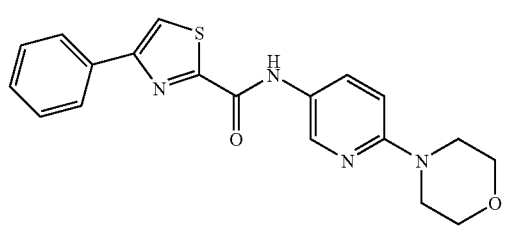

With a procedure similar to example 1 above, 4-phenyl-thiazole-2-carboxylic acid (6-morpholin-4-yl-pyridin-3-yl)-amide was prepared from 4-phenyl-thiazole-2-carboxylic acid and 6-morpholin-4-yl-pyridin-3-ylamine. LCMS calcd for C19H18N4O2S (m/e) 366, obsd 367 (M+H).

Example 4

Preparation of 2-phenyl-5-trifluoromethyl-oxazole-4-carboxylic acid (2-morpholin-4-yl-pyrimidin-5-yl)-amide

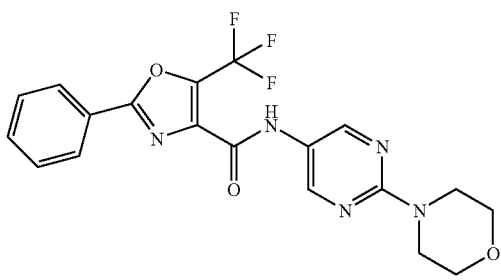

With a procedure similar to example 1 above, 2-phenyl-5-trifluoromethyl-oxazole-4-carboxylic acid (2-morpholin-4-yl-pyrimidin-5-yl)-amide was prepared from 2-phenyl-5-trifluoromethyl-oxazole-4-carboxylic acid and 2-morpholin-4-yl-pyrimidin-5-ylamine. LCMS calcd for C19H16F3N5O3 (m/e) 419, obsd 420 (M+H).

Example 5

Preparation of 5-methyl-2-phenyl-2H-[1,2,3]triazole-4-carboxylic acid (6-morpholin-4-yl-pyridin-3-yl)-amide

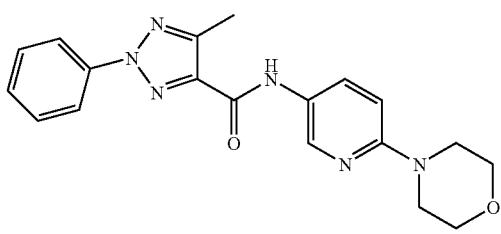

With a procedure similar to example 1 above, 5-methyl-2-phenyl-2H-[1,2,3]triazole-4-carboxylic acid (6-morpholin-4-yl-pyridin-3-yl)-amide was prepared from 5-methyl-2-phenyl-2H-[1,2,3]triazole-4-carboxylic acid and 6-morpholin-4-yl-pyridin-3-ylamine. LCMS calcd for C19H20N6O2 (m/e) 364, obsd 365 (M+H).

Example 6

Preparation of 5-bromo-2-phenyl-oxazole-4-carboxylic acid (6-morpholin-4-yl-pyridin-3-yl)-amide

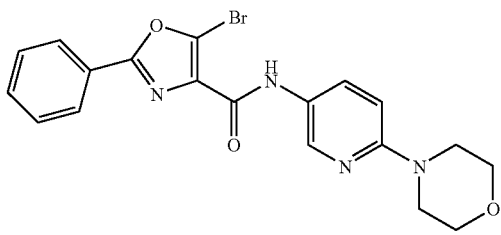

With a procedure similar to example 1 above, 5-bromo-2-phenyl-oxazole-4-carboxylic acid (6-morpholin-4-yl-pyridin-3-yl)-amide was prepared from 5-bromo-2-phenyl-oxazole-4-carboxylic acid and 6-morpholin-4-yl-pyridin-3-ylamine. LCMS calcd for C19H17BrN4O3 (m/e) 429, obsd 430 (M+H).

Example 7

Preparation of 5-phenyl-2-trifluoromethyl-furan-3-carboxylic acid (6-morpholin-4-yl-pyridin-3-yl)-amide

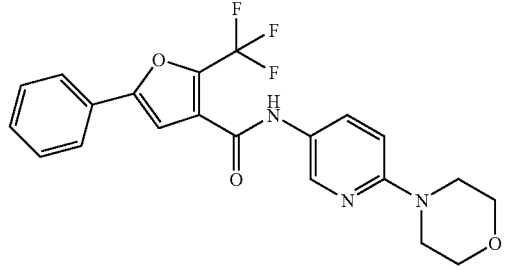

With a procedure similar to example 1 above, 5-phenyl-2-trifluoromethyl-furan-3-carboxylic acid (6-morpholin-4-yl-pyridin-3-yl)-amide was prepared from 5-phenyl-2-trifluoromethyl-furan-3-carboxylic acid and methyl-(6-morpholin-4-yl-pyridin-3-yl)-amine. LCMS calcd for C21H18F3N3O3 (m/e) 417, obsd 418 (M+H).

Example 8

Preparation of 5-chloro-2-phenyl-oxazole-4-carboxylic acid (6-morpholin-4-yl-pyridin-3-yl)-amide

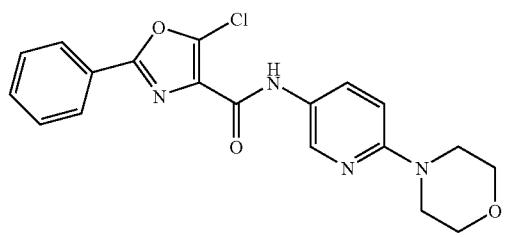

With a procedure similar to example 1 above, 5-chloro-2-phenyl-oxazole-4-carboxylic acid (6-morpholin-4-yl-pyridin-3-yl)-amide was prepared from 5-chloro-2-phenyl-oxazole-4-carboxylic acid and methyl-(6-morpholin-4-yl-pyridin-3-yl)-amine. LCMS calcd for C19H17ClN4O3 (m/e) 384, obsd 385 (M+H).

Example 9

Preparation of 2-phenyl-5-trifluoromethyl-oxazole-4-carboxylic acid {6-[(2-methoxy-ethyl)-methyl-amino]-pyridin-3-yl}-amide

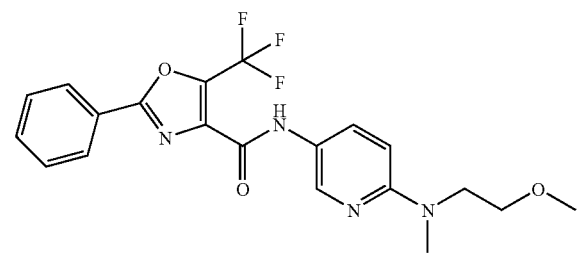

With a procedure similar to example 1 above, 2-phenyl-5-trifluoromethyl-oxazole-4-carboxylic acid {6-[(2-methoxy-ethyl)-methyl-amino]-pyridin-3-yl}-amide was prepared from 2-phenyl-5-trifluoromethyl-oxazole-4-carboxylic acid and $N^2$-(2-methoxy-ethyl)-$N^2$-methyl-pyridine-2,5-diamine. LCMS calcd for C20H19F3N4O3 (m/e) 420, obsd 421 (M+H).

Example 10

Preparation of 2-phenyl-5-trifluoromethyl-oxazole-4-carboxylic acid {2-[(2-methoxy-ethyl)-methyl-amino]-pyrimidin-5-yl}-amide

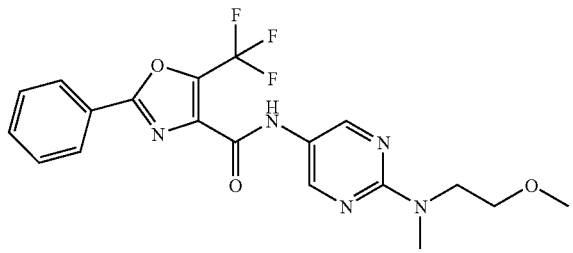

With a procedure similar to example 1 above, 2-phenyl-5-trifluoromethyl-oxazole-4-carboxylic acid {2-[(2-methoxy-ethyl)-methyl-amino]-pyrimidin-5-yl}-amide was prepared from 2-phenyl-5-trifluoromethyl-oxazole-4-carboxylic acid and N-(2-methoxy-ethyl)-N-methyl-pyrimidine-2,5-diamine. LCMS calcd for C19H18F3N5O3 (m/e) 421, obsd 422 (M+H).

Example 11

Preparation of (methyl-{5-[(2-phenyl-5-trifluoromethyl-oxazole-4-carbonyl)-amino]-pyridin-2-yl}-amino)-acetic acid methyl ester

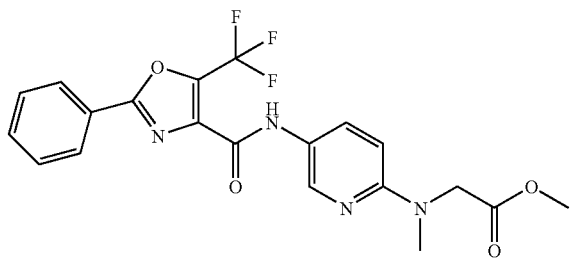

With a procedure similar to example 1 above, (methyl-{5-[(2-phenyl-5-trifluoromethyl-oxazole-4-carbonyl)-amino]-pyridin-2-yl}-amino)-acetic acid methyl ester was prepared from 2-phenyl-5-trifluoromethyl-oxazole-4-carboxylic acid and [(5-amino-pyridin-2-yl)-methyl-amino]-acetic acid methyl ester. LCMS calcd for C20H17F3N4O4 (m/e) 434, obsd 435 (M+H).

Example 12

Preparation of 2-phenyl-5-trifluoromethyl-oxazole-4-carboxylic acid [6-(methyl-methylcarbamoylmethyl-amino)-pyridin-3-yl]-amide

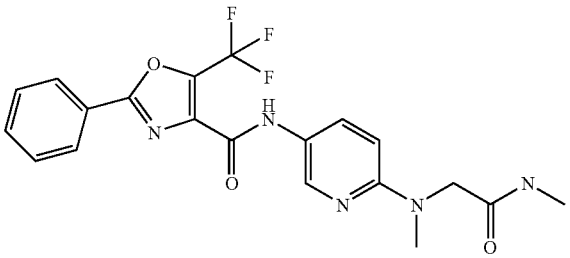

With a procedure similar to example 1 above, 2-phenyl-5-trifluoromethyl-oxazole-4-carboxylic acid [6-(methyl-methylcarbamoylmethyl-amino)-pyridin-3-yl]-amide was prepared from (methyl-{5-[(2-phenyl-5-trifluoromethyl-oxazole-4-carbonyl)-amino]-pyridin-2-yl}-amino)-acetic acid and methyl amine. LCMS calcd for C20H18F3N5O3 (m/e) 433, obsd 434 (M+H).

Example 13

Preparation of 2-phenyl-5-trifluoromethyl-oxazole-4-carboxylic acid [6-(dimethylcarbamoylmethyl-methyl-amino)-pyridin-3-yl]-amide

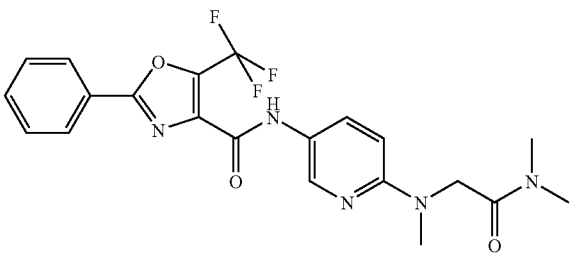

With a procedure similar to example 16, 2-phenyl-5-trifluoromethyl-oxazole-4-carboxylic acid [6-(dimethylcarbamoylmethyl-methyl-amino)-pyridin-3-yl]-amide was prepared from 2-phenyl-5-trifluoromethyl-oxazole-4-carboxylic acid and 2-[(5-amino-pyridin-2-yl)-methyl-amino]-N,N-dimethyl-acetamide LCMS calcd for C21H20F3N5O3 (m/e) 447.42, obsd 448.16 (M+H).

Example 14

Preparation of 2-phenyl-5-trifluoromethyl-oxazole-4-carboxylic acid (6-thiomorpholin-4-yl-pyridin-3-yl)-amide

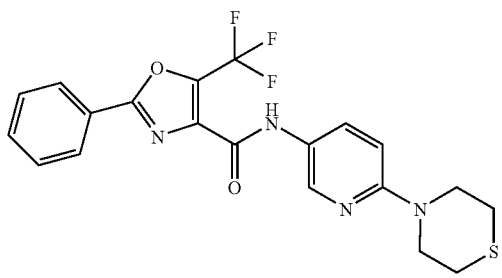

With a procedure similar to example 1 above, 2-phenyl-5-trifluoromethyl-oxazole-4-carboxylic acid (6-thiomorpholin-4-yl-pyridin-3-yl)-amide was prepared from 2-phenyl-5-trifluoromethyl-oxazole-4-carboxylic acid and 6-thiomorpholin-4-yl-pyridin-3-ylamine. LCMS calcd for C20H17F3N4O2S (m/e) 434, obsd 435 (M+H).

Example 15

Preparation of 4-methyl-2-phenyl-thiazole-5-carboxylic acid (6-morpholin-4-yl-pyridin-3-yl)-amide

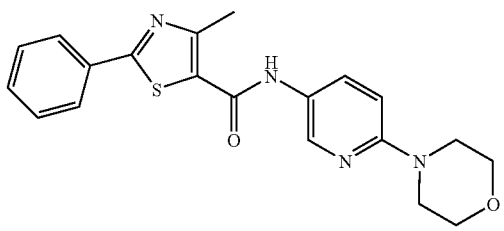

With a procedure similar to example 1 above, 4-methyl-2-phenyl-thiazole-5-carboxylic acid (6-morpholin-4-yl-pyridin-3-yl)-amide was prepared from 4-methyl-2-phenyl-thiazole-5-carboxylic acid and 6-morpholin-4-yl-pyridin-3-ylamine. LCMS calcd for C20H20N4O2S (m/e) 380, obsd 381 (M+H).

Example 16

Preparation of 2-phenyl-5-trifluoromethyl-oxazole-4-carboxylic acid {6-[3-(acetyl-methyl-amino)-pyrrolidin-1-yl]-pyridin-3-yl}-amide

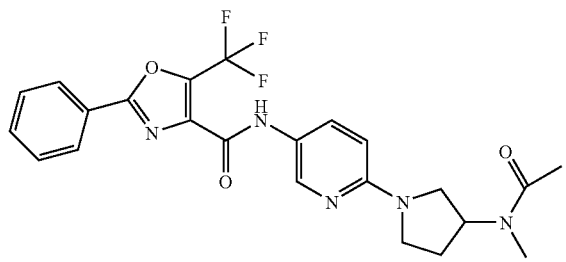

With a procedure similar to example 1 above, 2-phenyl-5-trifluoromethyl-oxazole-4-carboxylic acid {6-[3-(acetyl-methyl-amino)-pyrrolidin-1-yl]-pyridin-3-yl}-amide was prepared from 2-phenyl-5-trifluoromethyl-oxazole-4-carboxylic acid and N-[1-(5-amino-pyridin-2-yl)-pyrrolidin-3-yl]-N-methyl-acetamide. LCMS calcd for C23H22F3N5O3 (m/e) 473, obsd 474 (M+H).

Example 17

Preparation of 2-phenyl-5-trifluoromethyl-oxazole-4-carboxylic acid {6-[(R)-3-(acetyl-methyl-amino)-pyrrolidin-1-yl]-pyridin-3-yl}-amide

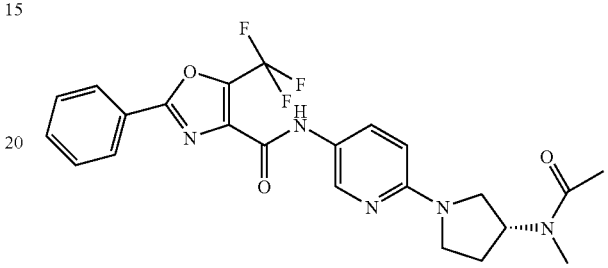

2-Phenyl-5-trifluoromethyl-oxazole-4-carboxylic acid {6-[(R)-3-(acetyl-methyl-amino)-pyrrolidin-1-yl]-pyridin-3-yl}-amide was prepared as a light yellow solid from the corresponding racemic compound by chiral supercritical fluid chromatography (Daicel AD column, 40% (1:1)EtOH/acetonitrile plus 20 mM ammonium acetate as a modifier). $[\alpha]_D = -15.2$ (MeOH).

Example 18

Preparation of 2-phenyl-5-trifluoromethyl-oxazole-4-carboxylic acid [6-(acetyl-methyl-amino)-pyridin-3-yl]-amide

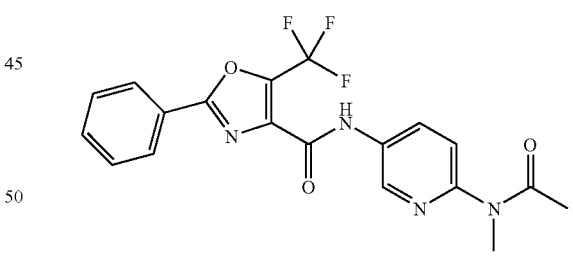

A mixture of 2-phenyl-5-trifluoromethyl-oxazole-4-carboxylic acid (260 mg, 1 mmol), N-(5-amino-pyridin-2-yl)-N-methyl-acetamide (165 mg, 1 mmol), bromo-tri-pyrrolidino-phosphonium hexafluorophosphate (470 mg, 1 mmol), and triethylamine (202 mg, 2 mmol) in anhydrous dichloromethane (5 mL) was stirred at room temperature overnight. After the reaction was complete, the solvent and excess triethylamine were removed by evaporation. Flash chromatography (Merck silica gel 60, 230-400 mesh, 0%-40% ethyl acetate in hexane for 20 min) gave 2-phenyl-5-trifluoromethyl-oxazole-4-carboxylic acid [6-(acetyl-methyl-amino)-pyridin-3-yl]-amide as a yellow solid. LCMS calcd for C19H15F3N4O3 (m/e) 404, obsd 405 (M+H).

Example 19

Preparation of 2-phenyl-5-trifluoromethyl-oxazole-4-carboxylic acid [6-(cyclopropanecarbonyl-methyl-amino)-pyridin-3-yl]-amide

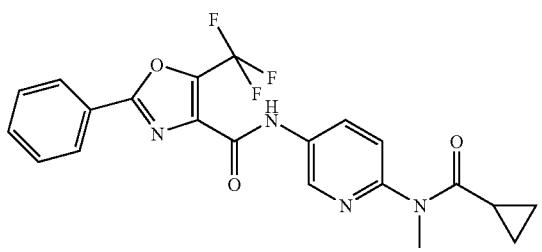

With a procedure similar to example 16, 2-phenyl-5-trifluoromethyl-oxazole-4-carboxylic acid [6-(cyclopropanecarbonyl-methyl-amino)-pyridin-3-yl]-amide was prepared as a white solid from 2-chloro-5-nitro-pyridine and cyclopropane carboxylic acid (4-amino-phenyl)-methyl-amide. LCMS calcd for C21H17F3N4O3 (m/e) 430, obsd 431 (M+H).

Example 20

Preparation of 5-isopropyl-2-phenyl-oxazole-4-carboxylic acid (6-morpholin-4-yl-pyridin-3-yl)-amide

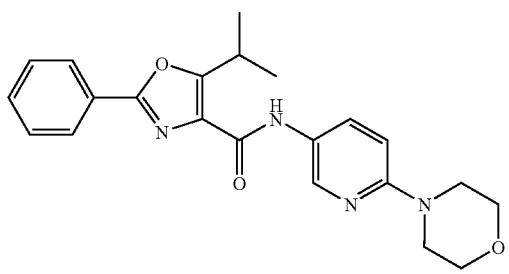

With a procedure similar to example 16 above, 5-isopropyl-2-phenyl-oxazole-4-carboxylic acid (6-morpholin-4-yl-pyridin-3-yl)-amide was prepared from 5-isopropyl-2-phenyl-oxazole-4-carboxylic acid and 6-morpholin-4-yl-pyridin-3-ylamine. LCMS calcd for C22H24N4O3 (m/e) 392, obsd 393 (M+H).

Example 21

Preparation of 5-chloro-2-phenyl-oxazole-4-carboxylic acid [6-(acetyl-methyl-amino)-pyridin-3-yl]-amide

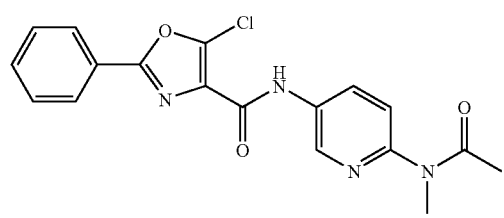

With a procedure similar to example 16 above, 5-chloro-2-phenyl-oxazole-4-carboxylic acid [6-(acetyl-methyl-amino)-pyridin-3-yl]-amide was prepared from 5-chloro-2-phenyl-oxazole-4-carboxylic acid and N-(5-amino-pyridin-2-yl)-N-methyl-acetamide. LCMS calcd for C18H15ClN4O3 (m/e) 370, obsd 371 (M+H).

Example 22

Preparation of 5-ethyl-2-phenyl-oxazole-4-carboxylic acid [6-(acetyl-methyl-amino)-pyridin-3-yl]-amide

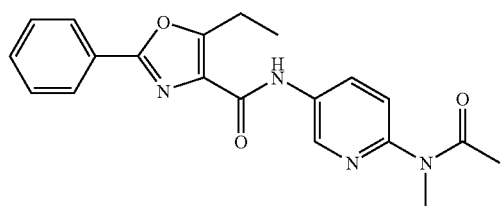

With a procedure similar to example 16 above, 5-ethyl-2-phenyl-oxazole-4-carboxylic acid [6-(acetyl-methyl-amino)-pyridin-3-yl]-amide was prepared from 5-ethyl-2-phenyl-oxazole-4-carboxylic acid and N-(5-amino-pyridin-2-yl)-N-methyl-acetamide. LCMS calcd for C20H20N4O3 (m/e) 364, obsd 365 (M+H).

Example 23

Preparation of 5-ethyl-2-phenyl-oxazole-4-carboxylic acid (6-morpholin-4-yl-pyridin-3-yl)-amide

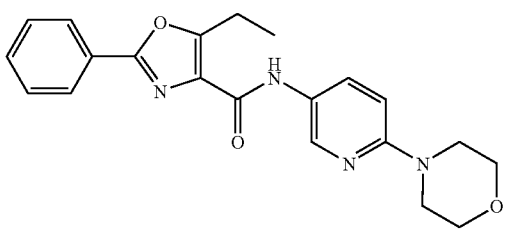

With a procedure similar to example 16 above, 5-ethyl-2-phenyl-oxazole-4-carboxylic acid (6-morpholin-4-yl-pyridin-3-yl)-amide was prepared from 5-ethyl-2-phenyl-oxazole-4-carboxylic acid and 6-morpholin-4-yl-pyridin-3-ylamine. LCMS calcd for C21H22N4O3 (m/e) 378, obsd 379 (M+H).

Example 24

Preparation of 2-phenyl-5-trifluoromethyl-oxazole-4-carboxylic acid [6-(methyl-propionyl-amino)-pyridin-3-yl]-amide

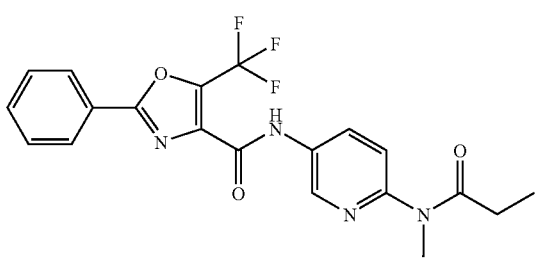

With a procedure similar to example 16 above, 2-phenyl-5-trifluoromethyl-oxazole-4-carboxylic acid [6-(methyl-propionyl-amino)-pyridin-3-yl]-amide was prepared from 2-phenyl-5-trifluoromethyl-oxazole-4-carboxylic acid and N-(5-amino-pyridin-2-yl)-N-methyl-propionamide. LCMS calcd for C20H17F3N4O3 (m/e) 418, obsd 419 (M+H).

Example 25

Preparation of 2-phenyl-5-trifluoromethyl-oxazole-4-carboxylic acid [6-(3-methoxy-pyrrolidin-1-yl)-pyridin-3-yl]-amide

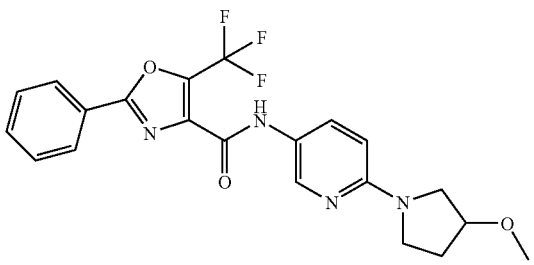

With a procedure similar to example 16 above, 2-phenyl-5-trifluoromethyl-oxazole-4-carboxylic acid [6-(3-methoxy-pyrrolidin-1-yl)-pyridin-3-yl]-amide was prepared from 2-phenyl-5-trifluoromethyl-oxazole-4-carboxylic acid and 6-(3-methoxy-pyrrolidin-1-yl)-pyridin-3-ylamine. LCMS calcd for C21H19F3N4O3 (m/e) 432, obsd 433 (M+H).

Example 26

Preparation of 2-phenyl-5-trifluoromethyl-oxazole-4-carboxylic acid [6-((S)-3-methoxy-pyrrolidin-1-yl)-pyridin-3-yl]-amide

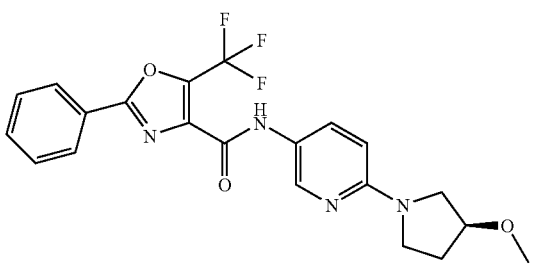

2-Phenyl-5-trifluoromethyl-oxazole-4-carboxylic acid [6-((S)-3-methoxy-pyrrolidin-1-yl)-pyridin-3-yl]-amide was prepared from the corresponding racemic compound by chiral supercritical fluid chromatography (Whelk-O1 R,R column, 35% MeOH as a modifier). $[\alpha]_D$=+14.5, (MeOH).

Example 27

Preparation of 2-phenyl-5-trifluoromethyl-oxazole-4-carboxylic acid (3-methoxy-3,4,5,6-tetrahydro-2H-[1,2']bipyridinyl-5'-yl)-amide

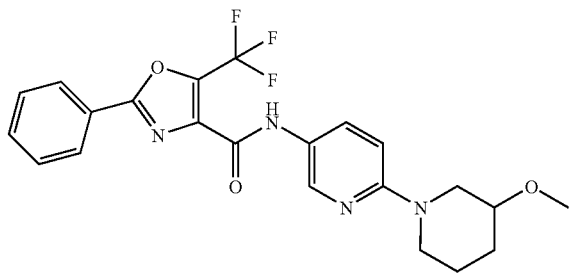

With a procedure similar to example 16 above, 2-phenyl-5-trifluoromethyl-oxazole-4-carboxylic acid (3-methoxy-3,4,5,6-tetrahydro-2H-[1,2']bipyridinyl-5'-yl)-amide was prepared from 2-phenyl-5-trifluoromethyl-oxazole-4-carboxylic acid and 3-methoxy-3,4,5,6-tetrahydro-2H-[1,2'] bipyridinyl-5'-ylamine. LCMS calcd for C22H21F3N4O3 (m/e) 446, obsd 447 (M+H).

Example 28

Preparation of 2-phenyl-5-trifluoromethyl-oxazole-4-carboxylic acid [6-(methyl-propyl-amino)-pyridin-3-yl]-amide

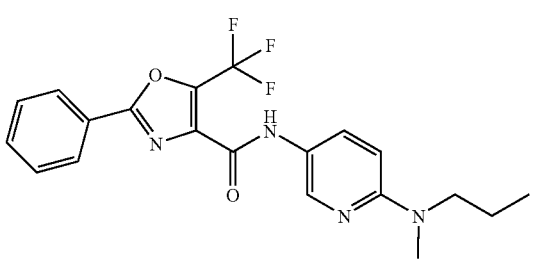

With a procedure similar to example 16 above, 2-phenyl-5-trifluoromethyl-oxazole-4-carboxylic acid [6-(methyl-propyl-amino)-pyridin-3-yl]-amide was prepared from 2-phenyl-5-trifluoromethyl-oxazole-4-carboxylic acid and $N^2$-methyl-$N^2$-propyl-pyridine-2,5-diamine. LCMS calcd for C20H19F3N4O2 (m/e) 404, obsd 405 (M+H).

Example 29

Preparation of 2-phenyl-5-trifluoromethyl-oxazole-4-carboxylic acid [6-(butyl-methyl-amino)-pyridin-3-yl]-amide

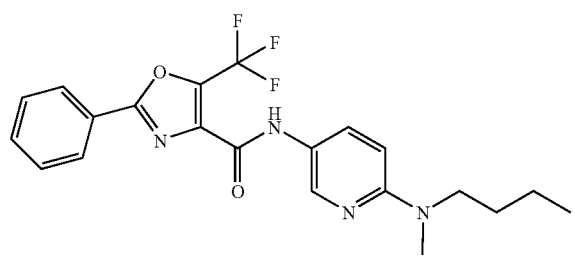

With a procedure similar to example 16 above, 2-phenyl-5-trifluoromethyl-oxazole-4-carboxylic acid [6-(butyl-methyl-amino)-pyridin-3-yl]-amide From 2-phenyl-5-trifluoromethyl-oxazole-4-carboxylic acid and $N^2$-butyl-$N^2$-methyl-pyridine-2,5-diamine. LCMS calcd for C21H21F3N4O2 (m/e) 418, obsd 419 (M+H).

Example 30

Preparation of 2-phenyl-5-trifluoromethyl-oxazole-4-carboxylic acid {6-[(3-methoxy-propyl)-methyl-amino]-pyridin-3-yl}-amide

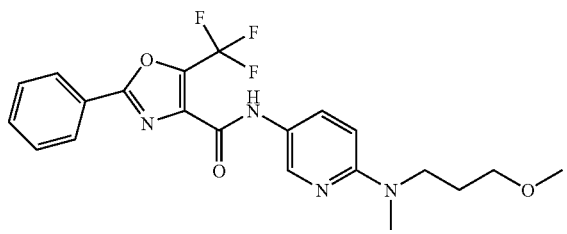

With a procedure similar to example 16 above, 2-phenyl-5-trifluoromethyl-oxazole-4-carboxylic acid {6-[(3-methoxy-propyl)-methyl-amino]-pyridin-3-yl}-amide was prepared from 2-phenyl-5-trifluoromethyl-oxazole-4-carboxylic acid and $N^2$-(3-methoxy-propyl)-$N^2$-methyl-pyridine-2,5-diamine. LCMS calcd for $C_{21}H_{21}F_3N_4O_3$ (m/e) 434, obsd 435 (M+H).

Example 31

Preparation of 2-phenyl-5-trifluoromethyl-oxazole-4-carboxylic acid [6-(3-methoxy-propylamino)-pyridin-3-yl]-amide

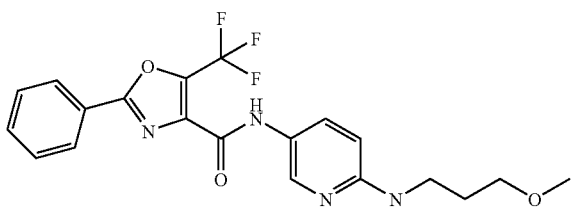

With a procedure similar to example 16 above, 2-phenyl-5-trifluoromethyl-oxazole-4-carboxylic acid [6-(3-methoxy-propylamino)-pyridin-3-yl]-amide was prepared from 2-phenyl-5-trifluoromethyl-oxazole-4-carboxylic acid and $N^2$-(3-methoxy-propyl)-pyridine-2,5-diamine. LCMS calcd for $C_{20}H_{19}F_3N_4O_3$ (m/e) 420, obsd 421 (M+H).

Example 32

Preparation of 2-phenyl-5-trifluoromethyl-oxazole-4-carboxylic acid (2-morpholin-4-yl-thiazol-5-yl)-amide

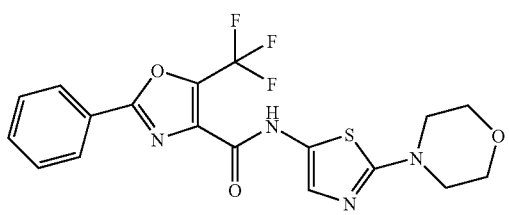

With a procedure similar to example 16 above, 2-phenyl-5-trifluoromethyl-oxazole-4-carboxylic acid (2-morpholin-4-yl-thiazol-5-yl)-amide was prepared from 2-phenyl-5-trifluoromethyl-oxazole-4-carboxylic acid and 2-morpholin-4-yl-thiazol-5-ylamine. LCMS calcd for $C_{18}H_{15}F_3N_4O_3S$ (m/e) 424, obsd 425 (M+H).

Example 33

Preparation of 2-phenyl-5-trifluoromethyl-oxazole-4-carboxylic acid {2-[(2-methoxy-ethyl)-methyl-amino]-thiazol-5-yl}-amide

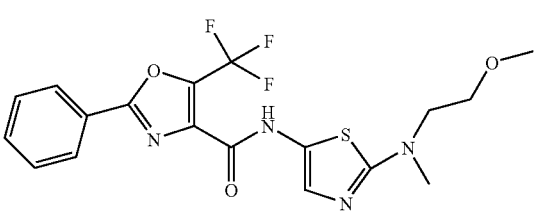

With a procedure similar to example 16 above, 2-phenyl-5-trifluoromethyl-oxazole-4-carboxylic acid {2-[(2-methoxy-ethyl)-methyl-amino]-thiazol-5-yl}-amide was prepared from 2-phenyl-5-trifluoromethyl-oxazole-4-carboxylic acid and $N^2$-(2-methoxy-ethyl)-$N^2$-methyl-thiazole-2,5-diamine. LCMS calcd for $C_{18}H_{17}F_3N_4O_3S$ (m/e) 426, obsd 427 (M+H).

Example 34

Preparation of 2-phenyl-5-trifluoromethyl-oxazole-4-carboxylic acid [6-((R)-2-methoxymethyl-pyrrolidin-1-yl)-pyridin-3-yl]-amide

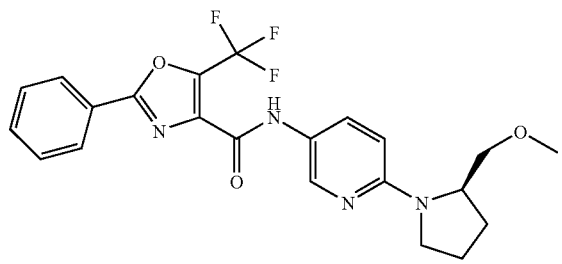

With a procedure similar to example 16 above, 2-phenyl-5-trifluoromethyl-oxazole-4-carboxylic acid [6-((R)-2-methoxymethyl-pyrrolidin-1-yl)-pyridin-3-yl]-amide was prepared from 2-phenyl-5-trifluoromethyl-oxazole-4-carboxylic acid and 6-((R)-2-methoxymethyl-pyrrolidin-1-yl)-pyridin-3-ylamine. LCMS calcd for $C_{22}H_{21}F_3N_4O_3$ (m/e) 446, obsd 447 (M+H).

Example 35

Preparation of 2-phenyl-5-trifluoromethyl-oxazole-4-carboxylic acid {6-[ethyl-(2-methoxy-ethyl)-amino]-pyridin-3-yl}-amide

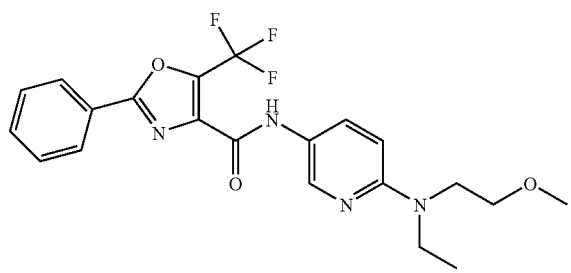

With a procedure similar to example 16 above, 2-phenyl-5-trifluoromethyl-oxazole-4-carboxylic acid {6-[ethyl-(2-methoxy-ethyl)-amino]-pyridin-3-yl}-amide was prepared from 2-phenyl-5-trifluoromethyl-oxazole-4-carboxylic acid and $N^2$-ethyl-$N^2$-(2-methoxy-ethyl)-pyridine-2,5-diamine. LCMS calcd for C21H21F3N4O3 (m/e) 434, obsd 435 (M+H).

Example 36

Preparation of 2-phenyl-5-trifluoromethyl-oxazole-4-carboxylic acid [6-(2-methoxy-ethylamino)-pyridin-3-yl]-amide

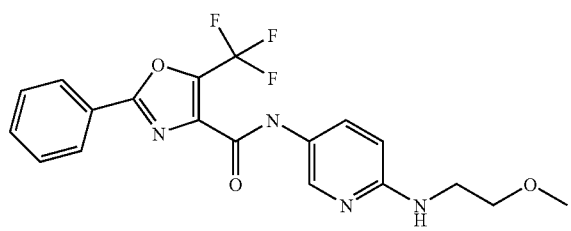

With a procedure similar to example 16 above, 2-phenyl-5-trifluoromethyl-oxazole-4-carboxylic acid [6-(2-methoxy-ethylamino)-pyridin-3-yl]-amide was prepared from 2-phenyl-5-trifluoromethyl-oxazole-4-carboxylic acid and $N^2$-(2-methoxy-ethyl)-pyridine-2,5-diamine. LCMS calcd for C19H17F3N4O3 (m/e) 406, obsd 407 (M+H).

Example 37

Preparation of 2-phenyl-5-trifluoromethyl-oxazole-4-carboxylic acid [6-(2-methoxy-ethoxy)-pyridin-3-yl]-amide

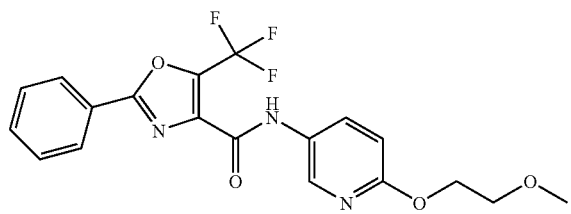

With a procedure similar to example 16 above, 2-phenyl-5-trifluoromethyl-oxazole-4-carboxylic acid [6-(2-methoxy-ethoxy)-pyridin-3-yl]-amide was prepared from 2-phenyl-5-trifluoromethyl-oxazole-4-carboxylic acid and 6-(2-methoxy-ethoxy)-pyridin-3-ylamine. LCMS calcd for C19H16F3N3O4 (m/e) 407, obsd 408 (M+H).

Example 38

Preparation of 2-phenyl-5-trifluoromethyl-oxazole-4-carboxylic acid [6-(ethyl-methyl-amino)-pyridin-3-yl]-amide

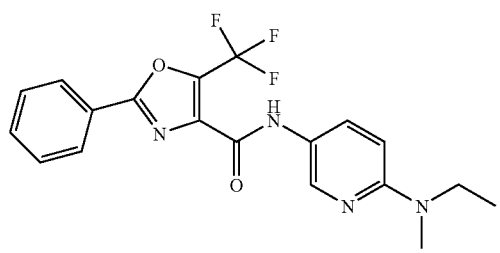

With a procedure similar to example 16 above, 2-phenyl-5-trifluoromethyl-oxazole-4-carboxylic acid [6-(ethyl-methyl-amino)-pyridin-3-yl]-amide was prepared from 2-phenyl-5-trifluoromethyl-oxazole-4-carboxylic acid and $N^2$-ethyl-$N^2$-methyl-pyridine-2,5-diamine. LCMS calcd for C19H17F3N4O2 (m/e) 390, obsd 391 (M+H).

Example 39

Preparation of 2-phenyl-5-trifluoromethyl-oxazole-4-carboxylic acid (6-ethylamino-pyridin-3-yl)-amide

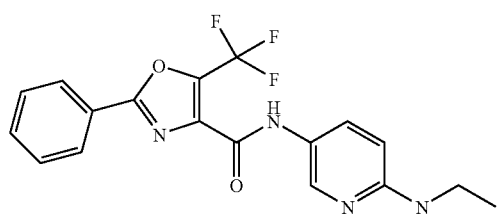

With a procedure similar to example 16 above, 2-phenyl-5-trifluoromethyl-oxazole-4-carboxylic acid (6-ethylamino-pyridin-3-yl)-amide was prepared from 2-phenyl-5-trifluoromethyl-oxazole-4-carboxylic acid and $N^2$-ethyl-pyridine-2,5-diamine. LCMS calcd for C18H15F3N4O2 (m/e) 376, obsd 377 (M+H).

Example 40

Preparation of 2-phenyl-5-trifluoromethyl-oxazole-4-carboxylic acid (6-diethylamino-pyridin-3-yl)-amide

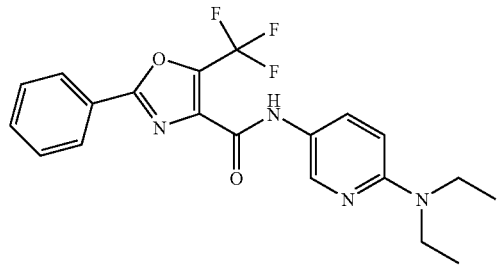

With a procedure similar to example 16 above, 2-phenyl-5-trifluoromethyl-oxazole-4-carboxylic acid (6-diethylamino-pyridin-3-yl)-amide was prepared from 2-phenyl-5-trifluoromethyl-oxazole-4-carboxylic acid and N²,N²-diethyl-pyridine-2,5-diamine. LCMS calcd for C20H19F3N4O2 (m/e) 404, obsd 405 (M+H).

Example 41

Preparation of 2-phenyl-5-trifluoromethyl-oxazole-4-carboxylic acid (6-dimethylamino-pyridin-3-yl)-amide

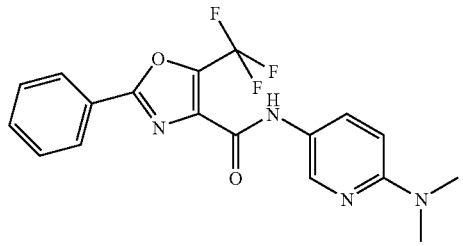

With a procedure similar to the example 1 above, 2-phenyl-5-trifluoromethyl-oxazole-4-carboxylic acid (6-dimethylamino-pyridin-3-yl)-amide was prepared from 2-phenyl-trifluoromethyl-oxazole-4-carboxylic acid and N²,N²-dimethyl-pyridine-2,5-diamine. LCMS calcd for C18H15F3N4O2 (m/e) 376.34 obsd 377.12 (M+H).

Example 42

Preparation of 2-phenyl-5-trifluoromethyl-oxazole-4-carboxylic acid [6-(isopropyl-methyl-amino)-pyridin-3-yl]-amide

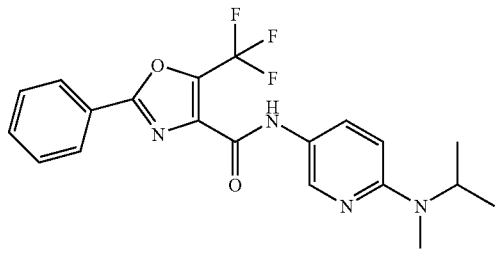

With a procedure similar to example 1 above, 2-phenyl-5-trifluoromethyl-oxazole-4-carboxylic acid [6-(isopropyl-methyl-amino)-pyridin-3-yl]-amide was prepared from 2-phenyl-5-trifluoromethyl-oxazole-4-carboxylic acid and N²-isopropyl-N²-methyl-pyridine-2,5-diamine. LCMS calcd for C20H19F3N4O2 (m/e) 404, obsd 405 (M+H).

Example 43

Preparation of 2-phenyl-5-trifluoromethyl-oxazole-4-carboxylic acid (6-cyclopentylamino-pyridin-3-yl)-amide

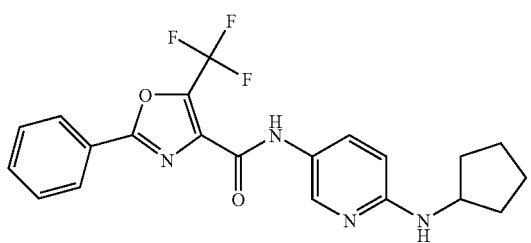

A mixture of 2-phenyl-5-(trifluoromethyl)-oxazole-4-carboxylic acid (454 mg, 1.77 mmol), CH₂Cl₂ (5 mL), and a catalytic amount of DMF was stirred under Ar, cooled in an ice bath, and oxalyl chloride (308 µL, 3.53 mmol) was added dropwise into the mixture over 5 min. The mixture was immediately allowed to warm to room temperature and after 1.5 hr the reaction was concentrated to dryness. Dichloromethane was added and the solution was evaporated to dryness again. The white-yellow solid was re-dissolved in 5 mL of CH₂Cl₂ and added dropwise, under Ar, into a 0° C. solution of cyclopentyl-pyridine-2,5-diamine (448 mg, 2.53 mmol), a catalytic amount of DMAP and triethylamine (602 µL, 4.33 mmol) in 5 mL of CH₂Cl₂. The reaction was allowed to warm to room temperature overnight then concentrated and the residue was supported onto silica gel, and purified by flash chromatography using the Analogix system with a 40 g Redisep silica gel column with increasing concentrations of EtOAc in hexane (40 mL/min, equilibrate with 0%, 0-5 min: 0%, 5-25 min: 0 to 30%, 25-40 min: 30%). The product was triturated with hexanes six times and a 10% ether hexane four times, 20 mL total, to afford the product, 2-phenyl-5-trifluoromethyl-oxazole-4-carboxylic acid (6-cyclopentylamino-pyridin-3-yl)-amide, as an off white solid (315 mg, 50% yield). LCMS for C₂₁H₁₉F₃N₄O₂ calcd. (m/e) 416, observed 417 (M+H).

Example 44

Preparation of 2-phenyl-5-trifluoromethyl-oxazole-4-carboxylic acid (6-cyclohexylamino-pyridin-3-yl)-amide

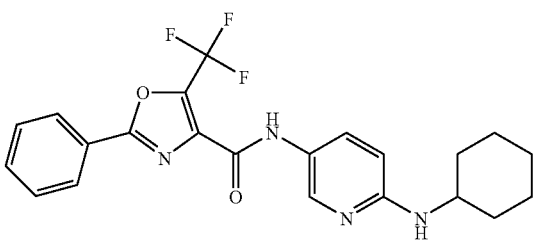

With a method similar to that used for the preparation of 2-phenyl-5-trifluoromethyl-oxazole-4-carboxylic acid (6-cyclopentylamino-pyridin-3-yl)-amide above, 2-phenyl-5-trifluoromethyl-oxazole-4-carboxylic acid (6-cyclohexylamino-pyridin-3-yl)-amide was prepared from 2-phenyl-5-(trifluoromethyl)-oxazole-4-carboxylic acid and N²-cyclohexyl-pyridine-2,5-diamine. After flash column chromatography, as described above, and recrystallization from ether the product was isolated as a white pink solid. LCMS for C₂₂H₂₁F₃N₄O₂ calculated (m/e) 430, observed 431 (M+H).

Example 45

Preparation of 2-phenyl-5-trifluoromethyl-oxazole-4-carboxylic acid (6-cyclopropylamino-pyridin-3-yl)-amide

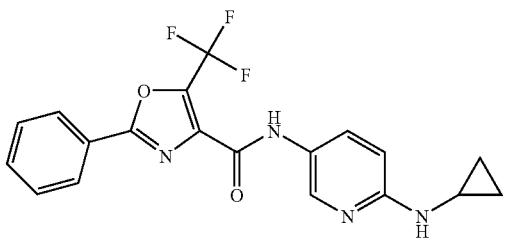

With a method similar to that used for the preparation of 2-phenyl-5-trifluoromethyl-oxazole-4-carboxylic acid (6-cyclopentylamino-pyridin-3-yl)-amide above, 2-phenyl-5-trifluoromethyl-oxazole-4-carboxylic acid (6-cyclopropylamino-pyridin-3-yl)-amide was prepared from 2-phenyl-5-trifluoromethyl-oxazole-4-carboxylic acid and $N^2$-cyclopropyl-pyridine-2,5-diamine as a light purple solid. LCMS for $C_{19}H_{15}F_3N_4O_2$ calculated (m/e) 388, observed 389 (M+H).

Example 46

Preparation of 2-phenyl-5-trifluoromethyl-oxazole-4-carboxylic acid [6-(cyclopropyl-methyl-amino]-pyridin-3-yl]-amide

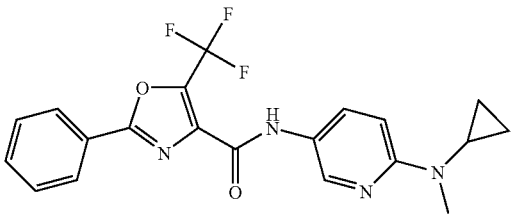

With a method similar to that used for the preparation of 2-phenyl-5-trifluoromethyl-oxazole-4-carboxylic acid (6-cyclopentylamino-pyridin-3-yl)-amide above, 2-phenyl-5-trifluoromethyl-oxazole-4-carboxylic acid [6-(cyclopropyl-methyl-amino)-pyridin-3-yl]-amide was prepared from 2-phenyl-5-trifluoromethyl-oxazole-4-carboxylic acid and $N^2$-cyclopropyl-$N^2$-methyl-pyridine-2,5-diamine as a yellow solid. LCMS for $C_{20}H_{17}F_3N_4O_2$ calculated (m/e) 402, observed 403 (M+H).

Example 47

Preparation of 2-phenyl-5-trifluoromethyl-oxazole-4-carboxylic acid [6-(cyclobutyl-methyl-amino]-pyridin-3-yl]-amide

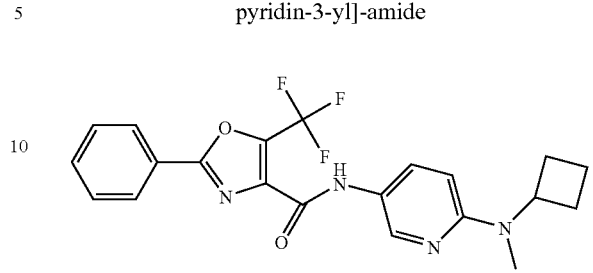

With a method similar to that used for the preparation of 2-phenyl-5-trifluoromethyl-oxazole-4-carboxylic acid (6-cyclopentylamino-pyridin-3-yl)-amide above, 2-phenyl-5-trifluoromethyl-oxazole-4-carboxylic acid [6-(cyclobutyl-methyl-amino)-pyridin-3-yl]-amide was prepared from 2-phenyl-5-trifluoromethyl-oxazole-4-carboxylic acid and $N^2$-cyclobutyl-$N^2$-methyl-pyridine-2,5-diamine as a yellow solid. (LCMS for $C_{21}H_{19}F_3N_4O_2$ calcd. (m/e) 416, observed 417 (M+H).

Example 48

Preparation of 2-phenyl-5-trifluoromethyl-oxazole-4-carboxylic acid [6-(cyclopropyl-methyl-amino]-pyrimidin-3-yl]-amide

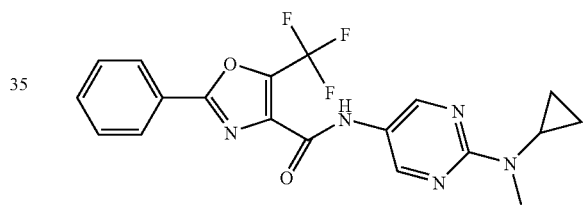

With a method similar to that used for the preparation of 2-phenyl-5-trifluoromethyl-oxazole-4-carboxylic acid (6-cyclopentylamino-pyridin-3-yl)-amide above, 2-phenyl-5-trifluoromethyl-oxazole-4-carboxylic acid [6-(cyclopropyl-methyl-amino)-pyrimidin-3-yl]-amide was prepared from 2-phenyl-5-trifluoromethyl-oxazole-4-carboxylic acid and $N^2$-cyclopropyl-$N^2$-methyl-pyrimidine-2,5-diamine as a white light yellow solid (LCMS for $C_{19}H_{16}F_3N_5O_2$ calculated (m/e) 403, observed 404 (M+H).

Example 49

Preparation of 2-phenyl-5-trifluoromethyl-oxazole-4-carboxylic acid {6-[(2-methoxy-acetyl)-methyl-amino]-pyridin-3-yl}-amide

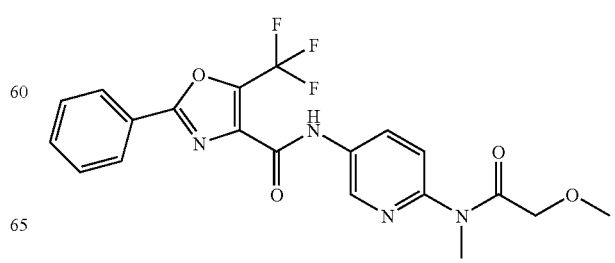

With a procedure similar to example 16 above, 2-phenyl-5-trifluoromethyl-oxazole-4-carboxylic acid {6-[(2-methoxy-acetyl)-methyl-amino]-pyridin-3-yl}-amide was prepared from 2-phenyl-5-trifluoromethyl-oxazole-4-carboxylic acid and N-(5-amino-pyridin-2-yl)-2-methoxy-N-methyl-acetamide. LCMS calcd for C20H17F3N4O4 (m/e) 434, obsd 435 (M+H).

Example 50

Preparation of 2-phenyl-5-trifluoromethyl-oxazole-4-carboxylic acid {6-[((S)-2-methoxy-1-methyl-ethyl)-methyl-amino]-pyridin-3-yl}-amide

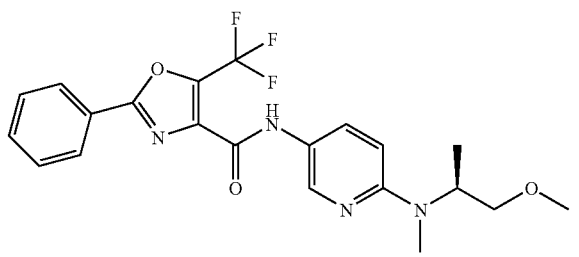

With a procedure similar to example 16 above, 2-phenyl-5-trifluoromethyl-oxazole-4-carboxylic acid {6-[((S)-2-methoxy-1-methyl-ethyl)-methyl-amino]-pyridin-3-yl}-amide was prepared from 2-phenyl-5-trifluoromethyl-oxazole-4-carboxylic acid and $N^2$—((S)-2-methoxy-1-methyl-ethyl)-$N^2$-methyl-pyridine-2,5-diamine. LCMS calcd for C21H21F3N4O3 (m/e) 434, obsd 435 (M+H).

Example 51

Preparation of 2-phenyl-5-trifluoromethyl-oxazole-4-carboxylic acid-[6-(2-methoxy-1-methyl-ethylamino)pyridin-3-yl]amide hydrogen chloride

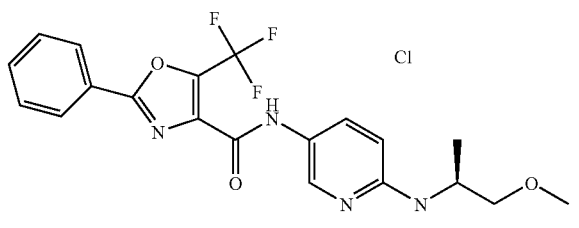

With a method similar to example 16 above, 2-phenyl-5-trifluoromethyl-oxazole-4-carboxylic acid-[6-(2-methoxy-1-methyl-ethylamino)pyridin-3-yl]amide hydrogen chloride was prepared from 2-phenyl-5-trifluoromethyl-oxazole-4-carboxylic acid and N-(2-methoxy-1-methyl-ethyl)-2,5-diaminopyridine. The purified oily material from column chromatography was dissolved in ether and treated with gaseous hydrogen chloride in ether (3N) to give a white precipitate as a hydrochloride salt. LCMS calcd for the neutral form C20H19F3N4O3 m/e 420.39, obsd 421.02 (ES, M+H).

Example 52

Preparation of (R)-2-phenyl-5-trifluoromethyl-oxazole-4-carboxylic acid-[6-(1-phenyl-ethylamino)pyridin-3-yl]amide

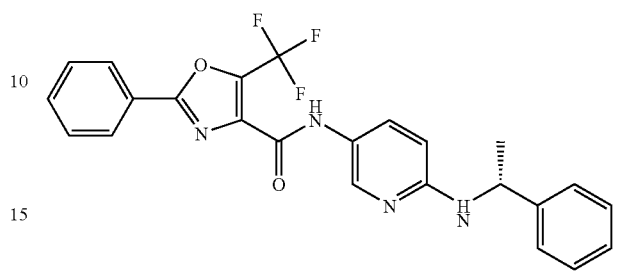

With a method similar to example 16 above, (R)-2-phenyl-5-trifluoromethyl-oxazole-4-carboxylic acid-[6-(1-phenyl-ethylamino)pyridin-3-yl]amide was prepared from 2-phenyl-5-trifluoromethyl-oxazole-4-carboxylic acid and (R)-2-N-(1-phenylethyl)-2,5-diaminopyridine. LCMS calcd for C24H19F3N4O2 m/e 452.4, obsd 453.2 (ES, M+H).

Example 53

Preparation of 2-phenyl-5-trifluoromethyloxazole-4-carboxylic acid-[6-(3,3-difluoroazetidin-1-yl)pyridin-3-yl]amide

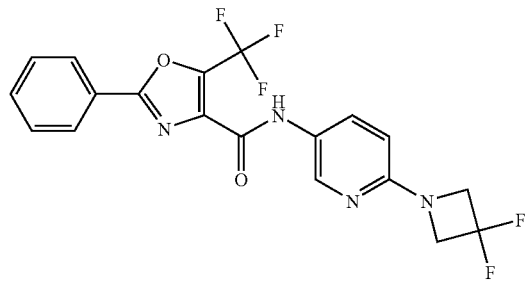

With a method similar to example 16 above, 2-phenyl-5-trifluoromethyloxazole-4-carboxylic acid-[6-(3,3-difluoroazetidin-1-yl)pyridin-3-yl]amide was prepared from 2-phenyl-5-trifluoromethyl-oxazole-4-carboxylic acid and 3-amino-6-(3,3-difluoroazetidin-1-yl)pyridine. LCMS calcd for C19H13F5N4O2 m/e 424.33, obsd 425.0 (ES, M+H).

Example 54

Preparation of 2-phenyl-5-trifluoromethyl-oxazole-4-carboxylic acid {6-[methyl-(2,2,2-trifluoro-ethyl)-amino]-pyridin-3-yl}-amide

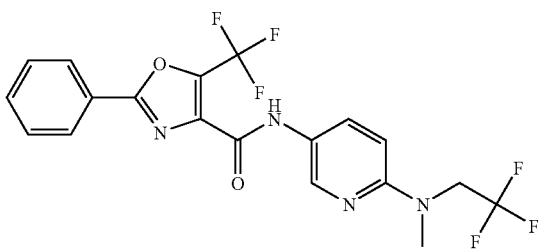

With a procedure similar to example 16 above, 2-phenyl-5-trifluoromethyl-oxazole-4-carboxylic acid {6-[methyl-(2,2,2-trifluoro-ethyl)-amino]-pyridin-3-yl}-amide was prepared from 2-phenyl-5-trifluoromethyl-oxazole-4-carboxylic acid and $N^2$-methyl-$N^2$-(2,2,2-trifluoro-ethyl)-pyridine-2,5-diamine. LCMS calcd for C19H14F6N4O2 (m/e) 444, obsd 445 (M+H). The NMR spectrum obtained on the sample is compatible with its structure.

Example 55

Preparation of 5-methyl-2-phenyl-2H-[1,2,3]triazole-4-carboxylic acid {6-[methyl-(2,2,2-trifluoro-ethyl)-amino]-pyridin-3-yl}-amide

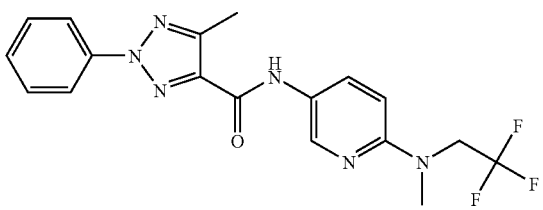

With a procedure similar to example 16 above, 5-methyl-2-phenyl-2H-[1,2,3]triazole-4-carboxylic acid {6-[methyl-(2,2,2-trifluoro-ethyl)-amino]-pyridin-3-yl}-amide was prepared from 5-methyl-2-phenyl-2H-[1,2,3]triazole-4-carboxylic acid and $N^2$-methyl-$N^2$-(2,2,2-trifluoro-ethyl)-pyridine-2,5-diamine. LCMS calcd for C18H17F3N6O (m/e) 390, obsd 391 (M+H). The NMR spectrum obtained on the sample is compatible with its structure.

Example 56

Preparation of 2-phenyl-5-trifluoromethyl-oxazole-4-carboxylic acid {2-[methyl-(2,2,2-trifluoro-ethyl)-amino]-pyrimidin-5-yl}-amide

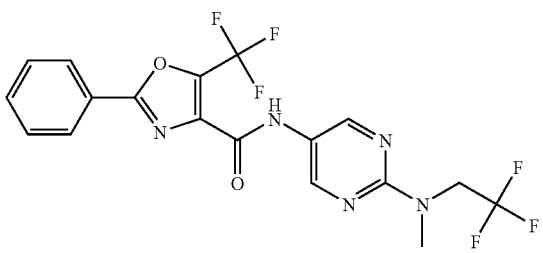

With a procedure similar to example 16 above, 2-Phenyl-5-trifluoromethyl-oxazole-4-carboxylic acid {2-[methyl-(2,2,2-trifluoro-ethyl)-amino]-pyrimidin-5-yl}-amide was prepared from 2-Phenyl-5-trifluoromethyl-oxazole-4-carboxylic acid and N-Methyl-N-(2,2,2-trifluoro-ethyl)-pyrimidine-2,5-diamine. LCMS calcd for C18H13F6N5O2 (m/e) 445, obsd 446 (M+H). The NMR spectrum obtained on the sample is compatible with its structure.

Example 57

Preparation of 5-methyl-2-phenyl-2H-[1,2,3]triazole-4-carboxylic acid [6-(cyclopropyl-methyl-amino)-pyridin-3-yl]-amide

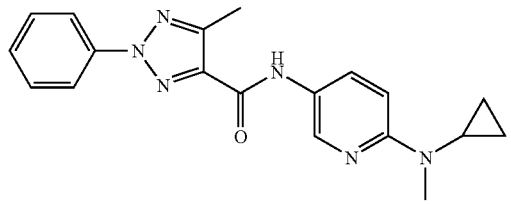

With a procedure similar to example 16 above, 5-methyl-2-phenyl-2H-[1,2,3]triazole-4-carboxylic acid [6-(cyclopropyl-methyl-amino)-pyridin-3-yl]-amide was prepared from 5-methyl-2-phenyl-2H-[1,2,3]triazole-4-carboxylic acid and $N^2$-cyclopropyl-$N^2$-methyl-pyridine-2,5-diamine. LCMS calcd for C19H20N6O (m/e) 348, obsd 349 (M+H).

Example 58

Preparation of 2-methyl-5-phenyl-2H-pyrazole-3-carboxylic acid {6-[(2-methoxy-ethyl)-methyl-amino]-pyridin-3-yl}-amide

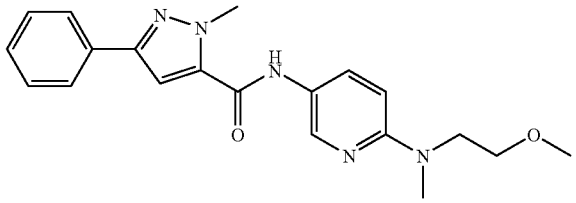

With a procedure similar to example 16 above, 2-methyl-5-phenyl-2H-pyrazole-3-carboxylic acid {6-[(2-methoxy-ethyl)-methyl-amino]-pyridin-3-yl}-amide was prepared from 2-methyl-5-phenyl-2H-pyrazole-3-carboxylic acid (made by hydrolysis of the corresponding commercially available ethyl ester) and $N^2$-(2-methoxy-ethyl)-$N^2$-methyl-pyridine-2,5-diamine. LCMS calcd for C20H23N5O2 (m/e) 365, obsd 366 (M+H). The NMR spectrum obtained on the sample is compatible with its structure.

Example 59

Preparation of 5-(4-methoxy-phenyl)-2-methyl-2H-pyrazole-3-carboxylic acid {6-[(2-methoxy-ethyl)-methyl-amino]-pyridin-3-yl}-amide

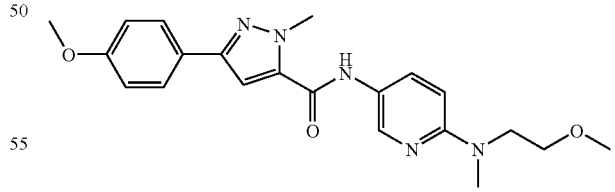

With a procedure similar to example 16 above, 5-(4-methoxy-phenyl)-2-methyl-2H-pyrazole-3-carboxylic acid {6-[(2-methoxy-ethyl)-methyl-amino]-pyridin-3-yl}-amide was prepared from 5-(4-methoxy-phenyl)-2-methyl-2H-pyrazole-3-carboxylic acid (made by hydrolysis of the corresponding commercially available ethyl ester) and $N^2$-(2-methoxy-ethyl)-$N^2$-methyl-pyridine-2,5-diamine. LCMS calcd for C21H25N5O3 (m/e) 395, obsd 396 (M+H). The NMR spectrum obtained on the sample is compatible with its structure.

Example 60

Preparation of 5-phenyl-2-(2,2,2-trifluoro-ethyl)-2H-pyrazole-3-carboxylic acid {6-[(2-methoxy-ethyl)-methyl-amino]-pyridin-3-yl}-amide

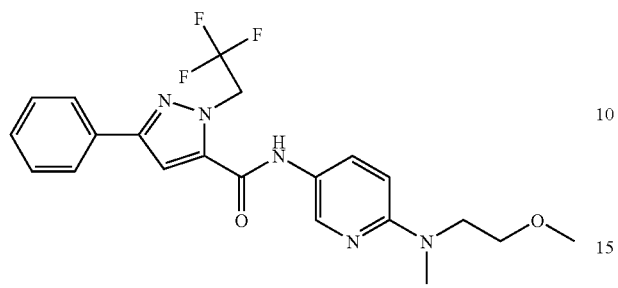

With a procedure similar to example 16 above, 5-phenyl-2-(2,2,2-trifluoro-ethyl)-2H-pyrazole-3-carboxylic acid {6-[(2-methoxy-ethyl)-methyl-amino]-pyridin-3-yl}-amide was prepared from 5-phenyl-2-(2,2,2-trifluoro-ethyl)-2H-pyrazole-3-carboxylic acid and $N^2$-(2-methoxy-ethyl)-$N^2$-methyl-pyridine-2,5-diamine. LCMS calcd for C21H22F3N5O2 (m/e) 433, obsd 434 (M+H). The NMR spectrum obtained on the sample is compatible with its structure.

Example 61

Preparation of 1-phenyl-3-trifluoromethyl-1H-pyrazole-4-carboxylic acid {6-[(2-methoxy-ethyl)-methyl-amino]-pyridin-3-yl}-amide

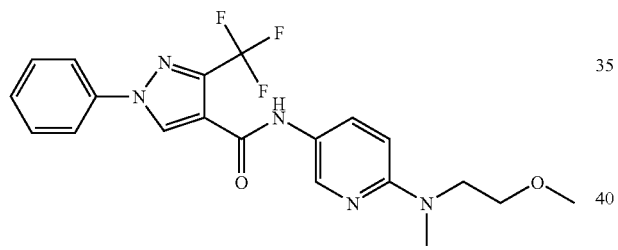

With a procedure similar to example 16 above, 1-phenyl-3-trifluoromethyl-1H-pyrazole-4-carboxylic acid {6-[(2-methoxy-ethyl)-methyl-amino]-pyridin-3-yl}-amide was prepared from 1-phenyl-3-trifluoromethyl-1H-pyrazole-4-carboxylic acid and $N^2$-(2-methoxy-ethyl)-$N^2$-methyl-pyridine-2,5-diamine. LCMS calcd for C20H20F3N5O2 (m/e) 419, obsd 420 (M+H). The NMR spectrum obtained on the sample is compatible with its structure.

Example 62

Preparation of 5-methyl-2-phenyl-2H-[1,2,3]triazole-4-carboxylic acid {6-[(2-methoxy-ethyl)-methyl-amino]-pyridin-3-yl}-amide

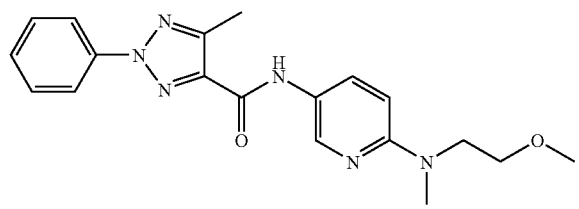

With a procedure similar to example 16 above, 5-methyl-2-phenyl-2H-[1,2,3]triazole-4-carboxylic acid {6-[(2-methoxy-ethyl)-methyl-amino]-pyridin-3-yl}-amide was prepared from 5-methyl-2-phenyl-2H-[1,2,3]triazole-4-carboxylic acid and $N^2$-(2-methoxy-ethyl)-$N^2$-methyl-pyridine-2,5-diamine. LCMS calcd for C19H22N6O2 (m/e) 366, obsd 367 (M+H). The NMR spectrum obtained on the sample is compatible with its structure.

Example 63

Preparation of 2-(2-chloro-phenyl)-5-trifluoromethyl-oxazole-4-carboxylic acid {6-[(2-methoxy-ethyl)-methyl-amino]-pyridin-3-yl}-amide

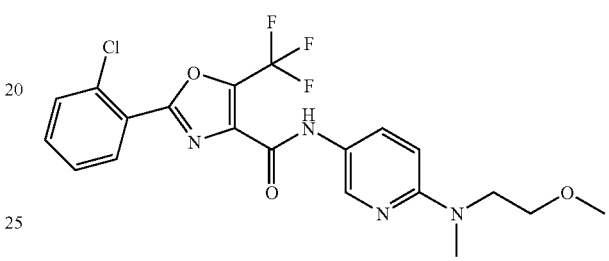

With a procedure similar to example 16 above, 2-(2-chloro-phenyl)-5-trifluoromethyl-oxazole-4-carboxylic acid {6-[(2-methoxy-ethyl)-methyl-amino]-pyridin-3-yl}-amide was prepared from 2-(2-chloro-phenyl)-5-trifluoromethyl-oxazole-4-carboxylic acid and $N^2$-(2-methoxy-ethyl)-$N^2$-methyl-pyridine-2,5-diamine. LCMS calcd for C20H18ClF3N4O3 (m/e) 454, obsd 455 (M+H).

Example 64

Preparation of 2-(2-chloro-phenyl)-5-trifluoromethyl-oxazole-4-carboxylic acid (6-morpholin-4-yl-pyridin-3-yl)-amide

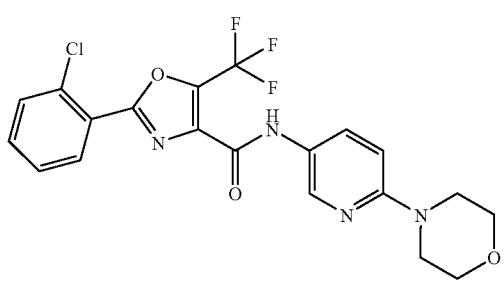

With a procedure similar to example 16 above, 2-(2-chloro-phenyl)-5-trifluoromethyl-oxazole-4-carboxylic acid (6-morpholin-4-yl-pyridin-3-yl)-amide was prepared from 2-(2-chloro-phenyl)-5-trifluoromethyl-oxazole-4-carboxylic acid and 6-morpholin-4-yl-pyridin-3-ylamine. LCMS calcd for C20H16ClF3N4O3 (m/e) 452, obsd 453 (M+H).

Example 65

Preparation of 2-(2-bromo-phenyl)-5-trifluoromethyl-oxazole-4-carboxylic acid {6-[(2-methoxy-ethyl)-methyl-amino]-pyridin-3-yl}-amide

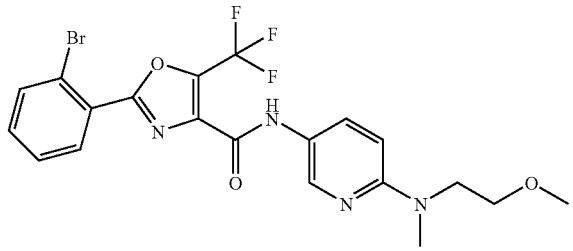

With a procedure similar to example 16 above, 2-(2-bromo-phenyl)-5-trifluoromethyl-oxazole-4-carboxylic acid {6-[(2-methoxy-ethyl)-methyl-amino]-pyridin-3-yl}-amide was prepared from 2-(2-bromo-phenyl)-5-trifluoromethyl-oxazole-4-carboxylic acid and $N^2$-(2-methoxy-ethyl)-$N^2$-methyl-pyridine-2,5-diamine. LCMS calcd for C20H18BrF3N4O3 (m/e) 499, obsd 500 (M+H).

Example 66

Preparation of 2-(2-bromo-phenyl)-5-trifluoromethyl-oxazole-4-carboxylic acid [6-(ethyl-methyl-amino)-pyridin-3-yl]-amide

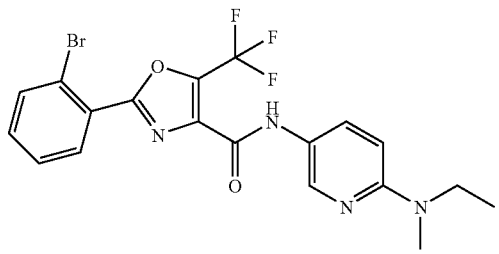

With a procedure similar to example 16 above, 2-(2-bromo-phenyl)-5-trifluoromethyl-oxazole-4-carboxylic acid [6-(ethyl-methyl-amino)-pyridin-3-yl]-amide was prepared from 2-(2-bromo-phenyl)-5-trifluoromethyl-oxazole-4-carboxylic acid and $N^2$-ethyl-$N^2$-methyl-pyridine-2,5-diamine. LCMS calcd for C19H16BrF3N4O2 (m/e) 469, obsd 470 (M+H).

Example 67

Preparation of 2-(2-bromo-phenyl)-5-trifluoromethyl-oxazole-4-carboxylic acid {6-[(2-cyclopropylmethoxy-ethyl)-methyl-amino]-pyridin-3-yl}-amide

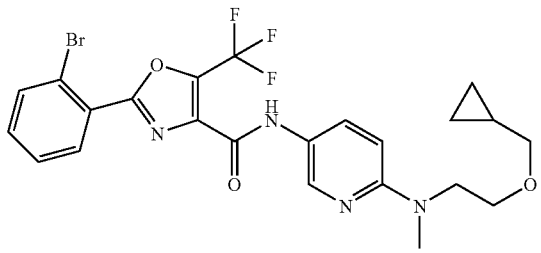

With a procedure similar to example 16 above, 2-(2-bromo-phenyl)-5-trifluoromethyl-oxazole-4-carboxylic acid {6-[(2-cyclopropylmethoxy-ethyl)-methyl-amino]-pyridin-3-yl}-amide was prepared from 2-(2-bromo-phenyl)-5-trifluoromethyl-oxazole-4-carboxylic acid and $N^2$-(2-cyclopropylmethoxy-ethyl)-$N^2$-methyl-pyridine-2,5-diamine. LCMS calcd for C23H22BrF3N4O3 (m/e) 539, obsd 540 (M+H).

Example 68

Preparation of 2-(2-bromo-phenyl)-5-trifluoromethyl-oxazole-4-carboxylic acid {2-[(2-methoxy-ethyl)-methyl-amino]-pyrimidin-5-yl}-amide

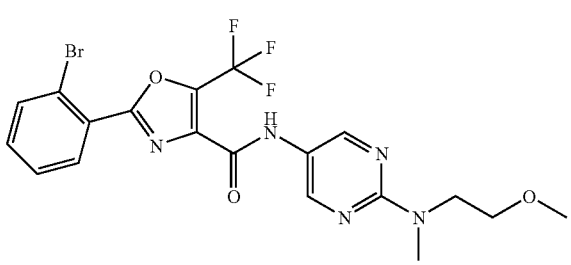

With a procedure similar to example 16 above, 2-(2-bromo-phenyl)-5-trifluoromethyl-oxazole-4-carboxylic acid {2-[(2-methoxy-ethyl)-methyl-amino]-pyrimidin-5-yl}-amide was prepared from 2-(2-bromo-phenyl)-5-trifluoromethyl-oxazole-4-carboxylic acid and $N^2$-(2-methoxy-ethyl)-$N^2$-methyl-pyrimidine-2,5-diamine. LCMS calcd for C19H17BrF3N5O3 (m/e) 500, obsd 501 (M+H).

Example 69

Preparation of 2-(2-ethyl-phenyl)-5-trifluoromethyl-oxazole-4-carboxylic acid {6-[(2-methoxy-ethyl)-methyl-amino]-pyridin-3-yl}-amide

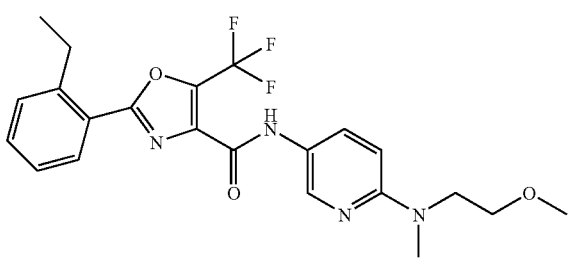

With a procedure similar to example 16 above, 2-(2-ethyl-phenyl)-5-trifluoromethyl-oxazole-4-carboxylic acid {6-[(2-methoxy-ethyl)-methyl-amino]-pyridin-3-yl}-amide was prepared from 2-(2-ethyl-phenyl)-5-trifluoromethyl-oxazole-4-carboxylic acid and $N^2$-(2-methoxy-ethyl)-$N^2$-methyl-pyridine-2,5-diamine. LCMS calcd for C22H23F3N4O3 (m/e) 448, obsd 449 (M+H).

Example 70

Preparation of 2-cyclohexyl-5-trifluoromethyl-oxazole-4-carboxylic acid {6-[(2-methoxy-ethyl)-methyl-amino]-pyridin-3-yl}-amide

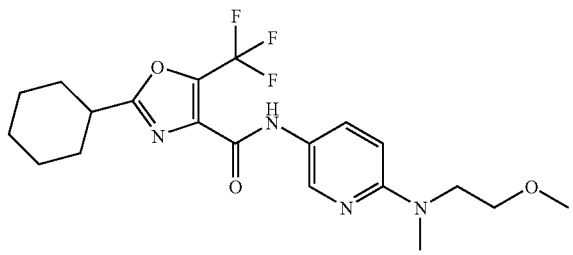

With a procedure similar to example 16 above, 2-cyclohexyl-5-trifluoromethyl-oxazole-4-carboxylic acid {6-[(2-methoxy-ethyl)-methyl-amino]-pyridin-3-yl}-amide was prepared from 2-cyclohexyl-5-trifluoromethyl-oxazole-4-carboxylic acid and $N^2$-(2-methoxy-ethyl)-$N^2$-methyl-pyridine-2,5-diamine. LCMS calcd for C20H25F3N4O3 (m/e) 426, obsd 427 (M+H).

Example 71

Preparation of 2-(2-trifluoromethoxy-phenyl)-5-trifluoromethyl-oxazole-4-carboxylic acid {6-[(2-methoxy-ethyl)-methyl-amino]-pyridin-3-yl}-amide

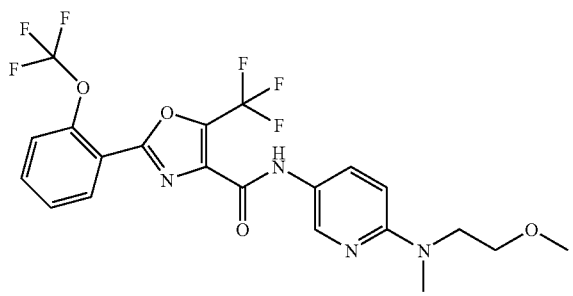

With a procedure similar to example 16 above, 2-(2-trifluoromethoxy-phenyl)-5-trifluoromethyl-oxazole-4-carboxylic acid {6-[(2-methoxy-ethyl)-methyl-amino]-pyridin-3-yl}-amide was prepared from 2-(2-trifluoromethoxy-phenyl)-5-trifluoromethyl-oxazole-4-carboxylic acid and $N^2$-(2-methoxy-ethyl)-$N^2$-methyl-pyridine-2,5-diamine. LCMS calcd for C21H18F6N4O4 (m/e) 504. obsd 505 (M+H).

Example 72

Preparation of 2-(2-trifluoromethoxy-phenyl)-5-trifluoromethyl-oxazole-4-carboxylic acid {2-[(2-methoxy-ethyl)-methyl-amino]-pyrimidin-5-yl}-amide

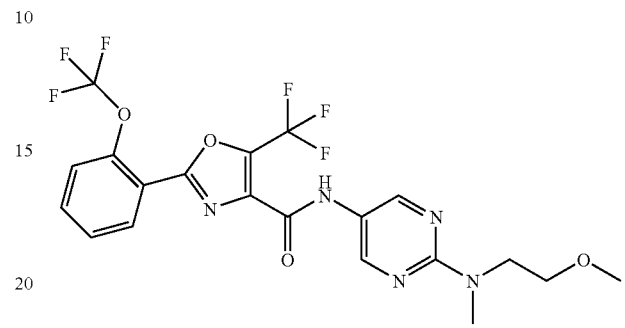

With a procedure similar to example 16 above, 2-(2-trifluoromethoxy-phenyl)-5-trifluoromethyl-oxazole-4-carboxylic acid {2-[(2-methoxy-ethyl)-methyl-amino]-pyrimidin-5-yl}-amide was prepared from 2-(2-trifluoromethoxy-phenyl)-5-trifluoromethyl-oxazole-4-carboxylic acid and N-(2-methoxy-ethyl)-N-methyl-pyrimidine-2,5-diamine. LCMS calcd for C20H17F6N5O4 (m/e) 505. obsd 506 (M+H).

Example 73

Preparation of 2-(2-methoxy-phenyl)-5-trifluoromethyl-oxazole-4-carboxylic acid {6-[(2-methoxy-ethyl)-methyl-amino]-pyridin-3-yl}-amide

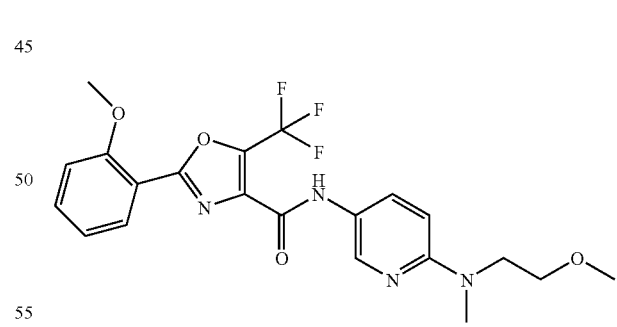

With a procedure similar to example 16 above, 2-(2-methoxy-phenyl)-5-trifluoromethyl-oxazole-4-carboxylic acid {6-[(2-methoxy-ethyl)-methyl-amino]-pyridin-3-yl}-amide was prepared from 2-(2-methoxy-phenyl)-5-trifluoromethyl-oxazole-4-carboxylic acid and $N^2$-(2-methoxy-ethyl)-$N^2$-methyl-pyridine-2,5-diamine. LCMS calcd for C21H21F3N4O4 (m/e) 504. obsd 505 (M+H).

Example 74

Preparation of 2-(2-methoxy-phenyl)-5-trifluoromethyl-oxazole-4-carboxylic acid {2-[(2-methoxy-ethyl)-methyl-amino]-pyrimidin-5-yl}-amide

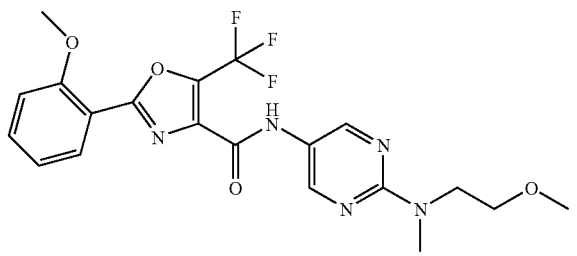

With a procedure similar to example 16 above, 2-(2-methoxy-phenyl)-5-trifluoromethyl-oxazole-4-carboxylic acid {2-[(2-methoxy-ethyl)-methyl-amino]-pyrimidin-5-yl}-amide was prepared from 2-(2-methoxy-phenyl)-5-trifluoromethyl-oxazole-4-carboxylic acid and N-(2-methoxy-ethyl)-N-methyl-pyrimidine-2,5-diamine. LCMS calcd for C20H20F3N5O4 (m/e) 451. obsd 452 (M+H).

Example 75

Preparation of 2-phenyl-5-propyl-oxazole-4-carboxylic acid {6-[(2-methoxy-ethyl)-methyl-amino]-pyridin-3-yl}-amide

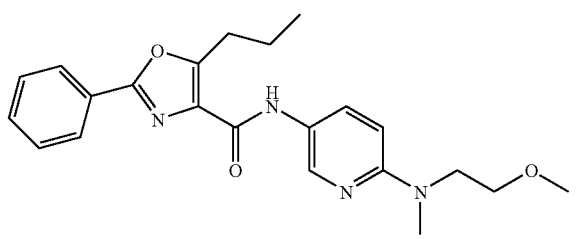

With a procedure similar to example 16 above, 2-phenyl-5-propyl-oxazole-4-carboxylic acid {6-[(2-methoxy-ethyl)-methyl-amino]-pyridin-3-yl}-amide was prepared from 2-phenyl-5-propyl-oxazole-4-carboxylic acid and $N^2$-(2-methoxy-ethyl)-$N^2$-methyl-pyridine-2,5-diamine. LCMS calcd for C22H26N4O3 (m/e) 394, obsd 395 (M+H).

Example 76

Preparation of 2-phenyl-5-propyl-oxazole-4-carboxylic acid (6-morpholin-4-yl-pyridin-3-yl)-amide

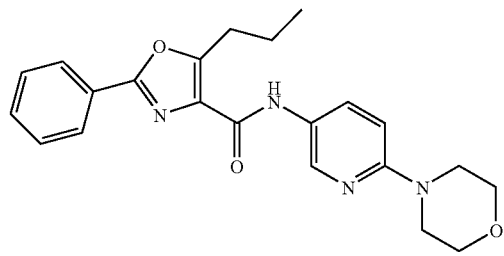

With a procedure similar to example 16 above, 2-phenyl-5-propyl-oxazole-4-carboxylic acid (6-morpholin-4-yl-pyridin-3-yl)-amide was prepared from 2-phenyl-5-propyl-oxazole-4-carboxylic acid and 6-morpholin-4-yl-pyridin-3-ylamine. LCMS calcd for C22H24N4O3 (m/e) 392, obsd 393 (M+H).

Example 77

Preparation of 2-(2-chloro-phenyl)-5-propyl-oxazole-4-carboxylic acid {6-[(2-methoxy-ethyl)-methyl-amino]-pyridin-3-yl}-amide

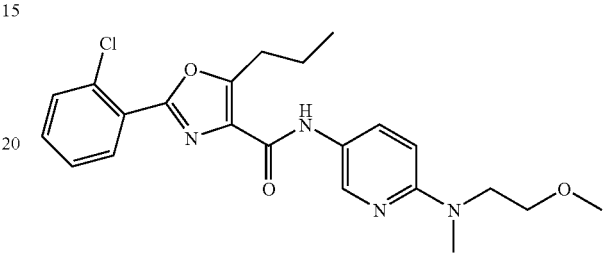

With a procedure similar to example 16 above, 2-(2-chloro-phenyl)-5-propyl-oxazole-4-carboxylic acid {6-[(2-methoxy-ethyl)-methyl-amino]-pyridin-3-yl}-amide was prepared from 2-(2-chloro-phenyl)-5-propyl-oxazole-4-carboxylic acid and $N^2$-(2-methoxy-ethyl)-$N^2$-methyl-pyridine-2,5-diamine. LCMS calcd for C22H25ClN4O3 (m/e) 428, obsd 429 (M+H).

Example 78

Preparation of 2-(2-bromo-phenyl)-5-propyl-oxazole-4-carboxylic acid {6-[(2-methoxy-ethyl)-methyl-amino]-pyridin-3-yl}-amide

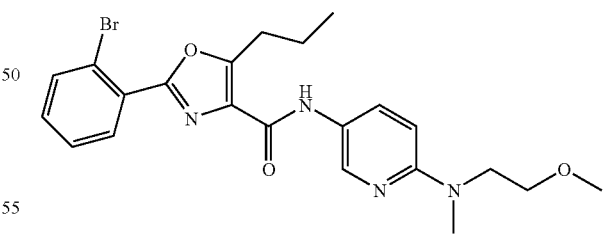

With a procedure similar to example 16 above, 2-(2-bromo-phenyl)-5-propyl-oxazole-4-carboxylic acid {6-[(2-methoxy-ethyl)-methyl-amino]-pyridin-3-yl}-amide was prepared from 2-(2-bromo-phenyl)-5-propyl-oxazole-4-carboxylic acid and $N^2$-(2-methoxy-ethyl)-$N^2$-methyl-pyridine-2,5-diamine. LCMS calcd for C22H25BrN4O3 (m/e) 473, obsd 474 (M+H).

Example 79

Preparation of 5-propyl-2-o-tolyl-oxazole-4-carboxylic acid {6-[(2-methoxy-ethyl)-methyl-amino]-pyridin-3-yl}-amide

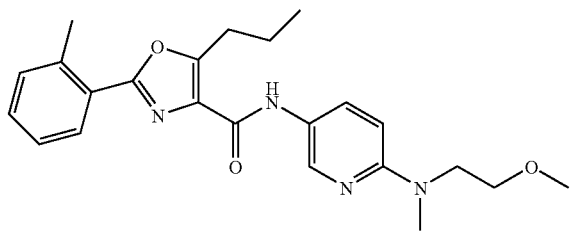

With a procedure similar to example 16 above, 5-propyl-2-o-tolyl-oxazole-4-carboxylic acid {6-[(2-methoxy-ethyl)-methyl-amino]-pyridin-3-yl}-amide was prepared from 2-(2-bromo-phenyl)-5-propyl-oxazole-4-carboxylic acid and $N^2$-(2-methoxy-ethyl)-$N^2$-methyl-pyridine-2,5-diamine. LCMS calcd for C23H28N4O3 (m/e) 408, obsd 409 (M+H).

Example 80

Preparation of 2-(2-chloro-phenyl)-5-propyl-oxazole-4-carboxylic acid [6-(ethyl-methyl-amino)-pyridin-3-yl]-amide

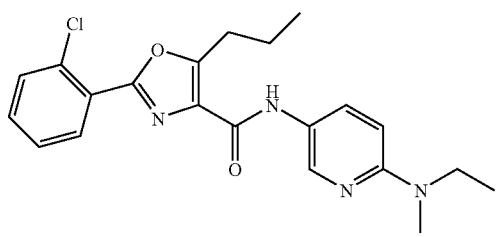

With a procedure similar to example 16 above, 2-(2-chloro-phenyl)-5-propyl-oxazole-4-carboxylic acid [6-(ethyl-methyl-amino)-pyridin-3-yl]-amide was prepared from 2-(2-chloro-phenyl)-5-propyl-oxazole-4-carboxylic acid and $N^2$-ethyl-$N^2$-methyl-pyridine-2,5-diamine. LCMS calcd for C21H23ClN4O2 (m/e) 398, obsd 399 (M+H).

Example 81

Preparation of 2-cyclohexyl-5-propyl-oxazole-4-carboxylic acid {6-[(2-methoxy-ethyl)-methyl-amino]-pyridin-3-yl}-amide

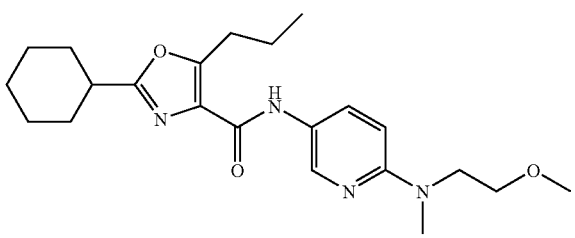

With a procedure similar to example 16 above, 2-cyclohexyl-5-propyl-oxazole-4-carboxylic acid {6-[(2-methoxy-ethyl)-methyl-amino]-pyridin-3-yl}-amide was prepared from 2-cyclohexyl-5-propyl-oxazole-4-carboxylic acid and $N^2$-(2-methoxy-ethyl)-$N^2$-methyl-pyridine-2,5-diamine. LCMS calcd for C22H32N4O3 (m/e) 400, obsd 401 (M+H).

Example 82

Preparation of 2-phenyl-5-trifluoromethyl-oxazole-4-carboxylic acid [6-(2-hydroxy-ethylamino)-pyridin-3-yl]-amide

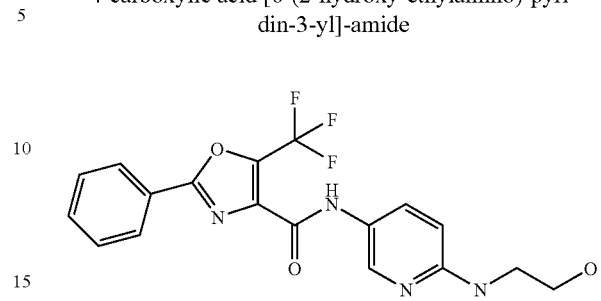

A mixture of 2-phenyl-5-trifluoromethyl-oxazole-4-carboxylic acid (311 mg, 1.21 mmol), 2-(5-amino-pyridin-2-ylamino)-ethanol (84 mg, 0.55 mmol), N-hydroxybenzotriazole (185 mg, 1.38 mmol), and 1-ethyl-3-(3-dimethylaminopropyl)carbodiimide hydrochloride (264 mg, 1.38 mmol) in a mixture of methylene chloride (5 mL) and DMF (1 mL) was stirred at room temperature for 5 hr. The solvents were removed, and lithium hydroxide hydrate (excess) in a mixed solvent of methanol, tetrahydrofuran, and water (3:1:1, 5 mL) was added. The reaction mixture was stirred at room temperature for overnight. Solvents were removed, and water was added. The resulted mixture was extracted twice with ethyl acetate. The organic layers were collected, and washed with water, brine, dried over sodium sulfate, filtered, and concentrated in vacuo. Flash chromatography (Merck silica gel 60, 230-400 mesh, 0-15% methanol in methylene chloride for 30 min), and then preparative HPLC (0-90% acetonitrile in water for 20 min), followed by lyophilization gave 2-phenyl-5-trifluoromethyl-oxazole-4-carboxylic acid [6-(2-hydroxy-ethylamino)-pyridin-3-yl]-amide as a light yellow solid. LCMS calcd for C18H15F3N4O3 (m/e) 392, obsd 393 (M+H).

Example 83

Preparation of 2-phenyl-5-trifluoromethyl-oxazole-4-carboxylic acid {6-[(2-hydroxy-ethyl)-methyl-amino]-pyridin-3-yl}-amide

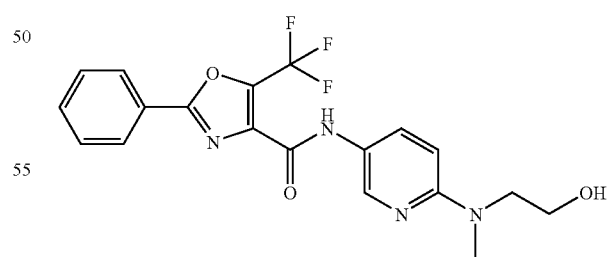

With a procedure similar to example 43 above, 2-phenyl-5-trifluoromethyl-oxazole-4-carboxylic acid {6-[(2-hydroxy-ethyl)-methyl-amino]-pyridin-3-yl}-amide was prepared from 2-phenyl-5-trifluoromethyl-oxazole-4-carboxylic acid and 2-[(5-amino-pyridin-2-yl)-methyl-amino]-ethanol. LCMS calcd for C19H17F3N4O3 (m/e) 406, obsd 407 (M+H).

Example 84

Preparation of 2-phenyl-5-trifluoromethyl-oxazole-4-carboxylic acid [6-(3-hydroxy-pyrrolidin-1-yl)-pyridin-3-yl]-amide

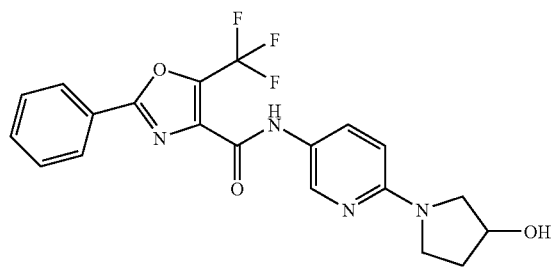

With a procedure similar to example 43 above, 2-phenyl-5-trifluoromethyl-oxazole-4-carboxylic acid [6-(3-hydroxy-pyrrolidin-1-yl)-pyridin-3-yl]-amide was prepared from 2-phenyl-5-trifluoromethyl-oxazole-4-carboxylic acid and 1-(5-amino-pyridin-2-yl)-pyrrolidin-3-ol. LCMS calcd for C20H17F3N4O3 (m/e) 418, obsd 419 (M+H).

Example 85

Preparation of 2-phenyl-5-trifluoromethyl-oxazole-4-carboxylic acid-[2-(3-hydroxypyrrolidin-1-yl)-pyrimidin-5-yl]amide

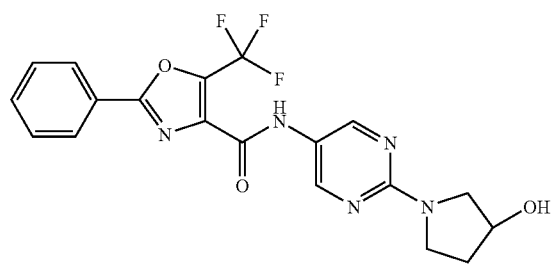

With a method similar to example 43 above, 2-phenyl-5-trifluoromethyl-oxazole-4-carboxylic acid-[2-(3-hydroxy-pyrrolidin-1-yl)pyrimidin-5-yl]amide was prepared from 2-phenyl-5-trifluoromethyl-oxazole-4-carboxylic acid and N-(5-amino-pyrimidin-2-yl)-pyrrolidin-3-ol. LCMS calcd for C19H16F3N5O3 m/e 419.37, obsd 420.0 (ES, M+H).

Example 86

Preparation of (R)-2-phenyl-5-trifluoromethyl-oxazole-4-carboxylic acid-[2-(3-hydroxypyrrolidin-1-yl)pyrimidin-5-yl]amide

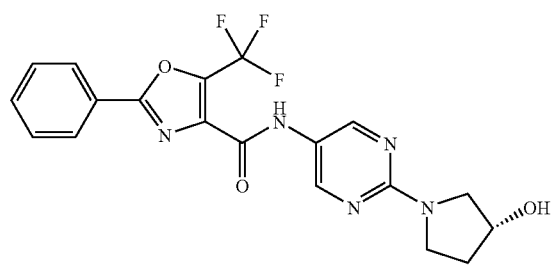

With a method similar to example 43 above, (R)-2-phenyl-5-trifluoromethyl-oxazole-4-carboxylic acid-[2-(3-hydroxy-pyrrolidin-1-yl)pyrimidin-5-yl]amide was prepared from 2-phenyl-5-trifluoromethyl-oxazole-4-carboxylic acid and (R)—N-(5-aminopyrimidin-2-yl)-pyrrolidin-3-ol. LCMS calcd for C19H16F3N5O3 m/e 419.37, obsd 420.1 (ES, M+H).

Example 87

Preparation of (S)-2-phenyl-5-trifluoromethyl-oxazole-4-carboxylic acid-[2-(3-hydroxypyrrolidin-1-yl)pyrimidin-5-yl]amide

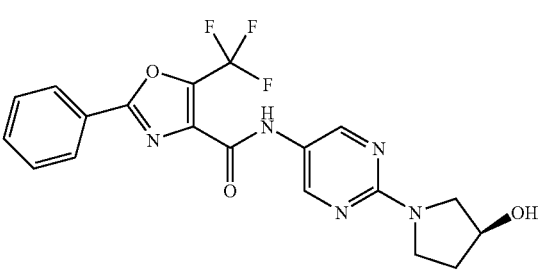

With a method similar to example 43 above, (S)-2-phenyl-5-trifluoromethyl-oxazole-4-carboxylic acid-[2-(3-hydroxy-pyrrolidin-1-yl)pyrimidin-5-yl]amide was prepared from 2-phenyl-5-trifluoromethyl-oxazole-4-carboxylic acid and (S)—N-(5-aminopyrimidin-2-yl)-pyrrolidin-3-ol. LCMS calcd for C19H16F3N5O3 m/e 419.37, obsd 420.1 (ES, M+H).

Example 88

Preparation of 2-phenyl-5-trifluoromethyl-oxazole-4-carboxylic acid (3-hydroxy-3,4,5,6-tetrahydro-2H-[1,2']bipyridinyl-5'-yl)-amide

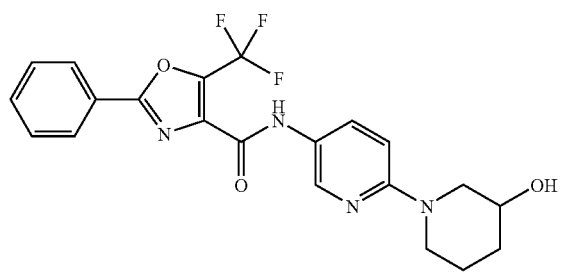

With a procedure similar to example 43 above, 2-phenyl-5-trifluoromethyl-oxazole-4-carboxylic acid (3-hydroxy-3,4,5,6-tetrahydro-2H-[1,2']bipyridinyl-5'-yl)-amide was prepared from 2-phenyl-5-trifluoromethyl-oxazole-4-carboxylic acid and 5'-amino-3,4,5,6-tetrahydro-2H-[1,2']bipyridinyl-3-ol. LCMS calcd for C21H19F3N4O3 (m/e) 432, obsd 433 (M+H).

Example 89

Preparation of 2-phenyl-5-trifluoromethyl-oxazole-4-carboxylic acid [6-((S)-2-hydroxymethyl-pyrrolidin-1-yl)-pyridin-3-yl]-amide

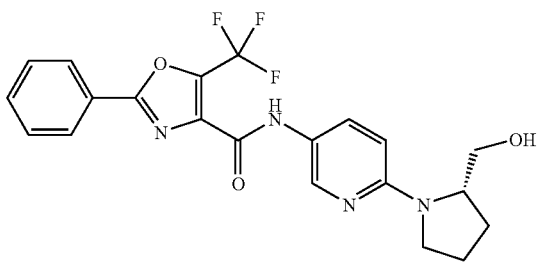

With a procedure similar to example 43 above, 2-phenyl-5-trifluoromethyl-oxazole-4-carboxylic acid [6-((S)-2-hydroxymethyl-pyrrolidin-1-yl)-pyridin-3-yl]-amide was prepared from 2-phenyl-5-trifluoromethyl-oxazole-4-carboxylic acid and [(S)-1-(5-amino-pyridin-2-yl)-pyrrolidin-2-yl]-methanol. LCMS calcd for C21H19F3N4O3 (m/e) 432, obsd 433 (M+H).

Example 90

Preparation of 2-phenyl-5-trifluoromethyl-oxazole-4-carboxylic acid (4-hydroxy-3,4,5,6-tetrahydro-2H-[1,2']bipyridinyl-5'-yl)-amide

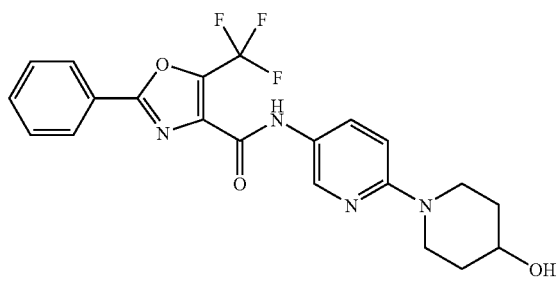

With a procedure similar to example 43 above, 2-phenyl-5-trifluoromethyl-oxazole-4-carboxylic acid (4-hydroxy-3,4,5,6-tetrahydro-2H-[1,2']bipyridinyl-5'-yl)-amide was prepared from 2-phenyl-5-trifluoromethyl-oxazole-4-carboxylic acid and 5'-amino-3,4,5,6-tetrahydro-2H-[1,2']bipyridinyl-4-ol. LCMS calcd for C21H19F3N4O3 (m/e) 432, obsd 433 (M+H).

Example 91

Preparation of 2-phenyl-5-trifluoromethyl-oxazole-4-carboxylic acid [6-((S)-2-hydroxy-1-methyl-ethylamino)-pyridin-3-yl]-amide

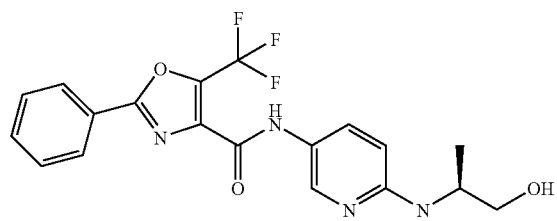

With a procedure similar to example 43 above, 2-phenyl-5-trifluoromethyl-oxazole-4-carboxylic acid [6-((S)-2-hydroxy-1-methyl-ethylamino)-pyridin-3-yl]-amide was prepared from 2-phenyl-5-trifluoromethyl-oxazole-4-carboxylic acid and (S)-2-(5-amino-pyridin-2-ylamino)-propan-1-ol. LCMS calcd for C19H17F3N4O3 (m/e) 406, obsd 407 (M+H).

Example 92

Preparation of 2-phenyl-5-trifluoromethyl-oxazole-4-carboxylic acid [2-((S)-2-hydroxy-1-methyl-ethylamino)-pyrimidin-5-yl]-amide

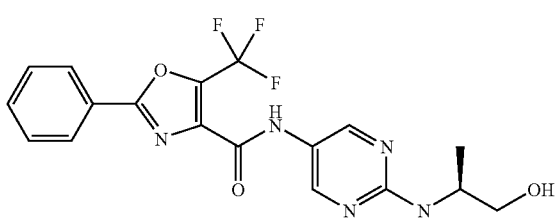

With a procedure similar to example 43 above, 2-phenyl-5-trifluoromethyl-oxazole-4-carboxylic acid [2-((S)-2-hydroxy-1-methyl-ethylamino)-pyrimidin-5-yl]-amide was prepared from 2-phenyl-5-trifluoromethyl-oxazole-4-carboxylic acid and (S)-2-(5-amino-pyrimidin-2-ylamino)-propan-1-ol. LCMS calcd for C18H16F3N5O3 (m/e) 407, obsd 408 (M+H).

Example 93

Preparation of 2-phenyl-5-trifluoromethyl-oxazole-4-carboxylic acid [6-(2-hydroxy-1,1-dimethyl-ethylamino)-pyridin-3-yl]-amide

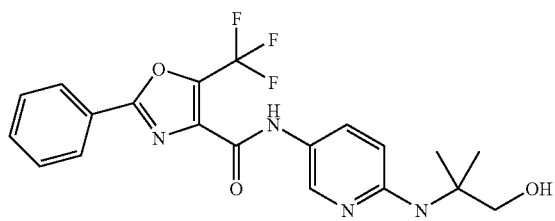

With a procedure similar to example 43 above, 2-phenyl-5-trifluoromethyl-oxazole-4-carboxylic acid [6-(2-hydroxy-1,1-dimethyl-ethylamino)-pyridin-3-yl]-amide was prepared from 2-phenyl-5-trifluoromethyl-oxazole-4-carboxylic acid and 2-(5-Amino-pyridin-2-ylamino)-2-methyl-propan-1-ol. LCMS calcd for C20H19F3N4O3 (m/e) 420, obsd 421 (M+H).

Example 94

Preparation of 2-(2-bromo-phenyl)-5-trifluoromethyl-oxazole-4-carboxylic acid [6-((S)-3-hydroxy-pyrrolidin-1-yl)-pyridin-3-yl]-amide

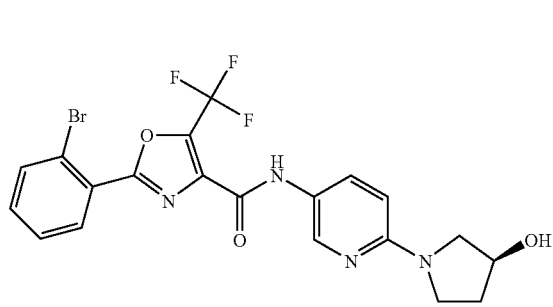

With a method similar to example 43 above, 2-(2-bromo-phenyl)-5-trifluoromethyl-oxazole-4-carboxylic acid [6-((S)-3-hydroxy-pyrrolidin-1-yl)-pyridin-3-yl]-amide was prepared from 2-(2-bromo-phenyl)-5-trifluoromethyl-oxazole-4-carboxylic acid and (S)-1-(5-Amino-pyridin-2-yl)-pyrrolidin-3-ol. LCMS calcd for C20H16BrF3N4O3 m/e 497, obsd 498.

Example 95

Preparation of 2-(2-chloro-phenyl)-4-ethyl-oxazole-5-carboxylic acid (6-morpholin-4-yl-pyridin-3-yl)-amide

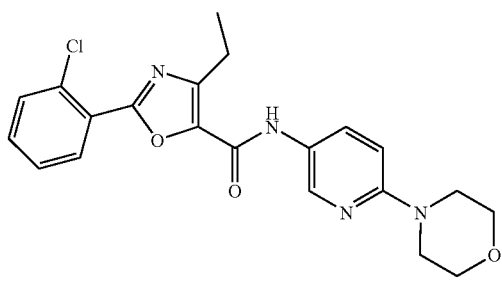

A mixture of 2-(2-chloro-phenyl)-4-ethyl-oxazole-5-carboxylic acid 2,5-dioxo-pyrrolidin-1-yl ester (174 mg, 0.5 mmol) and 6-morpholin-4-yl-pyridin-3-ylamine (90 mg, 0.5 mmol) in 5 mL of acetonitrile was stirred at 85° C. overnight. The solvent was removed in vacuo, and the crude product was purified by flash chromatography (Merck silica gel 60, 230-400 mesh, 0-15% methanol in methylene chloride for 30 min) to yield 2-(2-chloro-phenyl)-4-ethyl-oxazole-5-carboxylic acid (6-morpholin-4-yl-pyridin-3-yl)-amide (107 mg, 52% yield) as a light yellow solid. LCMS calcd for C21H21ClN4O3 (m/e) 412, obsd 413 (M+H).

Example 96

Preparation of 2-(2-chloro-phenyl)-4-propyl-oxazole-5-carboxylic acid (6-morpholin-4-yl-pyridin-3-yl)-amide

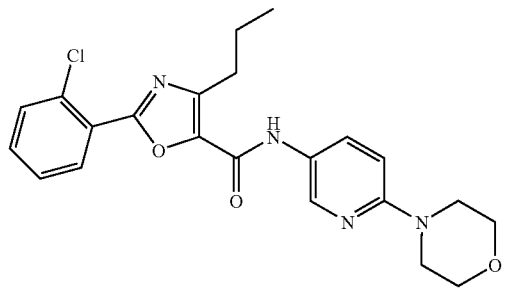

With a procedure similar to example 50 above, 2-(2-chloro-phenyl)-4-propyl-oxazole-5-carboxylic acid (6-morpholin-4-yl-pyridin-3-yl)-amide was prepared from 2-(2-chloro-phenyl)-4-propyl-oxazole-5-carboxylic acid 2,5-dioxo-pyrrolidin-1-yl ester and 6-morpholin-4-yl-pyridin-3-ylamine. LCMS calcd for C22H23ClN4O3 (m/e) 426, obsd 427 (M+H).

Example 97

Preparation of 4-methyl-2-o-tolyl-oxazole-5-carboxylic acid (6-morpholin-4-yl-pyridin-3-yl)-amide

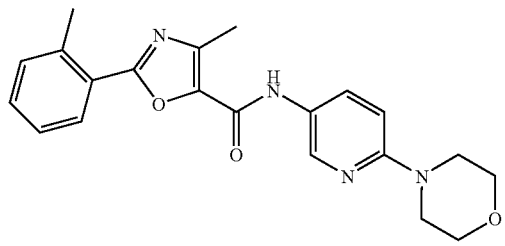

With a procedure similar to example 50 above, 4-methyl-2-o-tolyl-oxazole-5-carboxylic acid (6-morpholin-4-yl-pyridin-3-yl)-amide was prepared from 4-methyl-2-o-tolyl-oxazole-5-carboxylic acid 2,5-dioxo-pyrrolidin-1-yl ester and 6-morpholin-4-yl-pyridin-3-ylamine. LCMS calcd for C21H22N4O3 (m/e) 378, obsd 379 (M+H).

Example 98

Preparation of 4-propyl-2-o-tolyl-oxazole-5-carboxylic acid (6-morpholin-4-yl-pyridin-3-yl)-amide

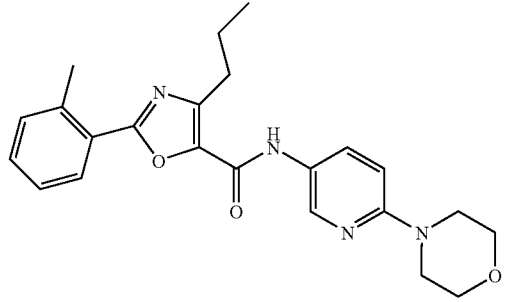

With a procedure similar to example 50 above, 4-propyl-2-o-tolyl-oxazole-5-carboxylic acid (6-morpholin-4-yl-pyridin-3-yl)-amide was prepared from 4-propyl-2-o-tolyl-oxazole-5-carboxylic acid 2,5-dioxo-pyrrolidin-1-yl ester and 6-morpholin-4-yl-pyridin-3-ylamine. LCMS calcd for C23H26N4O3 (m/e) 406, obsd 407 (M+H).

Example 99

Preparation of 4-methyl-2-phenyl-oxazole-5-carboxylic acid (6-morpholin-4-yl-pyridin-3-yl)-amide

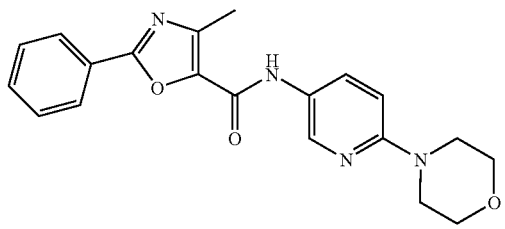

With a procedure similar to example 50 above, 4-methyl-2-phenyl-oxazole-5-carboxylic acid (6-morpholin-4-yl-pyridin-3-yl)-amide was prepared from 4-methyl-2-phenyl-oxazole-5-carboxylic acid 2,5-dioxo-pyrrolidin-1-yl ester and 6-morpholin-4-yl-pyridin-3-ylamine. LCMS calcd for C20H20N4O3 (m/e) 364, obsd 365 (M+H).

Example 100

Preparation of 4-(2-methylsulfanyl-ethyl)-2-phenyl-oxazole-5-carboxylic acid (6-morpholin-4-yl-pyridin-3-yl)-amide

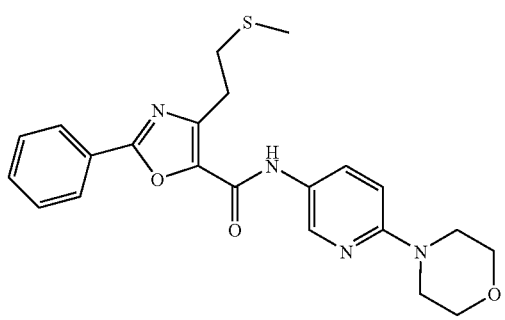

With a procedure similar to example 50 above, 4-(2-methylsulfanyl-ethyl)-2-phenyl-oxazole-5-carboxylic acid (6-morpholin-4-yl-pyridin-3-yl)-amide was prepared from 4-(2-methylsulfanyl-ethyl)-2-phenyl-oxazole-5-carboxylic acid 2,5-dioxo-pyrrolidin-1-yl ester and 6-morpholin-4-yl-pyridin-3-ylamine. LCMS calcd for C22H24N4O3S (m/e) 424, obsd 425 (M+H).

Example 101

Preparation of 2-(2-chloro-phenyl)-4-ethyl-oxazole-5-carboxylic acid {6-[(2-methoxy-ethyl)-methyl-amino]-pyridin-3-yl}-amide

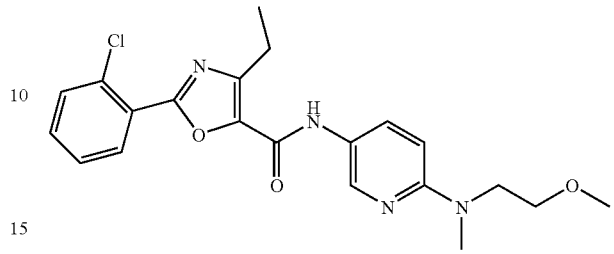

With a procedure similar to example 50 above, 2-(2-chloro-phenyl)-4-ethyl-oxazole-5-carboxylic acid {6-[(2-methoxy-ethyl)-methyl-amino]-pyridin-3-yl}-amide was prepared from 2-(2-chloro-phenyl)-4-ethyl-oxazole-5-carboxylic acid 2,5-dioxo-pyrrolidin-1-yl ester and $N^2$-(2-methoxy-ethyl)-$N^2$-methyl-pyridine-2,5-diamine. LCMS calcd for C21H23ClN4O3 (m/e) 414, obsd 415 (M+H).

Example 102

Preparation of 2-(2-chloro-phenyl)-4-propyl-oxazole-5-carboxylic acid {6-[(2-methoxy-ethyl)-methyl-amino]-pyridin-3-yl}-amide

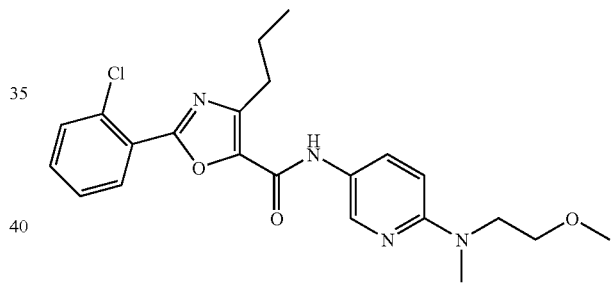

With a procedure similar to example 50 above, 2-(2-chloro-phenyl)-4-propyl-oxazole-5-carboxylic acid {6-[(2-methoxy-ethyl)-methyl-amino]-pyridin-3-yl}-amide was prepared from 2-(2-chloro-phenyl)-4-propyl-oxazole-5-carboxylic acid 2,5-dioxo-pyrrolidin-1-yl ester and $N^2$-(2-methoxy-ethyl)-$N^2$-methyl-pyridine-2,5-diamine. LCMS calcd for C22H25ClN4O3 (m/e) 428, obsd 429 (M+H).

Example 103

Preparation of 2-phenyl-4-propyl-oxazole-5-carboxylic acid {6-[(2-methoxy-ethyl)-methyl-amino]-pyridin-3-yl}-amide

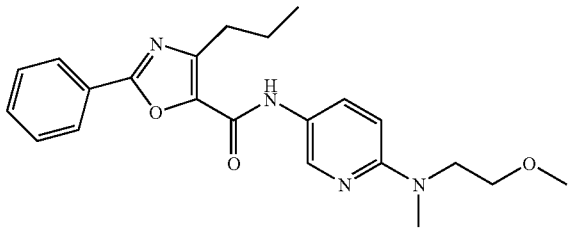

With a procedure similar to example 50 above, 2-phenyl-4-propyl-oxazole-5-carboxylic acid {6-[(2-methoxy-ethyl)-methyl-amino]-pyridin-3-yl}-amide was prepared from 2-phenyl-4-propyl-oxazole-5-carboxylic acid 2,5-dioxo-pyrrolidin-1-yl ester and $N^2$-(2-methoxy-ethyl)-$N^2$-methyl-pyridine-2,5-diamine. LCMS calcd for C22H26N4O3 (m/e) 394, obsd 395 (M+H).

Example 104

Preparation of 2-cyclohexyl-4-propyl-oxazole-5-carboxylic acid {6-[(2-methoxy-ethyl)-methyl-amino]-pyridin-3-yl}-amide

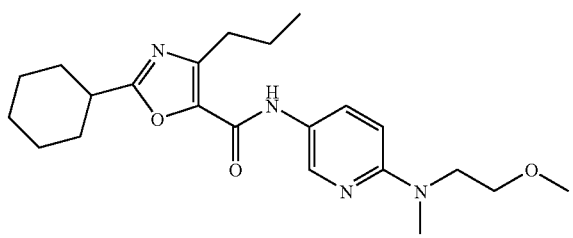

With a procedure similar to example 50 above, 2-cyclohexyl-4-propyl-oxazole-5-carboxylic acid {6-[(2-methoxy-ethyl)-methyl-amino]-pyridin-3-yl}-amide was prepared from 2-cyclohexyl-4-propyl-oxazole-5-carboxylic acid 2,5-dioxo-pyrrolidin-1-yl ester and $N^2$-(2-methoxy-ethyl)-$N^2$-methyl-pyridine-2,5-diamine. LCMS calcd for C22H32N4O3 (m/e) 400, obsd 401 (M+H).

Example 105

Preparation of 2-cyclohexyl-4-propyl-oxazole-5-carboxylic acid (6-morpholin-4-yl-pyridin-3-yl)-amide

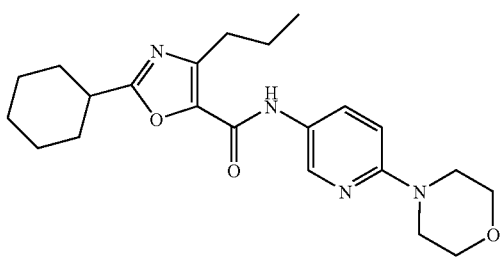

With a procedure similar to example 50 above, 2-cyclohexyl-4-propyl-oxazole-5-carboxylic acid (6-morpholin-4-yl-pyridin-3-yl)-amide was prepared from 2-cyclohexyl-4-propyl-oxazole-5-carboxylic acid 2,5-dioxo-pyrrolidin-1-yl ester and 6-morpholin-4-yl-pyridin-3-ylamine. LCMS calcd for C22H30N4O3 (m/e) 398, obsd 399 (M+H).

Example 106

Preparation of 2-phenyl-4-propyl-oxazole-5-carboxylic acid [6-(ethyl-methyl-amino)-pyridin-3-yl]-amide

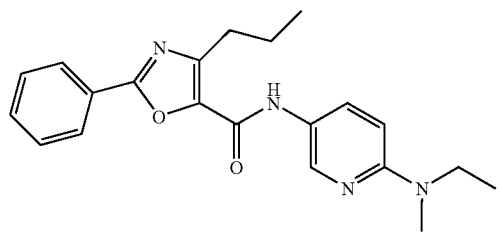

With a procedure similar to example 50 above, 2-phenyl-4-propyl-oxazole-5-carboxylic acid [6-(ethyl-methyl-amino)-pyridin-3-yl]-amide was prepared from 2-phenyl-4-propyl-oxazole-5-carboxylic acid 2,5-dioxo-pyrrolidin-1-yl ester and $N^2$-ethyl-$N^2$-methyl-pyridine-2,5-diamine. LCMS calcd for C21H24N4O2 (m/e) 364, obsd 365 (M+H).

Example 107

Preparation of 2-(2-bromo-phenyl)-4-propyl-oxazole-5-carboxylic acid {6-[(2-methoxy-ethyl)-methyl-amino]-pyridin-3-yl}-amide

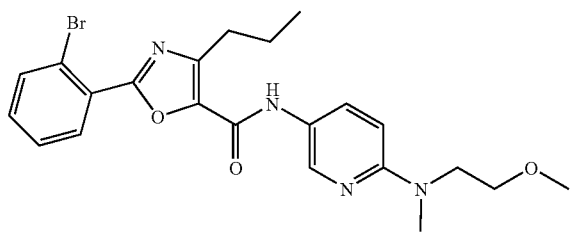

With a procedure similar to example 50 above, 2-(2-bromo-phenyl)-4-propyl-oxazole-5-carboxylic acid {6-[(2-methoxy-ethyl)-methyl-amino]-pyridin-3-yl}-amide was prepared from 2-(2-bromo-phenyl)-4-propyl-oxazole-5-carboxylic acid 2,5-dioxo-pyrrolidin-1-yl ester and $N^2$-(2-methoxy-ethyl)-$N^2$-methyl-pyridine-2,5-diamine. LCMS calcd for C22H25BrN4O3 (m/e) 473, obsd 474 (M+H).

Example 108

Preparation of 2-(2-bromo-phenyl)-4-propyl-oxazole-5-carboxylic acid {2-[(2-methoxy-ethyl)-methyl-amino]-pyrimidin-5-yl}-amide

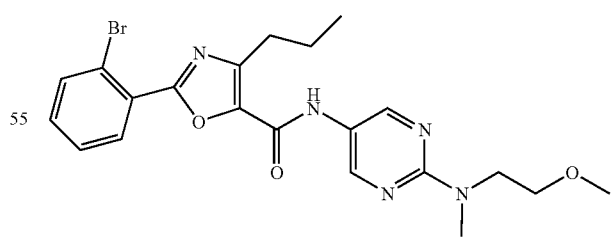

With a procedure similar to example 50 above, 2-(2-bromo-phenyl)-4-propyl-oxazole-5-carboxylic acid {2-[(2-methoxy-ethyl)-methyl-amino]-pyrimidin-5-yl}-amide was prepared from 2-(2-bromo-phenyl)-4-propyl-oxazole-5-carboxylic acid 2,5-dioxo-pyrrolidin-1-yl ester and N-(2-methoxy-ethyl)-N-methyl-pyrimidine-2,5-diamine. LCMS calcd for C21H24BrN5O3 (m/e) 474, obsd 475 (M+H).

Example 109

Preparation of 2-(2-bromo-phenyl)-4-propyl-oxazole-5-carboxylic acid [6-(cyclopropyl-methyl-amino)-pyridin-3-yl]-amide

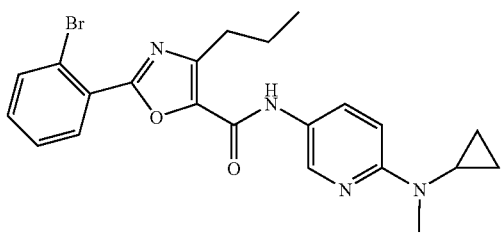

With a procedure similar to example 50 above, 2-(2-bromo-phenyl)-4-propyl-oxazole-5-carboxylic acid [6-(cyclopropyl-methyl-amino)-pyridin-3-yl]-amide was prepared from 2-(2-bromo-phenyl)-4-propyl-oxazole-5-carboxylic acid 2,5-dioxo-pyrrolidin-1-yl ester and $N^2$-cyclopropyl-$N^2$-methyl-pyridine-2,5-diamine. LCMS calcd for C22H23BrN4O2 (m/e) 455, obsd 456 (M+H).

Example 110

Preparation of 2-(2-chloro-phenyl)-4-propyl-oxazole-5-carboxylic acid [6-(cyclopropyl-methyl-amino)-pyridin-3-yl]-amide

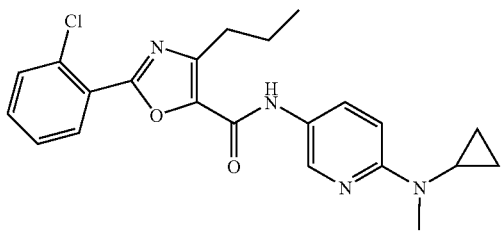

With a procedure similar to example 50 above, 2-(2-chloro-phenyl)-4-propyl-oxazole-5-carboxylic acid [6-(cyclopropyl-methyl-amino)-pyridin-3-yl]-amide was prepared from 2-(2-chloro-phenyl)-4-propyl-oxazole-5-carboxylic acid 2,5-dioxo-pyrrolidin-1-yl ester and $N^2$-cyclopropyl-$N^2$-methyl-pyridine-2,5-diamine. LCMS calcd for C22H23ClN4O2 (m/e) 410, obsd 411 (M+H).

Example 111

Preparation of 2-phenyl-4-trifluoromethyl-oxazole-5-carboxylic acid {6-[(2-methoxy-ethyl)-methyl-amino]-pyridin-3-yl}-amide

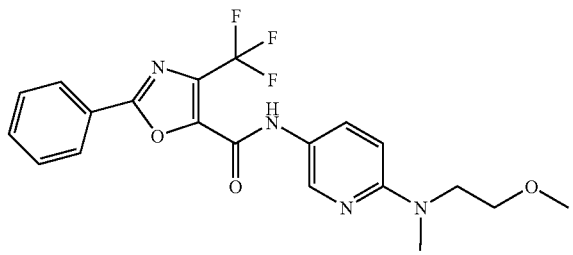

With a procedure similar to example 1 above, 2-phenyl-4-trifluoromethyl-oxazole-5-carboxylic acid {6-[(2-methoxy-ethyl)-methyl-amino]-pyridin-3-yl}-amide was prepared from 2-phenyl-4-trifluoromethyl-oxazole-5-carboxylic acid and $N^2$-(2-methoxy-ethyl)-$N^2$-methyl-pyridine-2,5-diamine. LCMS calcd for C20H19F3N4O3 (m/e) 420, obsd 421 (M+H).

Example 112

Preparation of 2-phenyl-4-trifluoromethyl-oxazole-5-carboxylic acid {2-[(2-methoxy-ethyl)-methyl-amino]-pyrimidin-5-yl}-amide

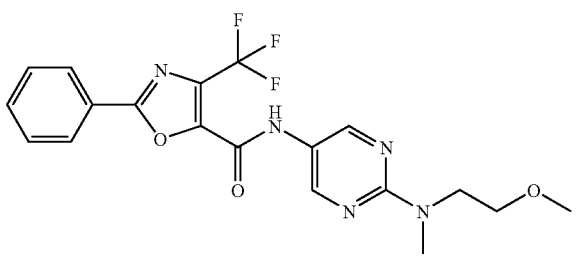

With a procedure similar to example 1 above, 2-phenyl-4-trifluoromethyl-oxazole-5-carboxylic acid {2-[(2-methoxy-ethyl)-methyl-amino]-pyrimidin-5-yl}-amide was prepared from 2-phenyl-4-trifluoromethyl-oxazole-5-carboxylic acid and N-(2-Methoxy-ethyl)-N-methyl-pyrimidine-2,5-diamine. LCMS calcd for C19H18F3N5O3 (m/e) 421, obsd 422 (M+H).

Example 113

Preparation of 2-(2-methoxy-phenyl)-4-trifluoromethyl-oxazole-5-carboxylic acid {6-[(2-methoxy-ethyl)-methyl-amino]-pyridin-3-yl}-amide

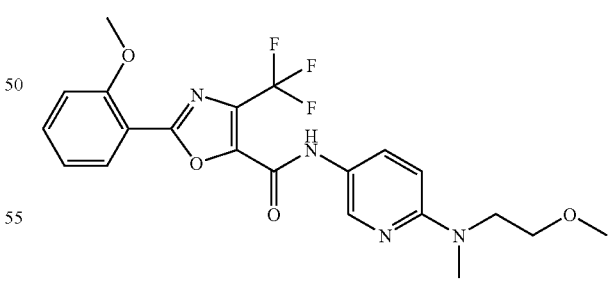

With a procedure similar to example 1 above, 2-(2-methoxy-phenyl)-4-trifluoromethyl-oxazole-5-carboxylic acid {6-[(2-methoxy-ethyl)-methyl-amino]-pyridin-3-yl}-amide was prepared from 2-(2-methoxy-phenyl)-4-trifluoromethyl-oxazole-5-carboxylic acid and $N^2$-(2-methoxy-ethyl)-$N^2$-methyl-pyridine-2,5-diamine. LCMS calcd for C21H21F3N4O4 (m/e) 450, obsd 451 (M+H).

Example 114

Preparation of 2-(2-methoxy-phenyl)-4-trifluoromethyl-oxazole-5-carboxylic acid {2-[(2-methoxy-ethyl)-methyl-amino]-pyrimidin-5-yl}-amide

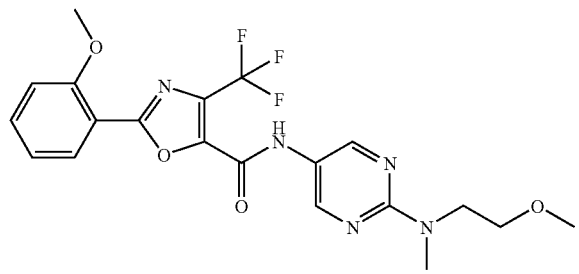

With a procedure similar to example 1 above, 2-(2-methoxy-phenyl)-4-trifluoromethyl-oxazole-5-carboxylic acid {2-[(2-methoxy-ethyl)-methyl-amino]-pyrimidin-5-yl}-amide was prepared from 2-(2-methoxy-phenyl)-4-trifluoromethyl-oxazole-5-carboxylic acid and N-(2-methoxy-ethyl)-N-methyl-pyrimidine-2,5-diamine. LCMS calcd for C20H20F3N5O4 (m/e) 451, obsd 452 (M+H).

Example 115

Preparation of 2-[2-(2-methoxy-ethoxy)-phenyl]-4-trifluoromethyl-oxazole-5-carboxylic acid {6-[(2-methoxy-ethyl)-methyl-amino]-pyridin-3-yl}-amide

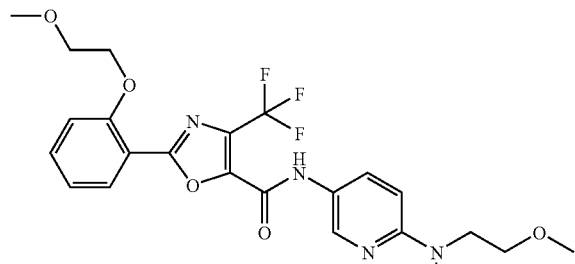

With a procedure similar to example 1 above, 2-[2-(2-methoxy-ethoxy)-phenyl]-4-trifluoromethyl-oxazole-5-carboxylic acid {6-[(2-methoxy-ethyl)-methyl-amino]-pyridin-3-yl}-amide was prepared from 2-[2-(2-methoxy-ethoxy)-phenyl]-4-trifluoromethyl-oxazole-5-carboxylic acid and $N^2$-(2-methoxy-ethyl)-$N^2$-methyl-pyridine-2,5-diamine. LCMS calcd for C23H25F3N4O5 (m/e) 494, obsd 495 (M+H).

Example 116

Preparation of 2-phenyl-5-trifluoromethyl-oxazole-4-carboxylic acid [6-(1-oxo-1$\lambda^4$-thiomorpholin-4-yl)-pyridin-3-yl]-amide

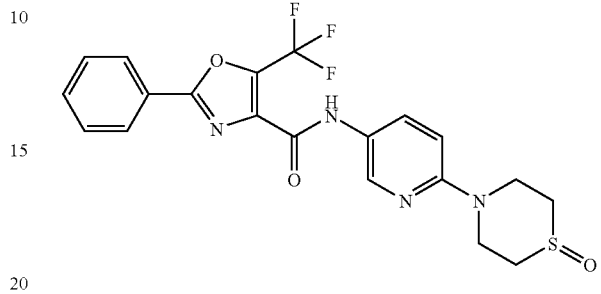

2-Phenyl-5-trifluoromethyl-oxazole-4-carboxylic acid (6-thiomorpholin-4-yl-pyridin-3-yl)-amide (30 mg, 0.07 mmol) was dissolved in 3 mL of methylene chloride, and cooled down to −78° C. One equivalent of 3-chloroperoxybenzoic acid (12 mg, 0.07 mmol) was added. The reaction mixture was warmed up to room temperature and stirred for 2 hours. The reaction mixture was concentrated under reduced pressure, and then purified by flash chromatography (Merck silica gel 60, 230-400 mesh, 0-20% methanol in methylene chloride for 25 min) to gave 2-phenyl-5-trifluoromethyl-oxazole-4-carboxylic acid [6-(1-oxo-1$\lambda^4$-thiomorpholin-4-yl)-pyridin-3-yl]-amide as an off-white solid. LCMS calcd for C20H17F3N4O3S (m/e) 450, obsd 451 (M+H).

Example 117

Preparation of 2-phenyl-5-trifluoromethyl-oxazole-4-carboxylic acid [6-(1,1-dioxo-1$\lambda^6$-thiomorpholin-4-yl)-pyridin-3-yl]-amide

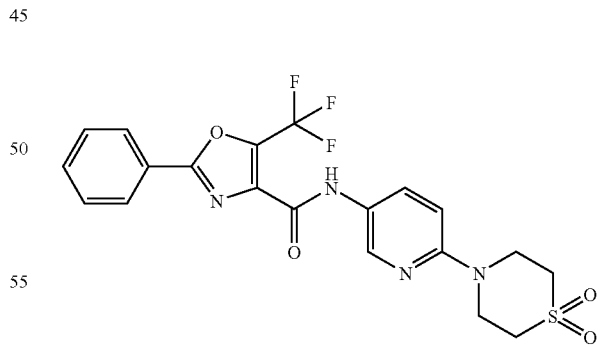

With a procedure similar to example 58 above, 2-phenyl-5-trifluoromethyl-oxazole-4-carboxylic acid [6-(1,1-dioxo-1$\lambda^6$-thiomorpholin-4-yl)-pyridin-3-yl]-amide was prepared from 2-phenyl-5-trifluoromethyl-oxazole-4-carboxylic acid (6-thiomorpholin-4-yl-pyridin-3-yl)-amide and two equivalents of 3-chloroperoxybenzoic acid. LCMS calcd for C20H17F3N4O4S (m/e) 466, obsd 467 (M+H).

Example 118

Preparation of 5-cyclohexyl-2-methyl-furan-3-carboxylic acid (6-morpholin-4-yl-pyridin-3-yl)-amide

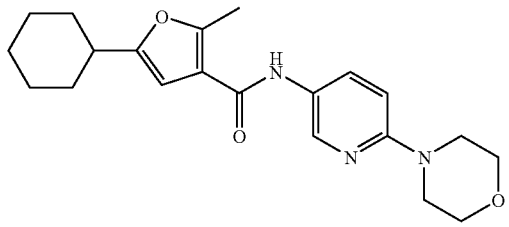

5-Cyclohexyl-2-methyl-furan-3-carboxylic acid (83 mg, 0.365 mmol), 6-morpholin-4-yl-pyridin-3-ylamine (83 mg, 0.4 mmol), and triethylamine (154 uL, 1.09 mmol) were dissolved in 5 mL of DMF and chilled in an ice bath. To this solution was added BOP (169 mg, 0.383 mmol) in one portion. The mixture was stirred at room temperature for one hour and then diluted with 30 mL ethyl acetate. The ethyl acetate solution was washed with saturated sodium bicarbonate (2×10 mL) and saturated sodium chloride (10 mL). The organic layer was dried over MgSO$_4$, filtered and evaporated to dryness under vacuum. The crude product was purified by flash chromatography using ethyl acetate/hexane to yield 5-cyclohexyl-2-methyl-furan-3-carboxylic acid (6-morpholin-4-yl-pyridin-3-yl)-amide as a light grey powder (87 mg, 64%). ES-MS calcd for C21H27N3O3 (m/e) 369.5, obsd 370.3 (M+H).

Example 119

Preparation of 5-cyclohexyl-2-ethyl-furan-3-carboxylic acid (6-morpholin-4-yl-pyridin-3-yl)-amide

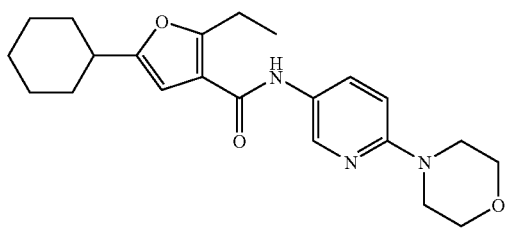

5-Cyclohexyl-2-ethyl-furan-3-carboxylic acid (26 mg, 0.116 mmol), 6-morpholin-4-yl-pyridin-3-ylamine (20 mg, 0.116 mmol), and triethylamine (49 uL, 0.348 mmol) were dissolved in 4 mL of DMF and chilled in an ice bath. To this solution was added BOP (53 mg, 0.121 mmol) in one portion. The mixture was stirred at room temperature, for one hour and then diluted with 30 mL ethyl acetate. The ethyl acetate solution was washed with saturated sodium bicarbonate (2×10 mL) and saturated sodium chloride (10 mL). The organic layer was dried over MgSO$_4$, filtered and evaporated to dryness under vacuum. The crude product was purified by flash chromatography using ethyl acetate/hexane to yield 5-cyclohexyl-2-ethyl-furan-3-carboxylic acid (6-morpholin-4-yl-pyridin-3-yl)-amide as a light grey powder (11.5 mg, 26%). ES-MS calcd for C22H29N3O3 (m/e) 383.5, obsd 384 (M+H).

Example 120

Preparation of 2-phenyl-5-trifluoromethyl-oxazole-4-carboxylic acid [5-(N-2-methoxyethyl-N-methyl)aminopyrazine]-2-yl-amide

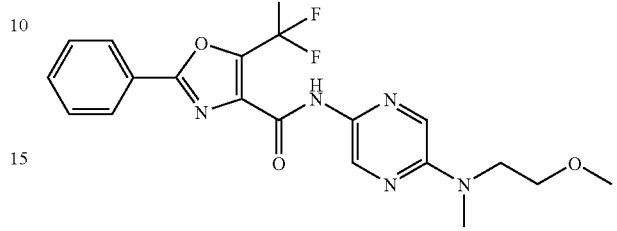

To a suspension of 2-phenyl-5-trifluoromethyl-oxazole-4-carboxylic acid (285 mg, 1.1 mmol) in methylene chloride (10 mL) cooled with an ice bath was added oxalyl chloride (0.22 mL, 2.5 mmol) and one drop of DMF. The mixture was stirred at 0° C. for 5 minutes and then at room temperature for 30 minutes. Solvents were evaporated and the residue was treated with toluene (10 mL) and solvents were further evaporated. The residue was dried in vacuum and dissolved in methylene chloride (10 mL). The solution was cooled in an ice bath and treated with a methylene chloride solution (10 mL) containing pyridine (0.24 mL, 2.97 mmol) and 5-(N-2-methoxyethyl-N-methyl)-pyrazine-2,5-diamine (180 mg, 1.0 mmol). Ice bath was removed and the mixture was stirred at room temperature for 90 minutes. The mixture was then extracted with methylene chloride and water. The organic layer was washed with aqueous sodium bicarbonate solution and brine, dried over sodium sulfate and concentrated. The residue was purified through a Biotage flash column chromatography eluted with ethyl acetate and hexanes (gradient elution with 10% to 50% ethyl acetate in hexanes) to give 2-phenyl-5-trifluoromethyl-oxazole-4-carboxylic acid [5-(N-2-methoxyethyl-N-methyl)aminopyrazine]-2-yl-amide as a yellow solid (205 mg, 48%). LCMS calcd for C19H18F3N5O3 (m/e) 421.3, obsd 422.2 (M+H).

Example 121

Preparation of 2-phenyl-5-trifluoromethyl-oxazole-4-carboxylic acid [5-(N-tetrahydropyran-4-yl)aminopyrazine]-2-yl-amide

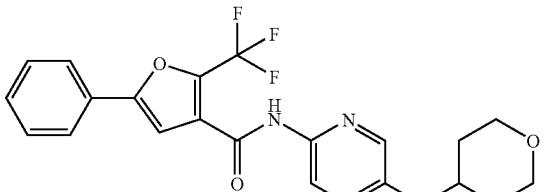

With a procedure similar to example 62 above, 2-phenyl-5-trifluoromethyl-oxazole-4-carboxylic acid [5-(N-tetrahydropyran-4-yl)aminopyrazine]-2-yl-amide was prepared from 2-phenyl-5-trifluoromethyl-oxazole-4-carboxylic acid and N-(tetrahydropyran-4-yl)pyrazine-2,5-diamine. LCMS calcd for C20H18F3N5O3 (m/e) 433, obsd 434 (M+H).

Example 122

Preparation of 2-phenyl-5-trifluoromethyl-oxazole-4-carboxylic acid-[6-(tetrahydropyran-4-yl-amino)pyridine-3-yl]amide

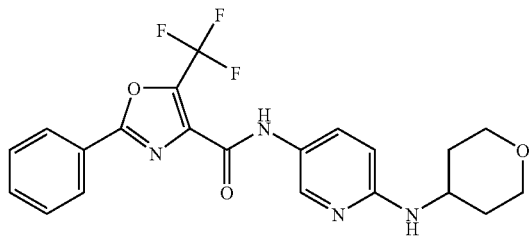

To a N,N-dimethylformamide solution (5 mL) containing 2-phenyl-5-trifluoromethyl-oxazole-4-carboxylic acid (134 mg, 0.52 mmol) and 2-(N-tetrahydropyran-4-yl)-2,5-diaminopyridine (101 mg, 0.52 mmol) was added triethylamine (0.15 mL, 1.0 mmol) and bromo tripyrrolidinophosphonium hexafluorophosphate (243 mg, 0.52 mmol). The mixture was stirred at room temperature overnight. Solvents were evaporated and the residue was purified through flash column chromatography using ethyl acetate and hexanes (1/1 to 2/1 ratio) to give a fluffy solid (108 mg). LCMS calcd for C21H19F3N4O3 m/e 432.41, obsd 433.1 (ES, M+H).

Example 123

Preparation of (S)-2-phenyl-5-trifluoromethyl-oxazole-4-carboxylic acid-[6-(tetrahydrofuran-3-ylamino)pyridin-3-yl]amide

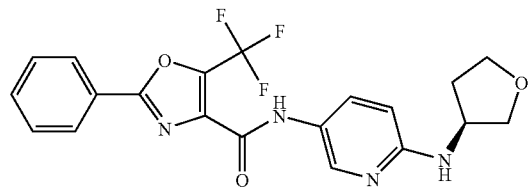

With a method similar to example 17 above, (S)-2-Phenyl-5-trifluoromethyl-oxazole-4-carboxylic acid-[6-(tetrahydrofuran-3-ylamino)pyridin-3-yl]amide was prepared from 2-phenyl-5-trifluoromethyl-oxazole-4-carboxylic acid and (S)-2-N-(tetrahydrofuran-3-yl)-2,5-diaminopyridine. LCMS calcd for C20H17F3N4O3 m/e 418.38, obsd 419.2 (AP, M+H).

Example 124

Preparation of 2-Phenyl-5-trifluoromethyl-oxazole-4-carboxylic acid-[6-(tetrahydrofuran-3-ylamino)pyridin-3-yl]amide

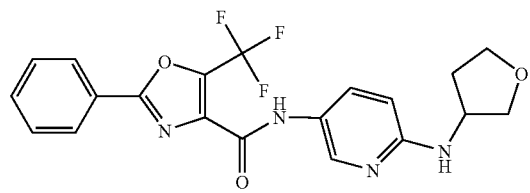

With a method similar to example 17 above, 2-phenyl-5-trifluoromethyl-oxazole-4-carboxylic acid-[6-(tetrahydrofuran-3-ylamino)pyridin-3-yl]amide was prepared from 2-phenyl-5-trifluoromethyl-oxazole-4-carboxylic acid and 2-N-(tetrahydrofuran-3-yl)-2,5-diaminopyridine. LCMS calcd for C20H17F3N4O3 m/e 418.38, obsd 419.13 (ES, M+H).

Example 125

Preparation of 2-phenyl-5-trifluoromethyl-oxazole-4-carboxylic acid [6-(cis-3-hydroxy-cyclopentylamino)-pyridin-3-yl]-amide

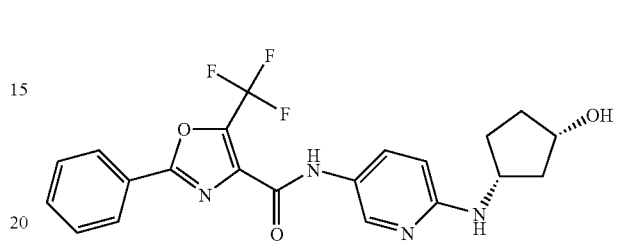

A mixture of 5-methyl-2-phenyl-oxazole-4-carboxylic acid (371 mg, 1.44 mmol), DCM (5 mL), and DMF (cat.) was stirred under Ar, cooled in an ice bath, and oxalyl chloride (252 μL, 2.89 mmol) was added dropwise into the mixture over 5 min. The mixture was immediately allowed to warm to room temperature and after 1.5 hr the reaction was concentrated to dryness and then dried again from DCM. The white yellow solid was dissolved in 5 mL of DCM and added dropwise into a solution containing $N^2$-[cis-3-(tert-butyl-dimethyl-silanyloxy)-cyclopentyl]-pyridine-2,5-diamine (443.7 mg, 1.44 mmol), DMAP (cat.), and TEA (602 μL, 4.33 mmol) in 5 mL of DCM under Ar cooled in an ice bath. The reaction was allowed to warm to room temperature overnight. The reaction was concentrated, supported onto silica gel, and purified by flash chromatography using the Analogix system with a 40 g Redisep silica gel column with increasing concentrations of EtOAc in hexane (30 mL/min, equilibrate with 5%, 0-5 min: 5%, 5-20 min: 5 to 30%, 20-40 min: 30%). The appropriate fractions were collected and dried producing a red solid, 2-phenyl-5-trifluoromethyl-oxazole-4-carboxylic acid {6-[cis-3-(tert-butyl-dimethyl-silanyloxy)-cyclopentylamino]-pyridin-3-yl}-amide, 456 mg, 72.9% (LCMS 3.91 min, 547 (M+H), calcd. C27H33F3N4O3S (m/e) 546, 10-100% ACN in H2O/HCOOH 0.3%, C18, ESI). The protected alcohol was dissolved in ACN (10 mL) and 5% aqueous HF solution (1.3 mL) was added slowly dropwise. The reaction was stirred for 22 hr, concentrated, and liquid extracted with DCM. The organic layer was washed with saturated sodium bicarbonate and brine, dried over sodium sulfate, and concentrated to dryness. The dried material was redissolved in DCM (14 mL) and TFA (6 mL) was added slowly dropwise. After 1.5 hr the solution was concentrated to dryness, supported on silica gel, and purified by flash chromatography with a 12 g 12M Biotage silica gel column with increasing concentrations of EtOAc in Hexane (250 mL increments of 5, 10, 30, 50, 80, 100% and then 5% MeOH in EtOAc). The appropriate fractions were collected and dried producing a white/yellow solid 189 mg, 53% (LCMS 3.00 min, 433 (M+H), calcd. C21H19F3N4O3 (m/e) 432, 10-100% ACN in H2O/HCOOH 0.3%, C18, APCI).

Example 126

Preparation of 2-phenyl-5-trifluoromethyl-oxazole-4-carboxylic acid [6-(trans-3-hydroxy-cyclopentylamino)-pyridin-3-yl]-amide

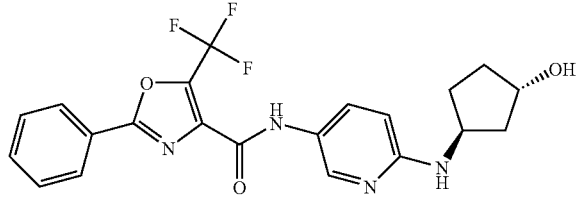

With a procedure similar to example 64 above, 2-phenyl-5-trifluoromethyl-oxazole-4-carboxylic acid [6-(trans-3-hydroxy-cyclopentylamino)-pyridin-3-yl]-amide was prepared from 2-phenyl-oxazole-4-carboxylic acid and $N^2$-[trans-3-(tert-butyl-dimethyl-silanyloxy)-cyclopentyl]-pyridine-2,5-diamine. The product was light yellow, 880 mg, 89% yield, (LCMS 2.71 min, 433 (M+H), calcd. C21H19F3N4O3 (m/e) 432, 10-100% ACN in H2O/HCOOH 0.3%, C18, APCI).

Example 127

Preparation of 2-phenyl-5-trifluoromethyl-oxazole-4-carboxylic acid {6-((1S,3S)-[3-hydroxy-cyclopentylamino]-pyridin-3-yl}-amide

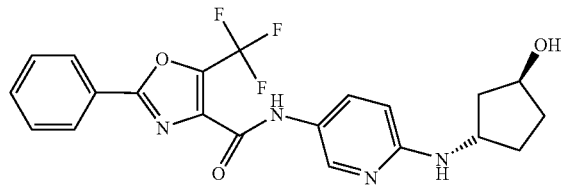

To a flask containing 2-phenyl-5-trifluoromethyl-oxazole-4-carboxylic acid {6-((1S,3S)-[3-(tert-butyl-dimethyl-silanyloxy)-cyclopentylamino]-pyridin-3-yl}-amide (8 mg, 0.015 mmol) was added dichloromethane (0.7 mL) and trifluoroacetic acid (0.3 mL). When the starting material was consumed, as indicated by TLC, the reaction mixture was neutralized with triethylamine and concentrated to dryness. The residue was dissolved in a minimal amount of dichloromethane and hexanes were added dropwise to precipitate the product. The light pink solid was filtered and washed with hexanes to yield 2-phenyl-5-trifluoromethyl-oxazole-4-carboxylic acid {6-((1S,3S)-[3-hydroxy-cyclopentylamino]-pyridin-3-yl}-amide. LCMS for $C_{21}H_{19}F_3N_4O_3$ calculated (m/e) 432, found 433 (M+H).

Example 128

Preparation of 2-phenyl-5-trifluoromethyl-oxazole-4-carboxylic acid {6-((1R,3R)-[3-hydroxy-cyclopentylamino]-pyridin-3-yl}-amide

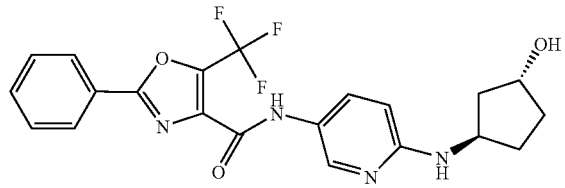

With a method similar to that used for the preparation 2-phenyl-5-trifluoromethyl-oxazole-4-carboxylic acid {6-((1S,3S)-[3-hydroxy-cyclopentylamino]-pyridin-3-yl}-amide above, 2-phenyl-5-trifluoromethyl-oxazole-4-carboxylic acid {6-((1R,3R)-[3-hydroxy-cyclopentylamino]-pyridin-3-yl}-amide was prepared from 2-phenyl-5-trifluoromethyl-oxazole-4-carboxylic acid {6-((1R,3R)-[3-(tert-butyl-dimethyl-silanyloxy)-cyclopentylamino]-pyridin-3-yl}-amide. LCMS for $C_{21}H_{19}F_3N_4O_3$ calculated (m/e) 432, found 433 (M+H).

Example 129

Preparation of 2-phenyl-5-trifluoromethyl-oxazole-4-carboxylic acid [5-(3-(S)-methoxy-pyrolidinyl)-pyridin-2-yl]-amide

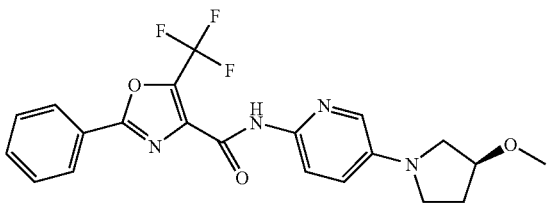

A solution of (170 mg, 0.76 mmol) of 5-(3-(S)-methoxy-pyrrolidin-1-yl)-2-nitro-pyridine in EtOH (20 mL) was treated with 10% Pd/C (80 mg, 0.08 mmol). The resulting mixture was hydrogenated under atmospheric pressure for 1 h and then filtered. The solids were washed three times with EtOH and the combined organic layer was evaporated to the corresponding crude aminopyridine. This product, without further characterization, was dissolved in CH2Cl2 (15 mL). The resulting solution was then treated with diisopropylethylamine (790 µL, 4.6 mmol) and a catalytic amount of DMAP.

A slurry of 220 mg (0.83 mmol) of 2-phenyl-5-trifluoromethyl-oxazole-4-carboxylic acid in CH2Cl2 (15 mL) was treated with 80 µL (0.92 mmol) of oxalyl chloride and a catalytic amount of DMF at rt. After stirring for 10 min the slurry disappeared. The solvent was evaporated under reduced pressure to dryness to afford the corresponding acid chloride. This intermediate, without characterization was dissolved in about 15 mL of CH2Cl2 and added under vigorous stirring to the solution that contained the crude aminopyridine product described above. This combined mixture was stirred for 30 min and then concentrated. The residue was chromatographed on a silica gel column with a 0-20% Et2O in toluene gradient to afford the product as a yellow solid. (170 mg, 52% yield). HRMS m/z calcd for $C_{21}H_{19}F_3N_4O_3$ [M+H]$^+$: 433.1482; Found: 433.1482.

Example 130

Preparation of 2-phenyl-5-trifluormethyl-oxazole-4-carboxylic acid {5-[(2-methoxy-ethyl)-methyl-amino]-pyridin-2-yl}amide

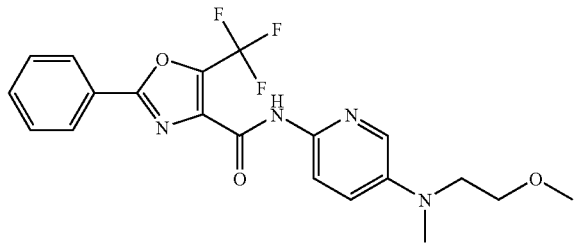

With a procedure similar to example 66 above, 2-phenyl-5-trifluoromethyl-oxazole-4-carboxylic acid {5-[(2-methoxy-ethyl)-methyl-amino]-pyridin-2-yl}amide was prepared from (2-methoxyethyl)-methyl-(6-nitropyridin-3-yl)-amine and 2-phenyl-5-trifluoromethyl-oxazole-4-carboxylic acid. The product was isolated as a yellow solid (200 mg, 37% yield). HRMS m/z calcd for $C_{20}H_{19}F_3N_4O_3$ $[M+H]^+$: 421.1482; Found: 421.1481.

Example 131

Preparation of 2-phenyl-5-trifluoromethyl-oxazole-4-carboxylic acid [6-(3-hydroxyazetidin-1-yl)-pyridin-3-yl]-amide

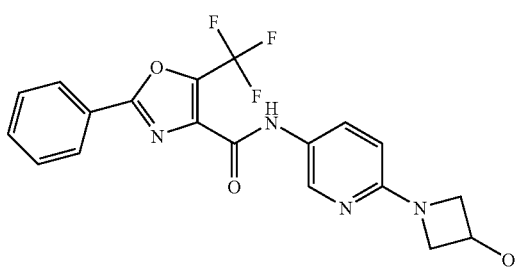

1-(5-Nitro-pyridin-2-yl)-azetidin-3-ol (400 mg, 2 mmol) was hydrogenated at 35 psi for 2¾ hrs with 10% Pd/C (40 mg) in EtOH (30 mL) and acetic acid (2 drops). The mixture was filtered through a celite plug, evaporated and then co-evaporated with toluene. The residue was dissolved in DMF (15 mL). One half of this solution (7.5 mL, ~1 mmol) was removed. To this was added 2-phenyl-5-trifluoromethyl-oxazole-4-carboxylic acid (257 mg, 1 mmol), $Et_3N$ (422 uL, 3 mmol) and BOP (464 mg. 1.05 mmol). The reaction was stirred for 1 hr at room temperature. Following work-up as above, the crude material was purified by flash chromatography to yield 2-phenyl-5-trifluoromethyl-oxazole-4-carboxylic acid [6-(3-hydroxyazetidin-1-yl)-pyridin-3-yl]-amide as an off-white solid (41 mg). ES-MS calcd for C19H15F3N4O3 (m/e) 404.35, obsd 405.1 (M+H).

Example 132

Preparation of 2-phenyl-5-trifluoromethyl-oxazole-4-carboxylic acid {6-[(2-ethoxy-ethyl)-methyl-amino]-pyridin-3-yl}-amide

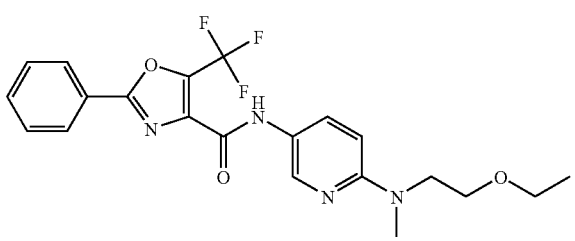

(2-Ethoxy-ethyl)-methyl-(5-nitro-pyridin-2-yl)-amine (150 mg, 0.666 mmol) was hydrogenated as above and reacted with 2-phenyl-5-trifluoromethyl-oxazole-4-carboxylic acid (171 mg, 0.666 mmol), $Et_3N$ (464 uL, 3.3 mmol) and BOP (309 mg. 0.699 mmol). Following work-up as above, the crude material was purified by flash chromatography to yield 2-phenyl-5-trifluoromethyl-oxazole-4-carboxylic acid {6-[(2-ethoxy-ethyl)-methyl-amino]-pyridin-3-yl}-amide as a yellow solid (194 mg). ES-MS calcd for C21H21F3N4O3 (m/e) 434.42, obsd 435.1 (M+H).

Example 133

Preparation of 2-phenyl-5-trifluoromethyl-oxazole-4-carboxylic acid [6-(3-methoxy-azetidin-1-yl)-pyridin-3-yl]-amide

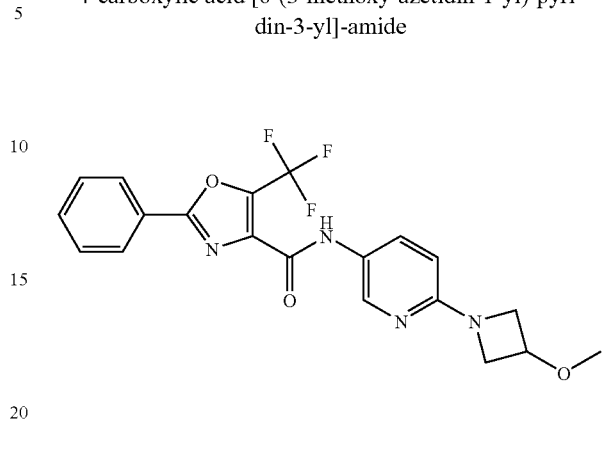

2-(3-Methoxy-azetidin-1-yl)-5-nitro-pyridine (120 mg, 0.5 mmol) was hydrogenated as above and reacted with 2-phenyl-5-trifluoromethyl-oxazole-4-carboxylic acid (141 mg, 0.55 mmol), $Et_3N$ (352 uL, 2.5 mmol) and BOP (232 mg. 0.525 mmol). Following work-up as above, the crude material was purified by flash chromatography to yield 2-phenyl-5-trifluoromethyl-oxazole-4-carboxylic acid [6-(3-methoxy-azetidin-1-yl)-pyridin-3-yl]-amide as a light green solid (45 mg). ES-MS calcd for C20H17F3N4O3 (m/e) 418.38, obsd 419.1 (M+H).

Example 134

Preparation of 2-phenyl-5-trifluoromethyl-oxazole-4-carboxylic acid (6-sec-butylamino-pyridin-3-yl)-amide

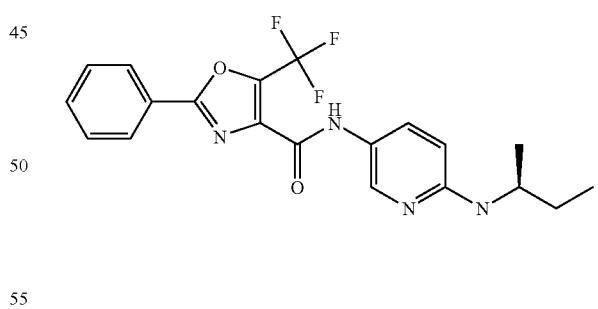

sec-Butyl-(5-nitro-pyridin-2-yl)-amine (97.5 mg, 0.5 mmol) was hydrogenated as above and reacted with 2-phenyl-5-trifluoromethyl-oxazole-4-carboxylic acid (135 mg, 0.525 mmol), $Et_3N$ (352 uL, 2.5 mmol) and BOP (232 mg. 0.525 mmol). Following work-up as above, the crude material was purified by flash chromatography to yield 2-phenyl-5-trifluoromethyl-oxazole-4-carboxylic acid (6-sec-butylamino-pyridin-3-yl)-amide as a light purple solid (83 mg). ES-MS calcd for C20H19F3N4O2 (m/e) 404.40, obsd 405.1 (M+H).

Example 135

Preparation of 2-phenyl-5-trifluoromethyl-oxazole-4-carboxylic acid [6-(3-ethoxy-azetidin-1-yl)-pyridin-3-yl]-amide

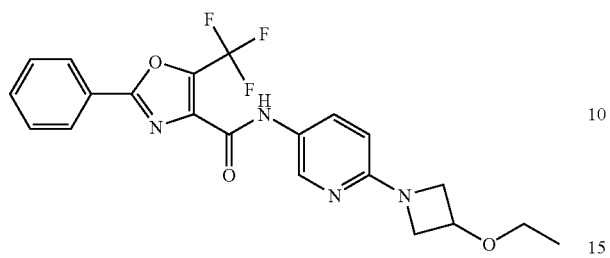

2-(3-Ethoxy-azetidin-1-yl)-5-nitro-pyridine (59 mg, 0.264 mmol) was hydrogenated as above and reacted with 2-phenyl-5-trifluoromethyl-oxazole-4-carboxylic acid (74 mg, 0.29 mmol), Et$_3$N (186 uL, 1.32 mmol) and BOP (122 mg. 0.277 mmol). Following work-up as above, the crude material was purified by flash chromatography to yield 2-phenyl-5-trifluoromethyl-oxazole-4-carboxylic acid [6-(3-ethoxy-azetidin-1-yl)-pyridin-3-yl]-amide as a solid (79 mg). ES-MS calcd for C21H19F3N4O3 (m/e) 432.41, obsd 433.1 (M+H).

Example 136

Preparation of 2-phenyl-5-trifluoromethyl-oxazole-4-carboxylic acid {6-[(2-cyclopropylmethoxy-ethyl)-methyl-amino]-pyridin-3-yl}-amide

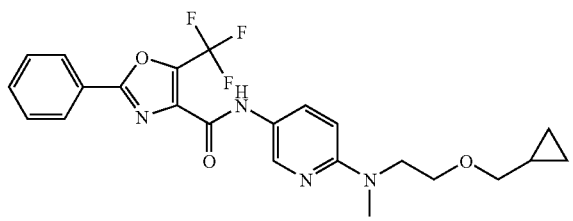

(2-Cyclopropylmethoxy-ethyl)-methyl-(5-nitro-pyridin-2-yl)-amine (82 mg, 0.326 mmol) was hydrogenated as above and reacted with 2-phenyl-5-trifluoromethyl-oxazole-4-carboxylic acid (92 mg, 0.359 mmol), Et$_3$N (229 uL, 1.63 mmol) and BOP (151 mg. 0.326 mmol). Following work-up as above, the crude material was purified by flash chromatography to yield 2-phenyl-5-trifluoromethyl-oxazole-4-carboxylic acid {6-[(2-cyclopropylmethoxy-ethyl)-methyl-amino]-pyridin-3-yl}-amide as a solid (95 mg). ES-MS calcd for C23H23F3N4O3 (m/e) 460.46, obsd 461.1 (M+H).

Example 137

Preparation of 2-phenyl-5-trifluoromethyl-oxazole-4-carboxylic acid {2-[(2-ethoxy-ethyl)-methyl-amino]-pyrimidin-5-yl}-amide

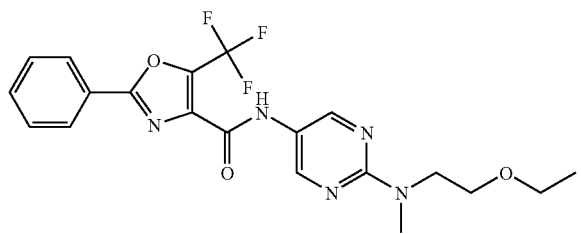

(2-Ethoxy-ethyl)-methyl-(5-nitro-pyrimidin-2-yl)-amine (150 mg, 0.663 mmol) was hydrogenated as above and reacted with 2-phenyl-5-trifluoromethyl-oxazole-4-carboxylic acid (179 mg, 0.696 mmol), Et$_3$N (466 uL, 3.3 mmol) and BOP (308 mg. 0.696 mmol). Following work-up as above, the crude material was purified by flash chromatography to yield 2-phenyl-5-trifluoromethyl-oxazole-4-carboxylic acid {2-[(2-ethoxy-ethyl)-methyl-amino]-pyrimidin-5-yl}-amide as a yellow solid (6 mg). ES-MS calcd for C20H20F3N5O3 (m/e) 435.41, obsd 436.1 (M+H).

Example 138

Preparation of (1-{5-[(2-phenyl-5-trifluoromethyl-oxazole-4-carbonyl)-amino]-pyridin-2-yl}-azetidin-3-yloxy)-acetic acid tert-butyl ester

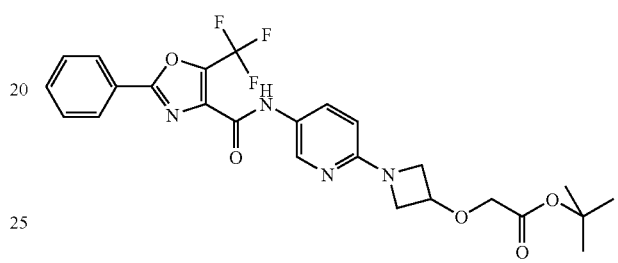

[1-(5-Nitro-pyridin-2-yl)-azetidin-3-yloxy]-acetic acid tert-butyl ester (210 mg, 0.679 mmol) was hydrogenated as above and reacted with 2-phenyl-5-trifluoromethyl-oxazole-4-carboxylic acid (183 mg, 0.71 mmol), DIPEA (355 uL, 2.03 mmol) and BOP (315 mg. 0.74 mmol). Following work-up as above, the crude material was purified by flash chromatography to yield (1-{5-[(2-phenyl-5-trifluoromethyl-oxazole-4-carbonyl)-amino]-pyridin-2-yl}-azetidin-3-yloxy)-acetic acid tert-butyl ester as a light brown solid (169 mg). ES-MS calcd for C25H25F3N4O5 (m/e) 518.50, obsd 519.1 (M+H).

Example 139

Preparation of (1-{5-[(2-phenyl-5-trifluoromethyl-oxazole-4-carbonyl)-amino]-pyridin-2-yl}-azetidin-3-yloxy)-acetic acid hydrochloride

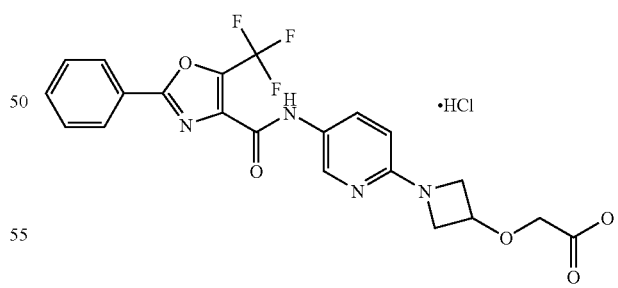

(1-{5-[(2-Phenyl-5-trifluoromethyl-oxazole-4-carbonyl)-amino]-pyridin-}-azetidin-3-yloxy)-acetic acid tert-butyl ester (132 mg) was treated with 8 mL of 97% TFA/H$_2$O for 1 hr at room temperature. The reaction mixture was evaporated from 1N HCl (2×0.5 mL) to yield (1-{5-[(2-phenyl-5-trifluoromethyl-oxazole-4-carbonyl)-amino]-pyridin-2-yl}-azetidin-3-yloxy)-acetic acid hydrochloride as a off-white solid (130 mg). ES-MS calcd for free base C21H17F3N4O5 (m/e) 462.39, obsd 463.0 (M+H).

Example 140

Preparation of (1-{5-[(2-phenyl-5-trifluoromethyl-oxazole-4-carbonyl)-amino]-pyridin-2-yl}-pyrrolidin-3-yloxy)-acetic acid tert-butyl ester

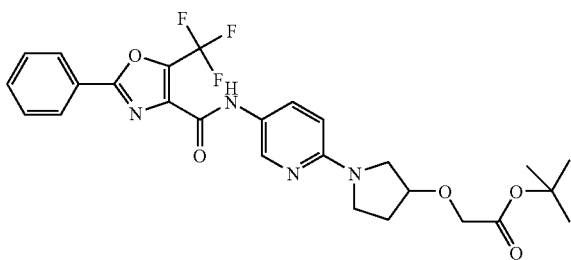

[1-(5-Nitro-pyridin-2-yl)-pyrrolidin-3-yloxy]-acetic acid tert-butyl ester (280 mg, 0.866 mmol) was hydrogenated as above and reacted with 2-phenyl-5-trifluoromethyl-oxazole-4-carboxylic acid (245 mg, 0.953 mmol), Et$_3$N (486 uL, 3.46 mmol) and BOP (402 mg. 0.909 mmol). Following work-up as above, the crude material was purified by flash chromatography to yield (1-{5-[(2-phenyl-5-trifluoromethyl-oxazole-4-carbonyl)-amino]-pyridin-2-yl}-pyrrolidin-3-yloxy)-acetic acid tert-butyl ester as a solid (170 mg). ES-MS calcd for C26H27F3N4O5 (m/e) 532.52, obsd 533.1 (M+H).

Example 141

Preparation of (1-{5-[(2-phenyl-5-trifluoromethyl-oxazole-4-carbonyl)-amino]-pyridin-2-yl}-pyrrolidin-3-yloxy)-acetic acid hydrochloride

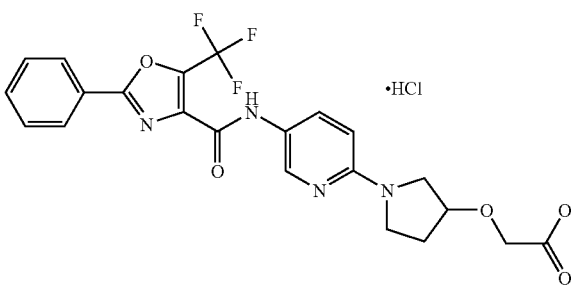

(1-{5-[(2-Phenyl-5-trifluoromethyl-oxazole-4-carbonyl)-amino]-pyridin-2-yl}-pyrrolidin-3-yloxy)-acetic acid tert-butyl ester (140 mg) was treated with 5 mL of 97% TFA/H$_2$O for 1.5 hr at room temperature. The reaction mixture was evaporated from 1N HCl (2×0.5 mL) to yield (1-{5-[(2-phenyl-5-trifluoromethyl-oxazole-4-carbonyl)-amino]-pyridin-2-yl}-azetidin-3-yloxy)-acetic acid hydrochloride as an off-white solid (110 mg). ES-MS calcd for free base C22H21F3N4O5 (m/e) 476.42, obsd 477.1 (M+H).

Example 142

Preparation of [2-(methyl-{5-[(2-phenyl-5-trifluoromethyl-oxazole-4-carbonyl)-amino]-pyridin-2-yl}-amino)-ethoxy]-acetic acid tert-butyl ester

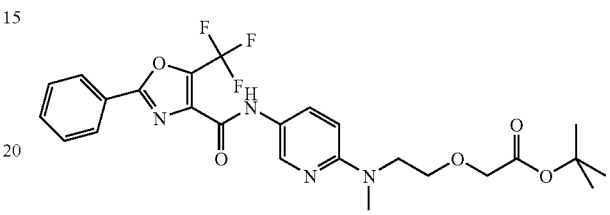

{2-[Methyl-(5-nitro-pyridin-2-yl)-amino]-ethoxy}-acetic acid tert-butyl ester (218 mg, 0.7 mmol) was hydrogenated as above and reacted with 2-phenyl-5-trifluoromethyl-oxazole-4-carboxylic acid (189 mg, 0.735 mmol), Et$_3$N (394 uL, 2.8 mmol) and BOP (325 mg. 0.735 mmol). Following work-up as above, the crude material was purified by flash chromatography to yield [2-(methyl-{5-[(2-phenyl-5-trifluoromethyl-oxazole-4-carbonyl)-amino]-pyridin-2-yl}-amino)-ethoxy]-acetic acid tert-butyl ester as a solid (110 mg). ES-MS calcd for C25H27F3N4O5 (m/e) 520.51, obsd 521.1 (M+H).

Example 143

Preparation of 2-phenyl-5-trifluoromethyl-oxazole-4-carboxylic acid {6-[methyl-(3-methyl-butyl)-amino]-pyridin-3-yl}-amide

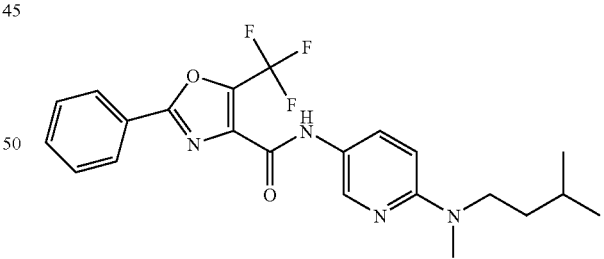

Methyl-(3-methyl-butyl)-(5-nitro-pyridin-2-yl)-amine (110 mg, 0.49 mmol) was hydrogenated as above and reacted with 2-phenyl-5-trifluoromethyl-oxazole-4-carboxylic acid (138 mg, 0.54 mmol), Et$_3$N (352 uL, 2.5 mmol) and BOP (227 mg. 0.514 mmol). Following work-up as above, the crude material was purified by flash chromatography to yield 2-phenyl-5-trifluoromethyl-oxazole-4-carboxylic acid {6-[methyl-(3-methyl-butyl)-amino]-pyridin-3-yl}-amide as a light purple solid (16 mg). ES-MS calcd for C22H23F3N4O2 (m/e) 432.51, obsd 433.2 M+H).

Example 144

Preparation of 2-phenyl-5-trifluoromethyl-oxazole-4-carboxylic acid {6-[(2-cyano-ethyl)-methyl-amino]-pyridin-3-yl}-amide

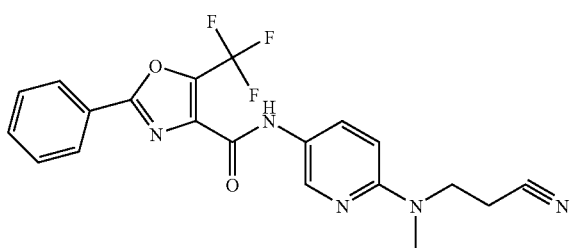

3-[Methyl-(5-nitro-pyridin-2-yl)-amino]-propionitrile (103 mg, 0.5 mmol) was hydrogenated as above and reacted with 2-phenyl-5-trifluoromethyl-oxazole-4-carboxylic acid (108 mg, 0.423 mmol), Et$_3$N (297 uL, 2.11 mmol) and BOP (196 mg. 0.444 mmol). Following work-up as above, the crude material was purified by flash chromatography to yield 2-phenyl-5-trifluoromethyl-oxazole-4-carboxylic acid {6-[(2-cyano-ethyl)-methyl-amino]-pyridin-3-yl}-amide as a solid (61 mg). ES-MS calcd for C20H16F3N5O2 (m/e) 415.38, obsd 416.1 (M+H).

Example 145

Preparation of 2-phenyl-5-trifluoromethyl-oxazole-4-carboxylic acid [6-(bicyclo[2.2.1]hept-2-ylamino)-pyridin-3-yl]-amide

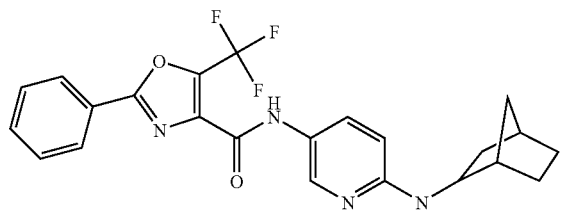

Bicyclo[2.2.1]hept-2-yl-(5-nitro-pyridin-2-yl)-amine (102 mg, 0.4 mmol) was hydrogenated as above and reacted with 2-phenyl-5-trifluoromethyl-oxazole-4-carboxylic acid (123 mg, 0.48 mmol), Et$_3$N (281 uL, 2 mmol) and BOP (194 mg. 0.444 mmol). Following work-up as above, the crude material was purified by flash chromatography to yield 2-phenyl-5-trifluoromethyl-oxazole-4-carboxylic acid [6-(bicyclo[2.2.1]hept-2-ylamino)-pyridin-3-yl]-amide as a light purple solid (30 mg). ES-MS calcd for C23H21F3N4O2 (m/e) 442.44, obsd 443.2 (M+H).

Example 146

DGAT Phospholipid FlashPlate Assay

Materials for the assay were: PL-FlashPlate: Phospholipid FlashPlates from PerkinElmer, catalog number SMP108; DAG (1,2-Dioleoyl-sn-glycerol) 10 mM suspended in water containing 0.1% Triton X-100; $^{14}$C-Pal-CoA (palmitoyl coenzyme A, [palmitoyl-1-$^{14}$C]) from PerkinElmer, catalog number NEC-555 with a specific activity of 55 mCi/mmol; and DGAT pellet, with a protein concentration of 9.85 mg/mL.

Aqueous buffers were prepared or purchased as follows: The coating buffer (CB) was purchased from PerkinElmer, catalog number SMP900A; the reaction buffer (RB) was 50 mM Tris-HCl, pH 7.5, 100 mM NaCl, 0.01% BSA in water; the washing buffer (WB) is 50 mM Tris-HCl, pH 7.5, 100 mM NaCl, 0.05% deoxycholic acid sodium salt in water; the dilution buffer (DB) was 50 mM Tris-HCl, pH 7.5, 100 mM NaCl, 1 mM EDTA, 0.2% Triton X-100 in water.

1,2-Dioleoyl-sn-glycerol (DAG, 10 mmoles) was diluted to 500 μM with coating buffer (CB). The diluted DAG solution was then added to 384-well PL-FlashPlates at 60 μl per well, and incubated at room temperature for 2 days. The coated plates were then washed twice with washing buffer (WB) before use. Test compounds were serial diluted to 2000, 666.7, 222.2, 74.1, 24.7, 8.2, 2.7 and 0.9 μM in 100% DMSO. Diluted compound were further diluted 10 fold with reaction buffer (RB). $^{14}$C-Pal-CoA was diluted to 8.3 μM with RB. The DGAT pellet was diluted to 0.13 mg protein/mL with dilution buffer (DB) immediately before it was added to the PL-FlashPlates to start the reaction. 20 μl of the RB-diluted compounds (or 10% DMSO in RB for Total and Blank), 15 μl of RB diluted 14C-Pal-CoA and 15 μl of DB diluted DGAT pellet (DB without DGAT for Blanks) were transferred to each well of the PL-FlashPlates. The reaction mixtures were incubated at 37° C. for 1 hour. The reactions were stopped by washing 3 times with WB. Plates were sealed with Top-seal and read on a Topcount instrument.

Calculation of IC$_{50}$: The IC$_{50}$ values for each compound were generated using an Excel template. The Topcount rpm readings of Total and Blank were used as 0% and 100% inhibition. The percent inhibition values of reactions in the presence of compounds were calculated, and plotted against compound concentrations. All data were fitted into a Dose Response One Site model (4 parameter logistic model) as the following:

$$(A+((B-A)/(1+((x/C)^D)))),$$

with A and B as the bottom and top of the curve (highest and lowest inhibition), respectively, and C as IC$_{50}$ and D as Hill Coefficient of the compound. The results are summarized in Table 1 below:

TABLE 1

| Compound of Example | Activity in DGAT Phospholipid FlashPlate Assay (A = IC$_{50}$ < 0.75 μM, B = IC$_{50}$ > 0.75 μM) |
|---|---|
| 1 | A |
| 2 | B |
| 3 | A |
| 4 | A |
| 5 | A |
| 6 | A |
| 7 | A |
| 8 | A |
| 9 | A |
| 10 | A |
| 11 | A |
| 12 | B |
| 13 | A |
| 14 | A |
| 15 | A |
| 16 | A |
| 17 | A |
| 18 | B |
| 18 | A |
| 20 | B |

TABLE 1-continued

| Compound of Example | Activity in DGAT Phospholipid FlashPlate Assay (A = $IC_{50}$ < 0.75 μM, B = $IC_{50}$ > 0.75 μM) |
|---|---|
| 21 | B |
| 22 | A |
| 23 | A |
| 24 | A |
| 25 | A |
| 26 | A |
| 27 | B |
| 28 | A |
| 29 | A |
| 30 | A |
| 31 | B |
| 32 | A |
| 33 | A |
| 34 | A |
| 35 | A |
| 36 | A |
| 37 | B |
| 38 | A |
| 39 | A |
| 40 | A |
| 41 | A |
| 42 | A |
| 43 | A |
| 44 | A |
| 45 | A |
| 46 | A |
| 47 | A |
| 48 | A |
| 49 | A |
| 50 | B |
| 51 | A |
| 52 | A |
| 53 | A |
| 54 | A |
| 55 | A |
| 56 | A |
| 57 | A |
| 58 | A |
| 59 | A |
| 60 | A |
| 61 | A |
| 62 | A |
| 63 | A |
| 64 | A |
| 65 | A |
| 66 | A |
| 67 | A |
| 68 | A |
| 69 | A |
| 70 | A |
| 71 | A |
| 72 | A |
| 73 | A |
| 74 | A |
| 75 | A |
| 76 | A |
| 77 | A |
| 78 | A |
| 79 | A |
| 80 | A |
| 81 | A |
| 82 | A |
| 83 | A |
| 84 | A |
| 85 | A |
| 86 | A |
| 87 | A |
| 88 | B |
| 89 | B |
| 90 | A |
| 91 | A |
| 92 | A |
| 93 | A |
| 94 | A |
| 95 | A |
| 96 | A |
| 97 | A |
| 98 | A |
| 99 | A |
| 100 | A |
| 101 | A |
| 102 | A |
| 103 | A |
| 104 | A |
| 105 | B |
| 106 | A |
| 107 | A |
| 108 | A |
| 109 | A |
| 110 | A |
| 111 | A |
| 112 | A |
| 113 | A |
| 114 | A |
| 115 | A |
| 116 | A |
| 117 | A |
| 118 | A |
| 119 | A |
| 120 | B |
| 121 | A |
| 122 | A |
| 123 | A |
| 124 | A |
| 125 | A |
| 126 | A |
| 127 | A |
| 128 | A |
| 129 | B |
| 130 | B |
| 131 | A |
| 132 | A |
| 133 | A |
| 134 | A |
| 135 | A |
| 136 | A |
| 137 | A |
| 138 | A |
| 139 | A |
| 140 | A |
| 141 | A |
| 142 | A |
| 143 | A |
| 144 | A |
| 145 | A |

It is to be understood that the invention is not limited to the particular embodiments of the invention described above, as variations of the particular embodiments may be made and still fall within the scope of the appended claims.

What is claimed is:

1. A compound of the formula (I):

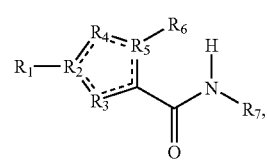

(I)

wherein:

$R_1$ is phenyl or phenyl substituted with a group selected from the group consisting of alkyl, —O-alkyl, haloalkoxy, methoxy-ethoxy, halogen, or cycloalkyl containing 4 to 7 carbon atoms;

R₂ is C;
R₃ is N;
R₄ is S or O;
R₅ is C;
R₆ is H, alkyl, halogen, haloalkyl, or thioalkyl;
R₇ is

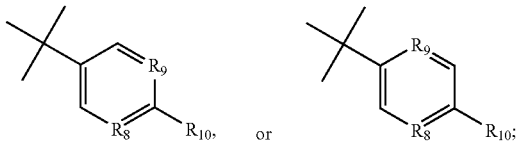

wherein one of R₈ and R₉ is nitrogen and the other is carbon;
R₁₀ is —NR₁₁R₁₂, O-alkyl, hydroxy-dimethylethylamino, hydroxyl-methylethylamino, cyclohept-2-ylamino, morpholino, thiomorpholino, oxothiomorpholino, dioxothiomorpholino, alkyl-carbamoyl-alkyl-amino, difluoroazetidine, ethoxyazetidine, or a 4- to 6-membered cyclic ring having from 1 to 3 hetero ring atoms selected from the group consisting of S, N and O substituted with a group selected from the group consisting of amino, —N(CH₃)C(O)CH₃, cyclopropanecarbonyl-methyl, —OCH₃, —OCH₂C(O)OC(CH₃)₃, OCH₂C(O)OH, —CH₂OH, —CH₂OCH₃ and —OH;
R₁₁ is H, lower alkyl, alkoxyalkyl, alkyl-aryl, trifluoromethyl, cyclopropylmethoxy-ethyl, —CH₂CH₂CN, hydroxyalkyl, cycloalkyl, or a 4- to 6-membered cyclic ring having from 1 to 3 hetero ring atoms selected from the group consisting of S, N and O, unsubstituted or substituted with a group selected from the group consisting of —OCH₃, —CH₂OH, —CH₂OCH₃, —OCH₂C(O)OC(CH₃)₃, —OCH₂C(O)OH and —OH;
R₁₂ is H or lower alkyl;
or a pharmaceutically acceptable salt thereof.

2. The compound according to claim 1 wherein:
R₁ is unsubstituted phenyl or phenyl substituted with a group selected from the group consisting of alkyl and halogen.

3. The compound according to claim 1 wherein:
R₁₀ is —NR₁₁R₁₂;
R₁₁ is H, lower alkyl, alkyl ether, alkyl alcohol, acyl or a 5- or 6-membered cyclic ring having from 1 to 3 hetero ring atoms selected from the group consisting of S, N and O, unsubstituted or substituted with a group selected from the group consisting of —OCH₃, —CH₂OH, —CH₂OCH₃ and —OH;
R₁₂ is H or lower alkyl;
or a pharmaceutically acceptable salt thereof.

4. The compound according to claim 1, wherein R₆ is —CF₃.

5. The compound according to claim 1 wherein said compound has the formula:

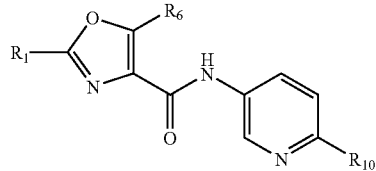

wherein R₁, R₆, and R₁₀ have definitions as defined previously.

6. The compound according to claim 1, wherein said compound is 2-phenyl-5-trifluoromethyl-oxazole-4-carboxylic acid [6-(ethyl-methyl-amino)-pyridin-3-yl]-amide.

7. The compound according to claim 1, wherein said compound is 2-(2-chloro-phenyl)-4-propyl-oxazole-5-carboxylic acid {6-[(2-methoxy-ethyl)-methyl-amino]-pyridin-3-yl}-amide.

8. The compound according to claim 1, wherein said compound is 2-phenyl-5-trifluoromethyl-oxazole-4-carboxylic acid [6-((S)-2-hydroxy-1-methyl-ethylamino)-pyridin-3-yl]-amide.

9. The compound according to claim 1, wherein said compound is 2-phenyl-5-trifluoromethyl-oxazole-4-carboxylic acid {6-[(2-methoxy-ethyl)-methyl-amino]-pyridin-3-yl}-amide.

10. The compound according to claim 1, wherein said compound is 2-(2-chloro-phenyl)-5-trifluoromethyl-oxazole-4-carboxylic acid {6-[(2-methoxy-ethyl)-methyl-amino]-pyridin-3-yl}-amide.

11. The compound according to claim 1, wherein said compound is 2-phenyl-5-trifluoromethyl-oxazole-4-carboxylic acid (6-thiomorpholin-4-yl-pyridin-3-yl)-amide.

* * * * *